United States Patent
Jeschke et al.

(10) Patent No.: US 9,763,451 B2
(45) Date of Patent: *Sep. 19, 2017

(54) METHOD FOR IMPROVED USE OF THE PRODUCTION POTENTIAL OF GENETICALLY MODIFIED PLANTS

(75) Inventors: Peter Jeschke, Bergisch Gladbach (DE); Wolfram Andersch, Bergisch Gladbach (DE); Heike Hungenberg, Langenfeld (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 1100 days.

This patent is subject to a terminal disclaimer.

(21) Appl. No.: 13/145,485

(22) PCT Filed: Dec. 16, 2009

(86) PCT No.: PCT/EP2009/009009
§ 371 (c)(1),
(2), (4) Date: Oct. 27, 2011

(87) PCT Pub. No.: WO2010/075966
PCT Pub. Date: Jul. 8, 2010

(65) Prior Publication Data
US 2012/0040835 A1    Feb. 16, 2012

(30) Foreign Application Priority Data

Dec. 29, 2008 (EP) .................................. 08173031
Feb. 23, 2009 (EP) .................................. 09153440

(51) Int. Cl.
*A01N 51/00* (2006.01)
*A01N 47/24* (2006.01)
*A01N 47/40* (2006.01)

(52) U.S. Cl.
CPC ............ *A01N 51/00* (2013.01); *A01N 47/24* (2013.01); *A01N 47/40* (2013.01)

(58) Field of Classification Search
None
See application file for complete search history.

(56) References Cited

U.S. PATENT DOCUMENTS

| | | |
|---|---|---|
| 4,761,373 A | 8/1988 | Anderson et al. |
| 5,013,659 A | 5/1991 | Bedbrook et al. |
| 5,084,082 A | 1/1992 | Sebastian |
| 5,141,870 A | 8/1992 | Bedbrook et al. |
| 5,198,599 A | 3/1993 | Thill |
| 5,273,894 A | 12/1993 | Strauch et al. |
| 5,276,268 A | 1/1994 | Strauch et al. |
| 5,304,732 A | 4/1994 | Anderson et al. |
| 5,322,938 A | 6/1994 | McPherson et al. |
| 5,331,107 A | 7/1994 | Anderson et al. |
| 5,378,824 A | 1/1995 | Bedbrook et al. |
| 5,463,175 A | 10/1995 | Barry et al. |
| 5,561,236 A | 10/1996 | Leemans et al. |
| 5,605,011 A | 2/1997 | Bedbrook et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,723,765 A | 3/1998 | Oliver et al. |
| 5,731,180 A | 3/1998 | Dietrich |
| 5,739,082 A | 4/1998 | Donn |
| 5,767,361 A | 6/1998 | Dietrich |
| 5,773,702 A | 6/1998 | Penner et al. |
| 5,776,760 A | 7/1998 | Barry et al. |
| 5,808,034 A | 9/1998 | Bridges et al. |
| 5,824,790 A | 10/1998 | Keeling et al. |
| 5,840,946 A | 11/1998 | Wong et al. |
| 5,908,810 A | 6/1999 | Donn |
| 5,908,975 A | 6/1999 | Caimi et al. |
| 5,928,937 A | 7/1999 | Kakefuda et al. |
| 5,965,755 A | 10/1999 | Sernyk et al. |
| 5,969,169 A | 10/1999 | Fan |
| 6,001,628 A | 12/1999 | Kossmann et al. |
| 6,013,861 A | 1/2000 | Bird et al. |

(Continued)

FOREIGN PATENT DOCUMENTS

DE    198 25 333 A1    12/1999
EP    0 485 506 B1      5/1992

(Continued)

OTHER PUBLICATIONS

Dow. Product Safety Assessment (PSA): Herculex® I Insect Protection. May 2, 2006. p. 1-3.*
Barry, G., et al, "Inhibitors of Amino Acid Biosynthesis: Strategies for Imparting Glyphosate Tolerance to Crop Plants," *Curr. Topics Plant Physiol.* 7:139-145, American Society of Plant Physiologists, United States (1992).
Barton, K.A., et al., "*Bacillus thuringiensis* δ-Endotoxin Expressed in Transgenic *Nicotiana tabacum* Provides Resistance to Lepidopteran Insects," *Plant Physiol.* 85:1103-1109, American Society of Plant Physiologists, United States (1987)

(Continued)

*Primary Examiner* — David H Kruse
(74) *Attorney, Agent, or Firm* — Arent Fox LLP

(57) ABSTRACT

The invention relates to a method for improving the utilization of the production potential of a genetically modified plant where the plant is treated with an effective amount of at least one compound of the formula (I)

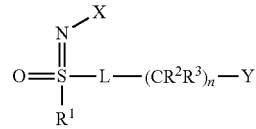

in which
$R^1$ to $R^3$, X, L, n and Y have the meanings given in the description.

20 Claims, No Drawings

(56) References Cited

U.S. PATENT DOCUMENTS

| | | | |
|---|---|---|---|
| 6,063,947 A | 5/2000 | DeBonte et al. | |
| 6,162,966 A | 12/2000 | Kossmann et al. | |
| 6,169,190 B1 | 1/2001 | Lanuza et al. | |
| 6,245,968 B1 | 6/2001 | Boudec et al. | |
| 6,268,549 B1 | 7/2001 | Sailland et al. | |
| 6,270,828 B1 | 8/2001 | DeBonte et al. | |
| 6,284,479 B1 | 9/2001 | Nichols | |
| 6,323,392 B1 | 11/2001 | Charne | |
| 6,331,531 B1 | 12/2001 | Kern | |
| 6,566,585 B1 | 5/2003 | Quanz | |
| 6,566,587 B1 | 5/2003 | Lebrun et al. | |
| 6,590,141 B1 | 7/2003 | Frohberg | |
| 6,734,341 B2 | 5/2004 | Singletary et al. | |
| 6,791,010 B1 | 9/2004 | Frohberg | |
| 6,812,010 B1 | 11/2004 | Derose et al. | |
| 6,890,732 B1 | 5/2005 | Loerz et al. | |
| 6,891,088 B1 | 5/2005 | Neuhaus et al. | |
| 6,951,969 B1 | 10/2005 | Loerz et al. | |
| 7,112,665 B1 | 9/2006 | Leemans et al. | |
| 7,186,898 B1 | 3/2007 | Kossmann et al. | |
| 7,456,003 B2 | 11/2008 | Kossmann et al. | |
| 8,796,175 B2 * | 8/2014 | Jeschke et al. | 504/100 |
| 2001/0007155 A1 | 7/2001 | Kossmann et al. | |
| 2001/0011378 A1 | 8/2001 | Kossmann et al. | |
| 2002/0031826 A1 | 3/2002 | Nichols | |
| 2002/0088023 A1 | 7/2002 | Kossmann et al. | |
| 2002/0133849 A1 | 9/2002 | Kossmann et al. | |
| 2002/0138876 A1 | 9/2002 | Block et al. | |
| 2002/0162138 A1 | 10/2002 | Kossmann et al. | |
| 2003/0106100 A1 | 6/2003 | Kossmann et al. | |
| 2003/0138927 A1 | 7/2003 | Heyer et al. | |
| 2003/0167527 A1 | 9/2003 | Emmermann et al. | |
| 2003/0167529 A1 | 9/2003 | Landschutze | |
| 2003/0175931 A1 | 9/2003 | Kossmann et al. | |
| 2003/0229923 A1 | 12/2003 | Kossmann et al. | |
| 2004/0014092 A1 | 1/2004 | Heyer et al. | |
| 2004/0078843 A1 * | 4/2004 | Kern | 800/279 |
| 2004/0154052 A1 | 8/2004 | Smeekens et al. | |
| 2004/0250313 A1 * | 12/2004 | Vincent et al. | 800/279 |
| 2005/0228027 A1 | 10/2005 | Zhu et al. | |
| 2005/0257283 A1 | 11/2005 | Matringe et al. | |
| 2006/0015966 A1 | 1/2006 | Landschutze | |
| 2006/0168690 A1 | 7/2006 | Shibatani et al. | |
| 2007/0149134 A1 | 6/2007 | Sebire et al. | |
| 2007/0203191 A1 * | 8/2007 | Loso et al. | 514/336 |
| 2007/0281860 A1 | 12/2007 | Baur et al. | |
| 2008/0108667 A1 | 5/2008 | Zhu et al. | |
| 2008/0207910 A1 | 8/2008 | Podhorez et al. | |
| 2008/0250533 A1 | 10/2008 | Frohberg | |
| 2009/0105235 A1 | 4/2009 | Jeschke et al. | |
| 2009/0317535 A1 | 12/2009 | Frohberg et al. | |

FOREIGN PATENT DOCUMENTS

| | | |
|---|---|---|
| EP | 0 571 427 B1 | 12/1993 |
| EP | 0 663 956 B1 | 7/1995 |
| EP | 0 719 338 B1 | 7/1996 |
| EP | 0 728 213 B1 | 8/1996 |
| JP | 2006-304779 A | 11/2006 |
| WO | WO 94/04693 A2 | 3/1994 |
| WO | WO 94/09144 A1 | 4/1994 |
| WO | WO 94/11520 A2 | 5/1994 |
| WO | WO 94/21795 A1 | 9/1994 |
| WO | WO 95/26407 A1 | 10/1995 |
| WO | WO 95/35026 A1 | 12/1995 |
| WO | WO 95/35031 A1 | 12/1995 |
| WO | WO 96/21023 A1 | 7/1996 |
| WO | WO 96/33270 A1 | 10/1996 |
| WO | WO 96/34968 A2 | 11/1996 |
| WO | WO 97/20936 A1 | 6/1997 |
| WO | WO 97/41218 A1 | 11/1997 |
| WO | WO 97/47806 A1 | 12/1997 |
| WO | WO 97/47807 A1 | 12/1997 |
| WO | WO 97/47808 A1 | 12/1997 |
| WO | WO 98/00549 A1 | 1/1998 |
| WO | WO 98/20145 A2 | 5/1998 |
| WO | WO 98/22604 A1 | 5/1998 |
| WO | WO 98/32326 A2 | 7/1998 |
| WO | WO 99/12950 A2 | 3/1999 |
| WO | WO 99/53072 A1 | 10/1999 |
| WO | WO 99/57965 A1 | 11/1999 |
| WO | WO 99/66050 A1 | 12/1999 |
| WO | WO 00/04173 A1 | 1/2000 |
| WO | WO 00/11192 A2 | 3/2000 |
| WO | WO 00/14249 A1 | 3/2000 |
| WO | WO 00/28052 A2 | 5/2000 |
| WO | WO 00/66746 A1 | 11/2000 |
| WO | WO 00/66747 A1 | 11/2000 |
| WO | WO 00/73422 A1 | 12/2000 |
| WO | WO 00/77229 A2 | 12/2000 |
| WO | WO 01/14569 A2 | 3/2001 |
| WO | WO 01/17333 A1 | 3/2001 |
| WO | WO 01/19975 A2 | 3/2001 |
| WO | WO 01/24615 A1 | 4/2001 |
| WO | WO 01/65922 A2 | 9/2001 |
| WO | WO 01/66704 A2 | 9/2001 |
| WO | WO 01/98509 A2 | 12/2001 |
| WO | WO 02/26995 A1 | 4/2002 |
| WO | WO 02/34923 A2 | 5/2002 |
| WO | WO 02/36782 A2 | 5/2002 |
| WO | WO 02/45485 A1 | 6/2002 |
| WO | WO 02/101059 A2 | 12/2002 |
| WO | WO 03/013226 A2 | 2/2003 |
| WO | WO 03/033540 A2 | 4/2003 |
| WO | WO 03/071860 A2 | 9/2003 |
| WO | WO 03/092360 A2 | 11/2003 |
| WO | WO 2004/040012 A2 | 5/2004 |
| WO | WO 2004/053219 A2 | 6/2004 |
| WO | WO 2004/056999 A1 | 7/2004 |
| WO | WO 2004/078983 A2 | 9/2004 |
| WO | WO 2004/090140 A2 | 10/2004 |
| WO | WO 2004/106529 A2 | 12/2004 |
| WO | WO 2005/002359 A2 | 1/2005 |
| WO | WO 2005/012515 A2 | 2/2005 |
| WO | WO 2005/017157 A1 | 2/2005 |
| WO | WO 2005/020673 A1 | 3/2005 |
| WO | WO 2005/030941 A1 | 4/2005 |
| WO | WO 2005/030942 A1 | 4/2005 |
| WO | WO 2005/093093 A2 | 10/2005 |
| WO | WO 2005/095617 A2 | 10/2005 |
| WO | WO 2005/095618 A2 | 10/2005 |
| WO | WO 2005/095619 A1 | 10/2005 |
| WO | WO 2005/095632 A2 | 10/2005 |
| WO | WO 2005/123927 A1 | 12/2005 |
| WO | WO 2006/007373 A2 | 1/2006 |
| WO | WO 2006/015376 A2 | 2/2006 |
| WO | WO 2006/018319 A1 | 2/2006 |
| WO | WO 2006/024351 A1 | 3/2006 |
| WO | WO 2006/032469 A2 | 3/2006 |
| WO | WO 2006/032538 A1 | 3/2006 |
| WO | WO 2006/045633 A1 | 5/2006 |
| WO | WO 2006/060029 A2 | 6/2006 |
| WO | WO 2006/060634 A2 | 6/2006 |
| WO | WO 2006/063862 A1 | 6/2006 |
| WO | WO 2006/072603 A2 | 7/2006 |
| WO | WO 2006/103107 A1 | 10/2006 |
| WO | WO 2006/108702 A1 | 10/2006 |
| WO | WO 2006/133827 A2 | 12/2006 |
| WO | WO 2006/136351 A2 | 12/2006 |
| WO | WO 2007/009823 A1 | 1/2007 |
| WO | WO 2007/024782 A2 | 3/2007 |
| WO | WO 2007/027777 A2 | 3/2007 |
| WO | WO 2007/039314 A2 | 4/2007 |
| WO | WO 2007/039316 A1 | 4/2007 |
| WO | WO 2007/095229 A2 | 8/2007 |
| WO | WO 2007/107326 A1 | 9/2007 |
| WO | WO 2007/131699 A2 | 11/2007 |
| WO | WO 2007/149134 A1 | 12/2007 |
| WO | WO 2008/017518 A1 | 2/2008 |
| WO | WO 2008/027073 A1 | 3/2008 |
| WO | WO 2008/027539 A1 | 3/2008 |
| WO | WO 2008/057129 A1 | 5/2008 |
| WO | WO 2008/080630 A1 | 7/2008 |
| WO | WO 2008/080631 A1 | 7/2008 |

(56) References Cited

FOREIGN PATENT DOCUMENTS

| | | | |
|---|---|---|---|
| WO | WO 2008/097235 A1 | 8/2008 | |
| WO | WO 2008/106006 A1 | 9/2008 | |
| WO | WO 2008/129060 A2 | 10/2008 | |
| WO | WO 2009/118297 A2 * | 10/2009 | |

OTHER PUBLICATIONS

Colby, S.R., "Calculating Synergistic and Antagonistic Responses of Herbicide Combinations," Weeds 15:20-22, Weed Science Society of America, United States (1967).

Comai, L., et al., "An Altered aroA Gene Product Confers Resistance to the Herbicide Glyphosate," Science 221:370-371, American Association for the Advancement of Science, United States (1983).

Crickmore, N., "The VIP Nomenclature," as referenced in Bacillus thuringiensis Toxin Nomenclature, main page accessed on Feb. 3, 2012 at <lifesci.sussex.ac.uk/home/Neil_Crickmore/Bt/intro.html>, and the link to the nomenclature accessed at <lifesci.sussex.ac.uk/home/Neil_Crickmore/Bt/vip.html>.

Crickmore, N., et al., "Revision of the Nomenclature for the Bacillus thuringiensis Pesticidal Crystal Proteins," Microbiol. Mol. Biol. Rev. 62(3):807-813, American Society for Microbiology, United States (1998).

Fischhoff, D.A., et al., "Insect Tolerant Transgenic Tomato Plants," Bio/technology 5:807-813, Nature Publishing Company, United States (1987).

Gasser, C.S., et al., "Structure, Expression, and Evolution of the 5-Enolpyruvylshikimate-3-phosphate Synthase Genes of Petunia and Tomato," J. Biol. Chem. 263(9):4280-4289, The American Society for Biochemistry and Molecular Biology, Inc., United States (1988).

Ishida, Y., et al., "High Efficiency transformation of maize (Zea mays L.) mediated by Agrobacterium tumefaciens," Nature Biotechnology 14:745-750, Nature Publishing Group, England (1996).

Moellenbeck, D.J., et al., "Insecticidal proteins from Bacillus thuringiensis protect corn from corn rootworms," Nature Biotechnology 19:668-672, Nature Publishing Group, England (2001).

Schnepf, H.E., et al., "Characterization of Cry34/Cry35 Binary Insecticidal Proteins from Diverse Bacillus thuringiensis Strain Collections," Appl. Environ. Microbiol. 71(4):1765-1774, American Society for Microbiology, United States (2005).

Shah, D.M., et al., "Engineering Herbicide Tolerance in Transgenic Plants," Science 233:478-481, American Society for the Advancement of Science, United States (1986).

Tranel, P.J. and Wright, T.R., "Resistance of weeds to ALS-inhibiting herbicides: what have we learned?" Weed Science 50:700-712, Weed Science Society of America, United States (2002).

Vaeck, M., et al., "Transgenic plants protected from insect attack," Nature 328:33-37, Nature Publishing Group, England (1987).

Willmitzer, L., "16 Transgenic plants," in Biotechnology, A Multivolume Comprehensive Treatise, vol. 2, pp. 627-659, Rehm, H.J., et al., eds., VCH Weinheim, Germany (1993).

English language Abstract of WIPO Patent Publication No. WO 99/57965 A1, European Patent Office, espacenet database—Worldwide (1999).

English language Abstract of WIPO Patent Publication No. WO 01/14569 A2, European Patent Office, espacenet database—Worldwide (2001).

English language Abstract of Japanese Patent Publication No. JP 2006-304779 A, Japanese Patent Office,Patent & Utility Model Gazette DB, Patent Abstracts of Japan, (2006).

International Search Report for International Application No. PCT/EP2009/009009, European Patent Office, Netherlands, mailed on Mar. 23, 2010.

Bauer, T.A., et al., "Response of Selected Weed Species to Postmergence Imazethapyr and Bentazon," Weed Tech. 9:236-242, The Weed Science Society of America, United States (1995).

Blackshaw, R.E., "HOE-39866 Use in Chemical Fallow Systems," Weed Tech. 3:420-428, The Weed Science Society of America, United States (1989).

Blackshaw, R.E., "Synergistic Mixes of DPX-A7881 and Clopyralid in Canola (Brassica napus)," Weed Tech. 3:690-695, The Weed Science Society of America, United States (1989).

Blackshaw, R.E., et al., "Herbicide Combinations for Postemergent Weed Control in Safflower (Carthamus tinctorius)," Weed Tech. 4:97-104, The Weed Science Society of America, United States (1990).

Blouin, D.C., et al., "Analysis of Synergistic and Antagonistic Effects of Herbicides Using Nonlinear Mixed-Model Methodology," Weed Tech. 18:464-472, The Weed Science Society of America, United States (2004).

Bradley, P.R., et al., "Response of Sorghum (Sorghum bicolor) to Atrazine, Ammonium Sulfate, and Glyphosate," Weed Tech. 14:15-18, The Weed Science Society of America, United States (2000).

Buker, III, R.S., et al., "Confirmation and Control of a Paraquat-Tolerant Goosegrass (Eleusine indica) Biotype," Weed Tech. 16:309-313, The Weed Science Society of America, United States (2002).

Burke, I.C., et al., "CGA-362622 Antagonizes Annual Grass Control with Clethodim," Weed Tech. 16:749-754, The Weed Science Society of America, United States (2002).

Flint, J.L., et al., "Analyzing Herbicide Interactions: A Statistical Treatment of Colby's Method," Weed Tech. 2:304-309, The Weed Science Society of America, United States (1988).

Gillespie, G.R. and Nalewaja, J.D., "Wheat (Triticum aestivum) Response to Triallate Plus Chlorsulfuron," Weed Tech. 3:20-23, The Weed Science Society of America, United States (1989).

Green, J.M., et al., "Metribuzin and Chlorimuron Mixtures for Preemergence Broadleaf Weed Control in Soybeans, Glycine max," Weed Tech. 2:355-363, The Weed Science Society of America, United States (1988).

Harker, K.N. and O'Sullivan, A., "Synergistic Mixtures of Sethoxydim and Fluazifop on Animal Grass Weeds," Weed Tech. 5:310-316, The Weed Science Society of America, United States (1991).

Kent, L.M., et al., "Effect of Ammonium Sulfate, Imazapyr, and Environment on the Phytotoxicity of Imazethapyr," Weed Tech. 5:202-205, The Weed Science Society of America, United States (1991).

Kotoula-Syka, E., et al., "Interactions between SAN 582H and Selected Safeners on Grain Sorghum (Sorghum bicolor) and Corn (Zea mays)," Weed Tech. 10:299-304, The Weed Science Society of America, United States (1996).

Lanclos, D.Y., et al., "Glufosinate Tank-Mix Combinations in Glufosinate-Resistant Rice (Oryza sativa)," Weed Tech. 16:659-663, The Weed Science Society of America, United States (2002).

Norris, J.L., et al., "Weed Control from Herbicide Combinations with Three Formulations of Glyphosate," Weed Tech. 15:552-558, The Weed Science Society of America, United States (2001).

Novosel, K.M., et al., "Metolachlor Efficacy as Influenced by Three Acetolactate Synthase-Inhibiting Herbicides," Weed Tech. 12:248-253, The Weed Science Society of America, United States (1998).

Palmer, E.W., et al., "Broadleaf Weed Control in Soybean (Glycine max) with CGA-277476 and Four Postemergence Herbicides," Weed Tech. 14:617-623, The Weed Science Society of America, United States (2000).

Rummens, F.H.A., "An Improved Definition of Synergistic and Antagonistic Effects," Weed Science 23:4-6, The Weed Science Society of America, United States (1975).

Salzman, F.P. and Renner, K.A.,"Response of Soybean to Combinations of Clomazone, Metribuzin, Linuron, Alachlor, and Atrazine," Weed Tech. 6:922-929, The Weed Science Society of America, United States (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," Weed Tech. 12:463-469, The Weed Science Society of America, United States (1998).

Shaw,D.R. and Arnold, J.C., "Weed Control from herbicide Combinations with Glyphosate," Weed Tech. 16:1-6, The Weed Science Society of America, United States (2002).

(56) References Cited

OTHER PUBLICATIONS

Snipes, C.E and Allen, R.L., "Interaction of Graminicides Applied in Combination with Pyrithiobac," *Weed Tech.* 10:889-892, The Weed Science Society of America, United States (1996).

Sun, Y.-P., et al., "Analysis of Joint Action of Insecticides Against House Flies," *J. Econ. Entomol.* 53:887-892, Entomological Society of America, United States (1960).

Tammes, P.M.L., "Isoboles, A Graphic Representation of Synergism in Pesticides," *Neth. J. Plant Path.* 70:73-80, Springer, Germany (1964).

Wehtje, G., and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).

Zhang, W., et al., "Fenoxaprop Interactions for Barnyardgrass (*Echinochloa crus-galli*) Control in Rice," *Weed Tech.* 19:293-297, The Weed Science Society of America, United States (2005).

\* cited by examiner

METHOD FOR IMPROVED USE OF THE PRODUCTION POTENTIAL OF GENETICALLY MODIFIED PLANTS

The invention relates to a method for improving the utilization of the production potential of genetically modified plants.

In recent years, there has been a marked increase in the proportion of genetically modified plants in agriculture, even if regional differences are still currently noticeable. Thus, for example, the proportion of genetically modified maize in the USA has doubled from 26% to 52% since 2001, while genetically modified maize has previously been of hardly any practical importance in Germany. However, in other European countries, for example in Spain, the proportion of genetically modified maize is already about 12%.

Genetically modified plants are employed mainly to utilize the production potential of respective plant varieties in the most favourable manner, at the lowest possible input of production means. The aim of the genetic modification of the plants is in particular the generation of resistance in the plants to certain pests or harmful organisms or else herbicides and also to abiotic stress (for example drought, heat or elevated salt levels). It is also possible to genetically modify a plant to increase certain quality or product features, such as, for example, the content of selected vitamins or oils, or to improve certain fibre properties.

Herbicide resistance or tolerance can be achieved, for example, by incorporating genes into the useful plant for expressing enzymes to detoxify certain herbicides, so that a relatively unimpeded growth of these plants is possible even in the presence of these herbicides for controlling broad-leaved weeds and weed grasses. Examples which may be mentioned are cotton varieties or maize varieties which tolerate the herbicidally active compound glyphosate (Roundup®), (Roundup Ready®, Monsanto) or the herbicides glufosinate or oxynil.

More recently, there has also been the development of useful plants comprising two or more genetic modifications ("stacked transgenic plants" or multiply genetically modified crops). Thus, for example, Monsanto has developed multiply genetically modified maize varieties which are resistant to the European corn borer (*Ostrinia nubilalis*) and the Western corn rootworm (*Diabrotica virgifera*). Also known are maize and cotton crops which are resistant both to the Western corn rootworm and the cotton bollworm and tolerant to the herbicide Roundup®.

It has now been found that the utilization of the production potential of genetically modified useful plants can be improved even more by treating the plants with one or more sulphoximines of the formula (I) defined below. Here, the term "treatment" includes all measures resulting in contact between these active compounds and at least one plant part. Plant parts are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, slips and seed.

Compounds of the formula (I)

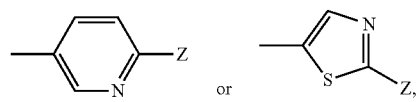

in which
X represents $NO_2$, CN or $COOR^4$,
L represents a single bond,
$R^1$ represents $C_1$-$C_4$-alkyl, or
$R^1$, sulphur and L together represent a 4-, 5- or 6-membered ring,
$R^2$ and $R^3$ independently of one another represent hydrogen, methyl, ethyl, fluorine, chlorine or bromine,
or
$R^2$ and $R^3$ together represent $-(CH_2)_2-$, $-(CH_2)_3-$, $-(CH_2)_4-$ or $-(CH_2)_5-$ and together with the carbon atom to which they are attached form a 3-, 4-, 5- or 6-membered ring,
n represents 0, 1, 2 or 3,
Y represents one of the radicals

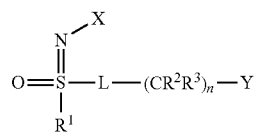

in which
Z represents halogen, $C_1$-$C_4$-alkyl, $C_1$-$C_4$-haloalkyl, $C_1$-$C_4$-alkoxy or $C_1$-$C_4$-haloalkoxy and
$R^4$ represents $C_1$-$C_3$-alkyl,
are known, for example, as agents for controlling animal pests, in particular insects (for example US patent application 2005/228027 A1, WO 2006/060029 A2, WO 2007/095229 A2, WO 2007/149134 A1, WO 2008/027539 A1, WO 2008/027073 A1, WO 2008/057129 A1, WO 2008/097235 A1, WO 2008/106006 A1). Furthermore, the increase of the insecticidal activity for a subgroup of sulphoximines by addition of suitable salts and, if appropriate, additives has been described (WO 2007/068355).

From these documents, the person skilled in the art is familiar with processes for preparing and for using compounds of the formula (I) and with their activity.

Depending, inter alia, on the nature of the substituents, the compounds of the formula (I) can be present as optical isomers or mixtures of isomers in varying compositions, which can be separated, if desired, in a customary manner. The present invention provides both the pure isomers and the isomer mixtures, their use and compositions comprising them. However, the following text will, for the sake of simplicity, always mention compounds of the formula (I), even though this is understood as meaning not only the pure compounds, but also, if appropriate, mixtures with various amounts of isomeric compounds.

Preferred subgroups of the compounds of the formula (I) are listed below:

In a particular group (Ia) of compounds of the formula (I), X represents the nitro group:

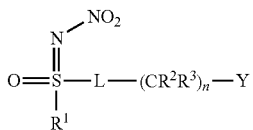

In a further particular group (Ib) of compounds of the formula (I), X represents the cyano group:

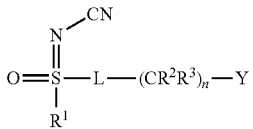

In a further particular group (Ic) of compounds of the formula (I), X represents $NO_2$ or CN, Y represents the 6-chloropyrid-3-yl radical:

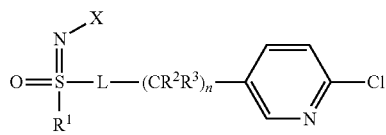

In a further particular group (Id) of compounds of the formula (I), X represents $NO_2$ or CN, Y represents the 6-trifluoromethylpyrid-3-yl radical:

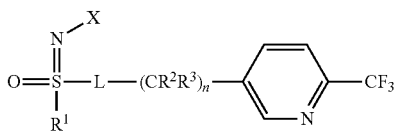

In a further particular group (Ie) of compounds of the formula (I), X represents $NO_2$ or CN, Y represents the 2-chloro-1,3-thiazol-5-yl radical:

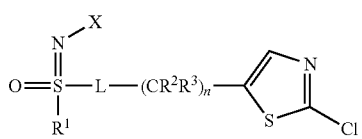

In a further particular group (If) of compounds of the formula (I), X represents $NO_2$ or CN, Y represents the 2-trifluoromethyl-1,3-thiazol-5-yl radical:

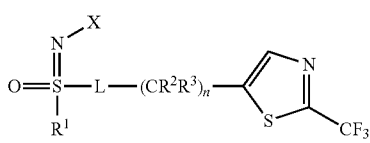

In a further particular group (Ig) of compounds of the formula (I), $R^1$, sulphur and L together form a 5-membered ring, X represents $NO_2$ or CN, Y represents 6-halopyrid-3-yl or 6-($C_1$-$C_4$-haloalkyl)pyrid-3-yl, particularly preferably 6-chloropyrid-3-yl or 6-trifluoromethylpyrid-3-yl, n preferably represents 0:

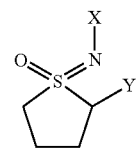

In a further particular group (Ih) of compounds of the formula (I), $R^1$, sulphur and L together form a 5-membered ring, X represents $NO_2$ or CN, Y represents 6-halopyrid-3-yl or 6-($C_1$-$C_4$-haloalkyl)pyrid-3-yl, particularly preferably 6-chloropyrid-3-yl or 6-trifluoromethylpyrid-3-yl, n preferably represents 0:

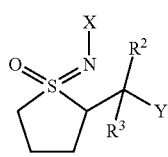

In a further particular group (Ii) of compounds of the formula (I), $R^1$ represents methyl, X represents $NO_2$ or CN, L represents a single bond and n preferably represents 1:

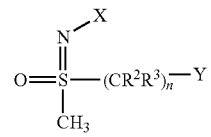

In a further particular group (Ij) of compounds of the formula (I), $R^1$ represents methyl, $R^2$ and $R^3$ independently of one another represent hydrogen or methyl, X represents $NO_2$ or CN, n preferably represents 1:

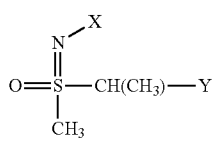

In a further particular group (Ik) of compounds of the formula (I), $R^1$ represents methyl, $R^2$ and $R^3$ together represent —$(CH_2)_2$— and form together with the carbon atom to which they are attached a 3-membered ring, X represents $NO_2$ or CN, n preferably represents 1:

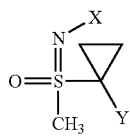
(Ik)

The compounds of the general formula (I) may, where appropriate, depending on the nature of the substituents, be in the form of geometric and/or optically active isomers or corresponding isomer mixtures of varying composition. The invention relates both to the pure isomers and to the isomer mixtures.

Specific mention may be made of the following compounds of the formula (I):

compound (I-1), [[6-chloropyridin-3-yl]methyl](methyl) oxido-$\lambda^4$-sulphanylidenecyanamide:

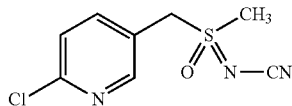

known from US patent application 2005/228027 A1 and WO 2007/149134 A1.

compound (I-2), [[6-trifluoromethylpyridin-3-yl]methyl] (methyl)oxido-$\lambda^4$-sulphanylidenecyanamide:

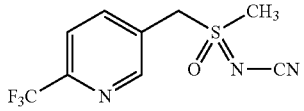

known from WO 2007/095229 A2, WO 2007/149134 A1 and WO 2008/027073 A1.

compound (I-3), methyl(oxido){[2-chloro-1,3-thiazol-5-yl]methyl}$\lambda^4$-sulphanylidenecyanamide:

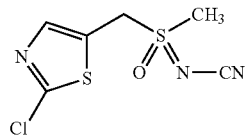

known from US patent application 2005/228027 A1.

compound (I-4), methyl(oxido){[2-trifluoromethyl-1,3-thiazol-5-yl]methyl}$\lambda^4$-sulphanylidenecyanamide:

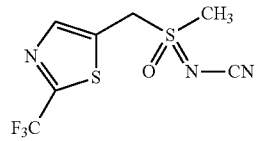

known from WO 2008/027539 A1.

compound (I-5), [[6-chloropyridin-3-yl]ethyl](methyl) oxido-$\lambda^4$-sulphanylidenecyanamide:

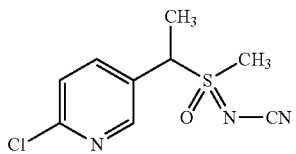

known from US patent application 2005/228027 A1, WO 2006/060029 A2, WO 2007/149134 A1 and WO 2008/097235.

compound (I-6), [[6-chloropyridin-3-yl]ethyl](methyl) oxido-$\lambda^4$-sulphanylidenecyanamide diastereomer:

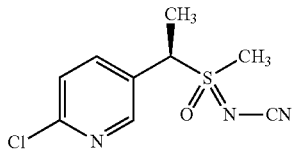

known from US patent application 2005/228027 A1 and WO 2007/149134 A1.

compound (I-7), [[6-chloropyridin-3-yl]ethyl](methyl) oxido-$\lambda^4$-sulphanylidenecyanamide diastereomer:

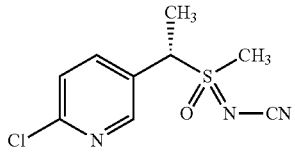

known from US patent application 2005/228027 A1 and WO 2007/149134 A1.

compound (I-8), [[6-trifluoromethylpyridin-3-yl]ethyl] (methyl)oxido-$\lambda^4$-sulphanylidenecyanamide:

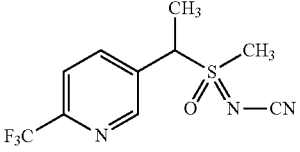

known from WO 2007/095229 A2, WO 2007/149134 A1, WO 2008/097235 A1 and WO 2008/207910 A1.

compound (I-9), [[6-(1,1-difluoroethyl)pyrid-3-yl]ethyl] (methyl)oxido-$\lambda^4$-sulphanylidenecyanamide:

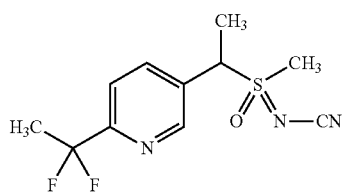 [SMILES: CC(c1ccc(C(C)(F)F)nc1)S(C)(=O)=NC#N]

known from WO 2007/095229 A2.

compound (I-10), [[6-difluoromethylpyrid-3-yl]ethyl](methyl)oxido-λ⁴-sulphanylidenecyanamide:

known from WO 2007/095229 A2.

compound (I-11), methyl(oxido) {1-[2-(trichloromethyl)pyrid-3-yl]ethyl)}λ⁴-sulphanylidenecyanamide:

known from WO 2007/095229 A2.

compound (I-12), methyl(oxido) {1-[2-(pentafluoroethyl)pyrid-3-yl]ethyl}λ⁴sulphanylidenecyanamide:

known from WO 2007/095229 A2.

compound (I-13), [[6-chlorodifluoromethylpyrid-3-yl]ethyl](methyl)oxido-λ⁴-sulphanylidenecyanamide:

known from WO 2007/095229 A2.

compound (I-14), methyl(oxido) {1-[2-(trifluoromethyl)-1,3-thiazol-5-yl]ethyl}λ⁴-sulphanylidenecyanamide:

known from WO 2008/027539 A1.

compound (I-15), methyl(oxido) {1-[6-(trifluormethyl)pyridin-3-yl]cyclopropyl}λ⁴-sulphanylidenecyanamide:

known from WO 2008/027073 A1.

compound (I-16), methyl(oxido) {1-(6-chloropyridin-3-yl)cyclopropyl}-λ⁴-sulphanylidenecyanamide:

known from WO 2008/027073 A1.

compound (I-17), 2-(6-chloropyridin-3-yl)-1-oxidotetrahydro-1H-1-λ⁴-thienylidenecyanamide:

known from WO 2004/149134 A1.

compound (I-18), 2-(6-trifluoromethylpyridin-3-yl)-1-oxidotetrahydro-1H-1-λ⁴-thienylidenecyanamide:

known from WO 2004/149134 A1.

compound (I-19), 1-oxo-2-(2-trifluoromethyl-1,3-thiazol-5-ylmethyl)tetrahydro-1-λ⁶-thiophen-1-ylidenecyanamide:

known from WO 2008/027539 A1.

compound (I-20), 1-oxo-2-(6-trifluoromethylpyrid-3-ylmethyl)tetrahydro-1-λ⁶-thiophen-1-ylidenecyanamide:

known from WO 2007/095229 A2.

compound (I-21), 1-oxo-2-(6-chloropyrid-3-ylmethyl)tetrahydro-1-$\lambda^6$-thiophen-1-ylidenecyanamide:

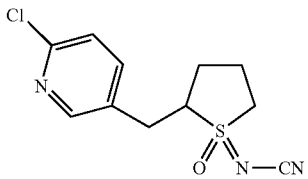 [SMILES: N#CN=S1(=O)CCCC1Cc1ccc(Cl)nc1]

known from US patent application 2005/228027 A1.
compound (I-22), 1-oxo-2-(6-chloropyrid-3-ylmethyl)tetrahydro-1-$\lambda^6$-thiophen-1-ylidenecyanamide diastereomer:

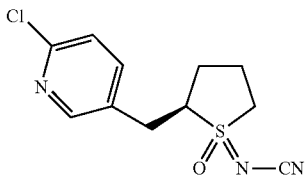 [SMILES: N#CN=S1(=O)CCC[C@@H]1Cc1ccc(Cl)nc1]

known from US patent application 2005/228027 A1.
compound (I-23), 1-oxo-2-(6-chloropyrid-3-ylmethyl)tetrahydro-1-$\lambda^6$-thiophen-1-ylidenecyanamide diastereomer:

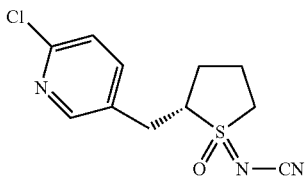 [SMILES: N#CN=S1(=O)CCC[C@H]1Cc1ccc(Cl)nc1]

known from US patent application 2005/228027 A1.

Preference is given to the following sulphoximines of the formula (I):
(I-1), [[6-chloropyridin-3-yl]methyl](methyl)oxido-$\lambda^4$-sulphanylidenecyanamide,
(I-2), [[6-trifluoromethylpyridin-3-yl]methyl](methyl)oxido-$\lambda^4$-sulphanylidenecyanamide,
(I-3), methyl(oxido){[2-chloro-1,3-thiazol-5-yl]methyl}$\lambda^4$-sulphanylidenecyanamide,
(I-4), methyl(oxido){[2-(trifluoromethyl)-1,3-thiazol-5-yl]methyl}$\lambda^4$-sulphanylidenecyanamide,
(I-5), [[6-chloropyridin-3-yl]ethyl](methyl)oxido-$\lambda^4$-sulphanylidenecyanamide,
(I-6), [[6-chloropyridin-3-yl]ethyl](methyl)oxido-$\lambda^4$-sulphanylidenecyanamide diastereomer,
(I-7), [[6-chloropyridin-3-yl]ethyl](methyl)oxido-$\lambda^4$-sulphanylidenecyanamide diastereomer,
(I-8), [[6-trifluoromethylpyridin-3-yl]ethyl](methyl)oxido-$\lambda^4$-sulphanylidenecyanamide,
(I-14), methyl(oxido){1-[2-(trifluoromethyl)-1,3-thiazol-5-yl]ethyl}$\lambda^4$-sulphanylidenecyanamide,
(I-15), methyl(oxido){1-[6-(trifluoromethyl)pyridin-3-yl]cyclopropyl}$\lambda^4$-sulphanylidenecyanamide,
(I-16), methyl(oxido){1-(6-chloropyridin-3-yl)cyclopropyl}$\lambda^4$-sulphanylidenecyanamide.

Particular preference is given to the following sulphoximines of the formula (I):
(I-5), [[6-chloropyridin-3-yl]ethyl](methyl)oxido-$\lambda^4$-sulphanylidenecyanamide,
(I-6), [[6-chloropyridin-3-yl]ethyl](methyl)oxido-$\lambda^4$-sulphanylidenecyanamide diastereomer,
(I-7), [[6-chloropyridin-3-yl]ethyl](methyl)oxido-$\lambda^4$-sulphanylidenecyanamide diastereomer,
(I-8), [[6-trifluoromethylpyridin-3-yl]ethyl](methyl)oxido-$\lambda^4$-sulphanylidenecyanamide,
(I-15), methyl(oxido){1-[6-(trifluoromethyl)pyridin-3-yl]cyclopropyl}$\lambda^4$-sulphanylidenecyanamide,
(I-16), methyl(oxido){1-(6-chloropyridin-3-yl)cyclopropyl}$\lambda^4$-sulphanylidenecyanamide.

If, in the context of the present invention, reference is now made to sulphoximines, these are generally sulphoximines of the general formula (I), where the general formula (I) includes in particular the compounds of groups (Ia) to (Ik), specifically the compounds of the general formulae (I-1) to (I-23).

According to the invention, "alkyl" represents straight-chain or branched aliphatic hydrocarbons having 1 to 6, preferably 1 to 4, carbon atoms. Suitable alkyl groups are, for example, methyl, ethyl, n-propyl, i-propyl, n-, iso-, sec- or tert-butyl, pentyl or hexyl. The alkyl group may be unsubstituted or is substituted by at least one of the substituents mentioned here.

According to the invention, "alkenyl" represents straight-chain or branched hydrocarbons having at least one double bond. The double bond of the alkenyl group may be unconjugated or is conjugated to an unsaturated bond or group. Alkenyl groups having 2 to 6 or 3 to 6 carbon atoms are preferred. Suitable alkenyl groups are, for example, vinyl or allyl. The alkenyl group may be unsubstituted or is substituted by at least one of the substituents mentioned here.

According to the invention, "alkynyl" represents straight-chain or branched hydrocarbons having at least one triple bond. The triple bond of the alkynyl group may be unconjugated or is conjugated to an unsaturated bond or group. Alkynyl groups having 2 to 6 or 3 to 6 carbon atoms are preferred. Suitable alkynyl groups are, for example, ethynyl, propynyl, butynyl, pentynyl, hexynyl, methylpropynyl, 4-methyl-1-butynyl, 4-propyl-2-pentynyl and 4-butyl-2-hexynyl. The alkynyl group may be unsubstituted or is substituted by at least one of the substituents mentioned here.

According to the invention, "cycloalkyl" represents cyclic hydrocarbons having 3 to 6 carbon atoms. Suitable cycloalkyl groups are, for example, cyclopropyl, cyclobutyl, cyclopentyl or cyclohexyl. The cycloalkyl group may be unsubstituted or is substituted by at least one of the substituents mentioned here.

According to the invention, "alkoxy" represents alkoxy groups having 1 to 6 carbon atoms, preferably having 1 to 4 carbon atoms. Suitable alkoxy groups are, for example, methyloxy, ethyloxy, n-propyloxy, i-propyloxy, n-, iso-, sec- or tert-butyloxy, pentyloxy or hexyloxy. The alkoxy group may be unsubstituted or is substituted by at least one of the substituents mentioned here.

According to the invention, "alkylamino" represents alkylamino groups having 1 to 6 carbon atoms, preferably 1 to 4 carbon atoms. Suitable alkylamino groups are, for example, methylamino, ethylamino, n-propylamino, i-propylamino, n-, iso-, sec- or tert-butylamino, pentylamino or hexylamino. The alkylamino group may be unsubstituted or is substituted by at least one of the substituents mentioned here.

According to the invention, "heterocyclic compounds" represents cyclic hydrocarbons having preferably 3 to 14, particularly preferably 3 to 10 and very particularly preferably 5 to 6 carbon atoms which contain at least one heteroatom, such as, for example, nitrogen, oxygen or sulphur and which can be prepared by customary methods. The heterocyclic compounds may contain saturated and unsaturated bonds or groups which are additionally in conjugation with further unsaturated bonds or groups. Suitable heterocyclic compounds are, for example, oxirane, aziridine, azetidine, tetrahydrofuran, dioxane, tetrahydrofuran-2-one, caprolactam; unsaturated heterocyclic compounds, such as, for example, 2H-pyrrole, 4H-pyran, 1,4-dihydropyridine; and heteroaryls, such as, for example, pyrrole, pyrazole, imidazole, oxazole, isoxazole, thiazole, oxathiazole, triazole, tetrazole, pyridine, pyridazine, pyrimidine, pyrazine, purine, pteridine, quinoline, isoquinoline, acridine and phenazine. The heterocyclic compounds may be unsubstituted or are substituted by at least one of the substituents mentioned here.

According to the invention, "halogen" represents fluorine, chlorine, bromine or iodine, preferably fluorine, chlorine or bromine.

According to the invention, "haloalkyl" represents alkyl groups having 1 to 6, preferably 1 to 4, carbon atoms in which at least one hydrogen atom has been replaced by a halogen. Suitable haloalkyl groups are, for example, $CH_2F$, $CHF_2$, $CF_3$, $CF_2Cl$, $CFCl_2$, $CCl_3$, $CF_2Br$, $CF_2CF_3$, $CFHCF_3$, $CH_2CF_3$, $CH_2CH_2F$, $CH_2CHF_2$, $CFCICF_3$, $CCl_2CF_3$, $CF_2CH_3$, $CF_2CH_2F$, $CF_2CHF_2$, $CF_2CF_2Cl$, $CF_2CF_2Br$, $CFHCH_3$, $CFHCHF_2$, $CHFCF_3$, $CHFCF_2Cl$, $CHFCF_2Br$, $CFCICF_3$, $CCl_2CF_3$, $CF_2CF_2CF_3$, $CH_2CH_2CH_2F$, $CH_2CHFCH_3$, $CH_2CF_2CF_3$, $CF_2CH_2CF_3$, $CF_2CF_2CH_3$, $CHFCF_2CF_3$, $CF_2CHFCF_3$, $CF_2CF_2CHF_2$, $CF_2CF_2CH_2F$, $CF_2CF_2CF_2Cl$, $CF_2CF_2CF_2Br$, 1,2,2,2-tetrafluoro-1-(trifluoromethyl)ethyl, 2,2,2-trifluoro-1-(trifluoromethyl)ethyl, pentafluoroethyl, 1-(difluoromethyl)-1,2,2,2-tetrafluoroethyl, 2-bromo-1,2,2-trifluoro-1-(trifluoromethyl)ethyl, 1-(difluoromethyl)-2,2,2-trifluoroethyl. The haloalkyl group may be unsubstituted or is substituted by at least one of the substituents mentioned here.

According to the invention, "aryl" represents aryl groups having 6 to 10, preferably 6, carbon atoms. Suitable aryl groups are, for example, phenyl or naphthyl. The aryl group may be unsubstituted or is substituted by at least one of the substituents mentioned here.

Preference is given to mixtures of two or more, preferably two or three, particularly preferably two, of the insecticidally active compounds.

According to the process according to the invention, genetically modified plants, in particular useful plants, are treated with compounds of the formula (I) to increase agricultural productivity. For the purposes of the invention, genetically modified plants are plants containing at least one gene or gene fragment not transferred by fertilization. This gene or gene fragment may originate or be derived from another plant of the same species, from plants of a different species, but also from organisms from the animal kingdom or microorganisms (including viruses) ("foreign gene") and/or, if appropriate, already have mutations compared to the natural sequence. According to the invention, it is also possible to use synthetic genes, which is also included in the term "foreign gene" here. It is also possible for a genetically modified plant to code for two or more foreign genes of different origin.

For the purposes of the invention, the "foreign gene" is further characterized in that it comprises a nucleic acid sequence which has a certain biological or chemical function or activity in the genetically modified plant. In general, these genes code for biocatalysts, such as, for example, enzymes or ribozymes, or else they comprise regulatory sequences, such as, for example, promoters or terminators, for influencing the expression of endogenous proteins (for example using antisense-technology, cosuppression technology or RNAi technology [RNA interference]). However, to this end, they may also code for regulatory proteins, such as, for example, repressors or inductors. Furthermore, the foreign gene may also serve for the targeted localization of a gene product of the genetically modified plant, coding, for example, for a signal sequence. The foreign gene may also code for inhibitors, such as, for example, antisense RNA.

The person skilled in the art is readily familiar with numerous different methods for producing genetically modified plants and methods for targeted mutagenesis, for gene transformation and cloning, for example from: Willmitzer, 1993, Transgenic plants, In: Biotechnology, A Multivolume Comprehensive Treatise, Rehm et al. (eds.), Vol. 2, 627-659, VCH Weinheim, Germany.

An example of a complex genetic manipulation of a useful plant is the so-called GURT technology ("Genetic Use Restriction Technologies") which allows technical control of the propagation of the genetically modified plant variety in question. To this end, in general two or three foreign genes are cloned into the useful plant which, in a complex interaction after administration of an external stimulus, trigger a cascade resulting in the death of the embryo which would otherwise develop. To this end, the external stimulus (for example an active compound or another chemical or abiotic stimulus) may interact, for example, with a repressor which then no longer suppresses the expression of a recombinase, so that the recombinase is able to cleave an inhibitor, thus allowing expression of a toxin causing the embryo to die. Examples of this type of genetically modified plants are disclosed in U.S. Pat. No. 5,723,765 or U.S. Pat. No. 5,808,034.

Accordingly, the person skilled in the art is familiar with processes for generating genetically modified plants which, by virtue of the integration of regulatory foreign genes and the overexpression, suppression or inhibition of endogenous genes or gene sequences mediated in this manner, if appropriate, or by virtue of the existence or expression of foreign genes or fragments thereof, have modified properties.

As already discussed above, the method according to the invention allows improved utilization of the production potential of genetically modified plants. On the one hand, this may, if appropriate, be based on the fact that the application rate of the active compound which can be employed according to the invention can be reduced, for example by lowering the dose employed or else by reducing the number of applications. On the other hand, if appropriate, the yield of the useful plants may be increased quantitatively and/or qualitatively. This is true in particular in the case of a transgenically generated resistance to biotic or abiotic stress. If, for example, compounds of the formula (I) are used, the dosage of the insecticide may in certain cases be limited to a sublethal dose, without this resulting in a significant weakening of the desired effect of the active compound on the pests.

Depending on the plant species or plant varieties, their location and the growth conditions (soils, climate, vegetation period, nutrients), these synergistic actions may vary and may be multifarious. Thus possible are, for example, reduced application rates and/or a widening of the activity spectrum and/or an increase of the activity of the compounds and compositions which can be used according to the invention, better plant growth, increased tolerance to high or low temperatures, increased tolerance to drought or to water or soil salt content, increased flowering, easier harvesting, accelerated maturation, higher harvest yields, higher quality and/or higher nutrient value of the harvested products, increased storability and/or processability of the harvested products, which exceed the effects normally to be expected.

These advantages are the result of a synergistic action, achieved according to the invention, between the compounds of the formula (I) which can be employed and the respective principle of action of the genetic modification of the genetically modified plant. This reduction of production means as a result of the synergism, with simultaneous yield or quality increase, is associated with considerable economical and ecological advantages.

A list of examples known to the person skilled in the art of genetically modified plants, with the respective affected structure in the plant or the protein expressed by the genetic modification in the plant being mentioned, is compiled in Table 1. Here, the structure in question or the principle expressed is in each case grouped with a certain feature in the sense of a tolerance to a certain stress factor. A similar list (Table 3) compiles—in a slightly different arrangement—likewise examples of principles of action, tolerances induced thereby and possible useful plants. Further examples of genetically modified plants suitable for the treatment according to the invention are compiled in Tables 4 to 6.

In an advantageous embodiment, the compounds of the formula (I) are used for treating genetically modified plants comprising at least one gene or gene fragment coding for a Bt toxin. A Bt toxin is a protein originating from or derived from the soil bacterium *Bacillus thuringiensis* which either belongs to the group of the crystal toxins (Cry) or the cytolytic toxins (Cyt). In the bacterium, they are originally formed as protoxins and only metabolized in alkaline medium—for example in the digestive tract of certain feed insects—to their active form. There, the active toxin then binds to certain hydrocarbon structures at cell surfaces causing pores to be formed which destroy the osmotic potential of the cell, which may effect cell lysis. The result is the death of the insects. Bt toxins are active in particular against certain harmful species from the orders of the Lepidoptera (butterflies), Homoptera, Diptera and Coleoptera (beetles) in all their development stages; i.e. from the egg larva via their juvenile forms to their adult forms.

It has been known for a long time that gene sequences coding for Bt toxins, parts thereof or else peptides or proteins derived from Bt toxins can be cloned with the aid of genetical engineering into agriculturally useful plants to generate genetically modified plants having endogenous resistance to pests sensitive to Bt toxins. For the purposes of the invention, the genetically modified plants coding for at least one Bt toxin or proteins derived therefrom are defined as "Bt plants".

The "first generation" of such Bt plants generally only comprise the genes enabling the formation of a certain toxin, thus only providing resistance to one group of pathogens. An example of a commercially available maize variety comprising the gene for forming the Cry1Ab toxin is "YieldGard®" from Monsanto which is resistant to the European corn borer. A known line of the "YieldGard®" maize from Monsanto is line MON 810. In contrast, in the Bt cotton variety ("Bollgard I®"), resistance to other pathogens from the family of the Lepidoptera is generated by introduction by cloning of the genes for forming the Cry1Ac toxin. "Bollgard II®" is a cotton variety which expresses the toxins Cry1Ac and Cry2Ab. Other genetically modified crop plants, in turn, express genes for forming Bt toxins with activity against pathogens from the order of the Coleoptera. Examples that may be mentioned are the Bt potato variety "NewLeaf" (Monsanto) capable of forming the Cry3A toxin, which is thus resistant to the Colorado potato beetle, and the genetically modified maize variety "YieldGard Rootworm®" (Monsanto) which forms the Cry3Bb1 toxin and is thus protected against various species of the Western corn rootworm. Further Bt toxins are the VIP proteins, for example VIP-3 with activity against pathogens from the orders of the Lepidoptera, Coleoptera and Diptera. An example of a cotton variety which expresses a VIP protein (Vip3A) together with Cry1Ab is "VIPCOT®" (Syngenta). Both proteins are highly active against two very common cotton pests, *Helicoverpa armigera* or *zea* (cotton bollworm) and *Heliothis virescens* (tobacco budworm).

In a "second generation", the multiply genetically modified plants, already described above, comprising or expressing at least two foreign genes were generated. An example of this is the genetically modified maize variety "YieldGard Plus®" (Monsanto), which forms the Cry1Ab and the Cry3Bb1 toxins.

Preference according to the invention is given to genetically modified plants with Bt toxins from the group of the Cry family (see, for example, Crickmore et al., 1998, Microbiol. Mol. Biol. Rev. 62: 807-812), which are particularly effective against Lepidoptera, Coleoptera and Diptera.

Examples of genes coding for the proteins are:
cry1Aa1, cry1Aa2, cry1Aa3, cry1Aa4, cry1Aa5, cry1Aa6, cry1Aa7, cry1Aa8, cry1Aa9, cry1Aa10, cry1Aa11 cry1Ab1, cry1Ab2, cry1Ab3, cry1Ab4, cry1Ab5, cry1Ab6, cry1Ab7, cry1Ab8, cry1Ab9, cry1Ab10, cry1Ab11, cry1Ab12, cry1Ab13, cry1Ab14, cry1Ac1, cry1Ac2, cry1Ac3, cry1Ac4, cry1Ac5, cry1Ac6, cry1Ac7, cry1Ac8, cry1Ac9, cry1Ac10, cry1Ac11, cry1Ac12, cry1Ac13, cry1Ad1, cry1Ad2, cry1Ae1, cry1Af1, cry1Ag1, cry1Ba1, cry1Ba2, cry1Bb1, cry1Bc1, cry1Bd1, cry1Be1, cry1Ca1, cry1Ca2, cry1Ca3, cry1Ca4, cry1Ca5, cry1Ca6, cry1Ca7, cry1Cb1, cry1Cb2, cry1Da1, cry1Da2, cry1Db1, cry1Ea1, cry1Ea2, cry1Ea3, cry1Ea4, cry1Ea5, cry1Ea6, cry1Eb1, cry1Fa1, cry1Fa2, cry1Fb1, cry1Fb2, cry1Fb3, cry1Fb4, cry1Ga1, cry1Ga2, cry1Gb1, cry1Gb2, cry1Ha1, cry1Hb1, cry1Ia1, cry1Ia2, cry1Ia3, cry1Ia4, cry1Ia5, cry1Ia6, cry1Ib1, cry1Ic1, cry1Id1, cry1Ie1, cry1I-like, cry1Ja1, cry1Jb1, cry1Jc1, cry1Ka1, cry1-like, cry2Aa1, cry2Aa2, cry2Aa3, cry2Aa4, cry2Aa5, cry2Aa6, cry2Aa7, cry2Aa8, cry2Aa9, cry2Ab1, cry2Ab2, cry2Ab3, cry2Ac1, cry2Ac2, cry2Ad1, cry3Aa1, cry3Aa2, cry3Aa3, cry3Aa4, cry3Aa5, cry3Aa6, cry3Aa7, cry3Ba1, cry3Ba2, cry3Bb1, cry3Bb2, cry3Bb3, cry3Ca1, cry4Aa1, cry4Aa2, cry4Ba1, cry4Ba2, cry4Ba3, cry4Ba4, cry5Aa1, cry5Ab1, cry5Ac1, cry5Ba1, cry6Aa1, cry6Ba1, cry7Aa1, cry7Ab1, cry7Ab2, cry8Aa1, cry8Ba1, cry8Ca1, cry9Aa1, cry9Aa2, cry9Ba1, cry9Ca1, cry9Da1, cry9Da2, cry9Ea1, cry9 like, cry10Aa1, cry10Aa2, cry11Aa1, cry11Aa2, cry11Ba1, cry11Bb1, cry12Aa1, cry13Aa1, cry14Aa1, cry15Aa1, cry16Aa1, cry17Aa1, cry18Aa1, cry18Ba1, cry18Ca1, cry19Aa1, cry19Ba1, cry20Aa1, cry21Aa1, cry21Aa2, cry22Aa1, cry23Aa1, cry24Aa1, cry25Aa1, cry26Aa1, cry27Aa1, cry28Aa1, cry28Aa2, cry29Aa1, cry30Aa1, cry31Aa1, cytlAa1, cytlAa2, cytlAa3, cytlAa4, cytlAb1, cytlBa1, cyt2Aa1, cyt2Ba1, cyt2Ba2, cyt2Ba3, cyt2Ba4, cyt2Ba5, cyt2Ba6, cyt2Ba7, cyt2Ba8, cyt2Bb1.

Particular preference is given to the genes or gene sections of the subfamilies cry1, cry2, cry3, cry5 and cry9; especially preferred are cry1Ab, cry1Ac, cry3A, cry3B and cry9C.

Furthermore, it is preferred to use plants which, in addition to the genes for one or more Bt toxins, contain or express, if appropriate, also genes for expressing, for example, a protease or peptidase inhibitor (such as in WO-A 95/35031), of herbicide resistances (for example to glufosinate or glyphosate by expression of the pat gene or bar gene) or for becoming resistant to nematodes, fungi or viruses (for example by expressing a glucanase, chitinase). However, they may also be modified in their metabolic properties, so that they show a qualitative and/or quantitative change of ingredients (for example by modification of the energy, carbohydrate, fatty acid or nitrogen metabolism or of metabolite currents influencing these) (see above). An example of a maize cultivar which expresses the Cry1Fa2 toxin and the enzyme phosphinothricin N-acetyltransferase (PAT, provision of herbicide resistance to glufosinate ammonium) is "Herculex I®" (Pioneer/Dow AgroSciences). A maize cultivar which expresses a truncated Cry1Ab toxin and the enzyme PAT is Bt11 maize from Syngenta. Bt176 maize from Syngenta expresses a Cry1Ab toxin and the enzyme PAT.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:
1) an insecticidal crystal protein from *Bacillus thuringiensis* or an insecticidal portion thereof, such as the insecticidal crystal proteins listed by Crickmore et al., Microbiology and Molecular Biology Reviews (1998) 62, 62, 807-813, updated by Crickmore et al. (2005) in the *Bacillus thuringiensis* toxin nomenclature, online at: www.lifesci.sussex.ac.uk/Home/Neil_Crickmore/Bt, or insecticidal portions thereof, for example proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or
4) a protein of any one of 1) to 3) above wherein some, particularly 1 to 10, amino acids have been replaced by another amino acid to obtain a higher insecticidal activity against a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604; or
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity against a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay the development of insect resistance to the plants, by using different proteins insecticidal to the same target insect species but having a different mode of action, such as binding to different receptor binding sites in the insect.

A list of examples of principles of action which can be introduced by genetic modification into a useful plant and which are suitable for the treatment according to the invention on their own or in combination is compiled in Table 2. Under the header "AP" (active principle), this table contains the respective principle of action and associated therewith the pest to be controlled.

In a particularly preferred variant, the process according to the invention is used for treating genetically modified vegetable, maize, soya bean, cotton, tobacco, rice, potato and sugar beet varieties. These are preferably Bt plants.

The vegetable plants or varieties are, for example, the following useful plants:
potatoes: preferably starch potatoes, sweet potatoes and table potatoes;
root vegetables: preferably carrots, turnips (swedes, stubble turnips (*Brassica rapa* var. *rapa*), spring turnips, autumn turnips (*Brassica campestris* ssp. *rapifera*)), *Brassica rapa* L. ssp. *rapa* f. *teltowiensis*), scorzonera, Jerusalem artichoke, turnip-rooted parsley, parsnip, radish and horseradish;
tuber vegetables: preferably kohlrabi, beetroot, celeriac, garden radish;
bulb crops: preferably scallion, leek and onions (planting onions and seed onions);
*brassica* vegetables: preferably headed cabbage (white cabbage, red cabbage, kale, savoy cabbage), cauliflower, broccoli, curly kale, marrow-stem kale, seakale and Brussels sprouts;
fruiting vegetables: preferably tomatoes (outdoor tomatoes, vine-ripened tomatoes, beef tomatoes, greenhouse tomatoes, cocktail tomatoes, industrial and fresh market tomatoes), melons, eggplants, aubergines, pepper (sweet pepper and hot pepper, Spanish pepper), chilli pepper, pumpkins, courgettes and cucumbers (outdoor cucumbers, greenhouse cucumbers, snake gourds and gherkins);

vegetable pulses: preferably bush beans (as sword beans, string beans, flageolet beans, wax beans, corn beans of green- and yellow-podded cultivars), pole beans (as sword beans, string beans, flageolet beans, wax beans of green-, blue- and yellow-podded cultivars), broad-beans (field beans, Windsor beans, cultivars having white- and black-spotted flowers), peas (chickling vetch, chickpeas, marrow peas, shelling peas, sugar peas, smooth peas, cultivars having light- and dark-green fresh fruits) and lentils;

green vegetables and stem vegetables: preferably Chinese cabbage, round-headed garden lettuce, curled lettuce, lamb's-lettuce, iceberg lettuce, romaine lettuce, oakleaf lettuce, endives, radicchio, lollo rossa, ruccola lettuce, chicory, spinach, chard (leaf chard and stem chard) and parsley;

other vegetables: preferably asparagus, rhubarb, chives, artichokes, mint varieties, sunflowers, Florence fennel, dill, garden cress, mustard, poppy seed, peanuts, sesame and salad chicory.

Bt vegetables including exemplary methods for preparing them are described in detail, for example, in Barton et al., 1987, Plant Physiol. 85: 1103-1109; Vaeck et al., 1987, Nature 328: 33-37; Fischhoff et al., 1987, Bio/Technology 5: 807-813. In addition, Bt vegetable plants are already known as commercially available varieties, for example the potato cultivar NewLeaf (Monsanto). The preparation of Bt vegetables is also described in U.S. Pat. No. 6,072,105.

Likewise, Bt cotton is already known in principle, for example from U.S. Pat. No. 5,322,938. In the context of the present invention, particular preference is given to the Bt cotton with the trade names NuCOTN33® and NuCOTN33B® (expression of the Cry1Ac toxin).

The use and preparation of Bt maize has likewise already been known for a long time, for example from Ishida, Y., Saito, H., Ohta, S., Hiei, Y., Komari, T., and Kumashiro, T. (1996). High efficiency transformation of maize (*Zea mayz* L.) mediated by *Agrobacterium tumefaciens*, Nature Biotechnology 4: 745-750. EP-B-0485506, too, describes the preparation of Bt maize plants. Furthermore, different varieties of Bt maize are commercially available, for example under the following trade names (company/companies is/are in each case given in brackets): KnockOut® (Novartis Seeds, expression of the Cry1Ab toxin), NaturGard® (Mycogen Seeds, expression of the Cry1Ab toxin), Yieldgard® (Novartis Seeds, Monsanto, Cargill, Golden Harvest, Pioneer, DeKalb, inter alia, expression of the Cry1Ab toxin), Bt-Xtra® (DeKalb, expression of the Cry1Ac toxin), StarLink® (Aventis CropScience, Garst inter alia, expression of the Cry9c toxin), Herculex 1 (Mycogen, Pioneer, expression of the Cry1F toxin). For the purposes of the present invention, particular preference is given especially to the following maize cultivars: KnockOut®, NaturGard®, Yieldgard®, Bt-Xtra® and StarLink®.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (92), 7, 139-145), the genes encoding a *petunia* EPSPS (Shah et al., Science (1986), 233, 478-481), a tomato EPSPS (Gasser et al., J. Biol. Chem. (1988), 263, 4280-4289) or an *Eleusine* EPSPS (WO 2001/66704). It can also be a mutated EPSPS, as described, for example, in EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described, for example, in WO 2002/036782, WO 2003/092360, WO 2005/012515 and WO 2007/024782. Glyphosate-tolerant plants can also be obtained by selecting plants containing naturally occurring mutations of the above-mentioned genes as described, for example, in WO 2001/024615 or WO 2003/013226.

Other herbicide-resistant plants are for example plants have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase have been described, for example, in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme according to WO 96/038567, WO 99/024585 and WO 99/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 99/034008 and WO 2002/36787. Tolerance of plants to HPPD inhibitors can also be improved by transforming plants with a gene encoding an prephenate dehydrogenase enzyme in addition to a gene encoding an HPPD-tolerant enzyme, as described in WO 2004/024928.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyloxy(thio) benzoates, and/or sulphonylaminocarbonyltriazolinone herbicides. Different mutations in the ALS enzyme (also known as acetohydroxy acid synthase, AHAS) are known to impart tolerance to different herbicides and groups of herbicides, as described, for example, in Tranel and Wright, Weed Science (2002), 50, 700-712, and also in U.S. Pat. No. 5,605,011, U.S. Pat. No. 5,378,824, U.S. Pat. No. 5,141,870 and U.S. Pat. No. 5,013,659. The production of sulphonylurea-tolerant plants and imidazolinone-tolerant plants has been described in U.S. Pat. No. 5,605,011; U.S. Pat. No. 5,013, 659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and also in the international publication WO 96/033270. Further imidazolinone-tolerant plants have also been described, for example in WO 2004/040012, WO 2004/106529, WO 2005/020673, WO 2005/093093, WO 2006/007373, WO 2006/015376, WO 2006/024351 and WO 2006/060634. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding, as described, for example, for soya beans in U.S. Pat. No. 5,084,082, for rice in WO 97/41218, for sugar beet in U.S. Pat. No. 5,773,702 and WO 99/057965, for lettuce in U.S. Pat. No. 5,198,599 or for sunflower in WO 2001/065922.

For soya beans, too, Roundup®Ready varieties or varieties having resistance to the herbicide Liberty Link® can be obtained and treated according to the invention. In the case of rice, a large number of "Golden Rice" lines are available which are likewise characterized in that, by virtue of a genetic modification, they have an increased content of provitamin A. These too are examples of plants which can be treated by the process according to the invention, with the advantages indicated.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose) polymerase (PARP) gene in the plant cells or plants, as described in WO 2000/004173 or EP 04077984.5 or EP 06009836.5.
b. plants which contain a stress tolerance-enhancing transgene capable of reducing the expression and/or the activity of the PARG encoding genes of the plants or plant cells, as described, for example, in WO 2004/090140;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase, as described, for example, in EP 04077624.7 or WO 2006/133827 or PCT/EP07/002433.

Plants or plant varieties (obtained by plant biotechnology methods such as genetic engineering) which may also be treated according to the invention show altered quantity, quality and/or storage-stability of the harvested product and/or altered properties of specific ingredients of the harvested product such as, for example:
1) Transgenic plants synthesizing a modified starch which, with respect to their physicochemical properties, in particular the amylose content or the amylose/amylopectin ratio, the degree of branching, the average chain length, the distribution of the side chains, the viscosity behaviour, the gel strength, the starch grain size and/or the starch grain morphology, are modified compared to the starch synthesized in wild-type plant celle or plants, such that the starch synthesized is more suitable for certain applications. These transgenic plants synthesizing a modified starch are described, for example, in EP 0571427, WO 95/004826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/975, WO 95/26407, WO 96/34968, WO 98/20145, WO 99/12950, WO 99/66050, WO 99/53072, U.S. Pat. No. 6,734,341, WO 2000/11192, WO 98/22604, WO 98/32326, WO 2001/98509, WO 2001/98509, WO 2005/002359, U.S. Pat. No. 5,824,790, U.S. Pat. No. 6,013,861, WO 94/004693, WO 94/009144, WO 94/11520, WO 95/35026 and WO 97/20936.
2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan types, as described in EP 0663956, WO 96/001904, WO 96/021023, WO 98/039460 and WO 99/024593, plants which produce alpha-1,4-glucans, as described in WO 95/031553, US 2002/031826, U.S. Pat. No. 6,284,479, U.S. Pat. No. 5,712,107, WO 97/047806, WO 97/047807, WO 97/047808 and WO 2000/14249, plants which produce alpha-1,6-branched alpha-1,4-glucans, as described in WO 2000/73422, and plants which produce alternan, as described in WO 2000/047727, EP 06077301.7, U.S. Pat. No. 5,908,975 and EP 0728213.
3) transgenic plants which produce hyaluronan, as described, for example, in WO 2006/032538, WO 2007/039314, WO 2007/039315, WO 2007/039316, JP 2006/304779 and WO 2005/012529.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, which contain an altered form of cellulose synthase genes, as described in WO 98/000549,
b) plants, such as cotton plants, which contain an altered form of rsw2 or rsw3 homologous nucleic acids, as described in WO 2004/053219;
c) plants, such as cotton plants, with an increased expression of sucrose phosphate synthase, as described in WO 2001/017333;

d) plants, such as cotton plants, with an increased expression of sucrose synthase, as described in WO 2002/45485;
e) plants, such as cotton plants, wherein the timing of the plasmodesmatal gating at the basis of the fibre cell is altered, for example through downregulation of fibre-selective (3-1,3-glucanase, as described in WO 2005/017157;
f) plants, such as cotton plants, which have fibres with altered reactivity, for example through the expression of the N-acetylglucosaminetransferase gene including nodC and chitin synthase genes, as described in WO 2006/136351.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content, as described, for example, in U.S. Pat. No. 5,969,169, U.S. Pat. No. 5,840,946 or U.S. Pat. No. 6,323,392 or U.S. Pat. No. 6,063,947;
b) plants, such as oilseed rape plants, which produce oil having a low linolenic acid content, as described in U.S. Pat. No. 6,270,828, U.S. Pat. No. 6,169,190 or U.S. Pat. No. 5,965,755.
c) plants, such as oilseed rape plants, which produce oil having a low level of saturated fatty acids, as described, for example, in U.S. Pat. No. 5,434,283.

Particularly useful transgenic plants which may be treated according to the invention are plants containing transformation events, or a combination of transformation events, that are listed for example in the databases of various national or regional regulatory agencies (see for example, gmoinfo.jrc.it/gmp_browse.aspx and www.agbios.com/dbase.php)

The method according to the invention is suitable for controlling a large number of harmful organisms which occur in particular in vegetables, maize and cotton, in particular insects and arachnids, very particularly preferably insects. The pests mentioned include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro*, *Aceria sheldoni*, *Aculops* spp., *Aculus* spp., *Amblyomma* spp., *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Hemitarsonemus* spp., *Hyalomma* spp., *Ixodes* spp., *Latrodectus mactans*, *Metatetranychus* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus carpophagus* and *Scutigera* spp.

From the order of the Coleoptera, for example, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apogonia* spp., *Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnosterna consanguinea*, *Leptinotarsa decemlineata*, *Lissorhoptrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lumbricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichiura*, *Wuchereria bancrofti*.

It is furthermore possible to control Protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oeb-

*alus* spp., Pentomidae, *Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare, Oniscus asellus, Porcellio scaber*.

From the order of the Isoptera, for example, *Reticulitermes* spp. and *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp. and *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni* and *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

The method according to the invention is particularly suitable for treating Bt vegetables, Bt maize, Bt cotton, Bt soya beans, Bt tobacco and also Bt rice, Bt sugar beet or Bt potatoes for controlling aphids (Aphidina), whiteflies (Trialeurodes), thrips (Thysanoptera), spider mites (Arachnida), scale insects and mealy-bugs (Coccoidae and Pseudococcoidae).

The active compounds which can be used according to the invention can be employed in customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, that is, liquid solvents, and/or solid carriers, optionally with the use of surfactants, that is to say emulsifiers and/or dispersants, and/or foam-formers. The formulations are prepared either in suitable plants or else before or during application.

Wettable powders are preparations which can be dispersed homogeneously in water and which, in addition to the active compound and beside a diluent or inert substance, also comprise wetting agents, for example polyethoxylated alkylphenols, polyethoxylated fatty alcohols, alkylsulphonates or alkylphenylsulphonates and dispersants, for example sodium lignosulphonate, sodium 2,2'-dinaphthylmethane-6,6'-disulphonate.

Dusts are obtained by grinding the active compound with finely distributed solid substances, for example talc, natural clays, such as kaolin, bentonite, pyrophillite or diatomaceous earth. Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Suitable for use as auxiliaries are substances which are suitable for imparting to the composition itself and/or to preparations derived therefrom (for example spray liquors, seed dressings) particular properties such as certain technical properties and/or also particular biological properties. Typical auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts.

Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

These individual types of formulation are known in principle and are described, for example, in: "Pesticides Formulations", 2nd Ed., Marcel Dekker N.Y.; Martens, 1979, "Spray Drying Handbook", 3rd Ed., G. Goodwin Ltd. London.

Based on his general expert knowledge, the person skilled in the art is able to choose suitable formulation auxiliaries (in this context, see, for example, Watkins, "Handbook of Insecticide Dust Diluents and Carriers", 2nd Ed., Darland Books, Caldwell N.J.).

In a preferred embodiment, the plants or plant parts are treated according to the invention with an oil-based suspension concentrate. An advantageous suspension concentrate is known from WO 2005/084435 (EP 1 725 104 A2). It consists of at least one room-temperature-solid active agrochemical substance, at least one "closed" penetrant, at least one vegetable oil or mineral oil, at least one nonionic surfactant and/or at least one anionic surfactant, and optionally one or more additives from the groups of the emulsifiers, foam inhibitors, preservatives, antioxidants, colorants and/or inert filler materials. Preferred embodiments of the suspension concentrate are described in the abovementioned WO 2005/084435. For the purpose of disclosure, both documents are incorporated herein in their entirety.

In a further preferred embodiment, the genetically modified plants or plant parts are treated according to the invention with compositions comprising ammonium or phosphonium salts and, if appropriate, penetrants. Advantageous compositions are known from WO 2007/068355. They consist of at least one compound of the formula (I) and at least one ammonium or phosphonium salt and, if appropriate, penetrants. Preferred embodiments are described in WO 2007/068355. For the purpose of disclosure, this document is incorporated herein in its entirety.

In general, the formulations comprise from 0.01 to 98% by weight of active compound, preferably from 0.5 to 90%. In wettable powders, the active compound concentration is, for example, from about 10 to 90% by weight, the remainder to 100% by weight consisting of customary formulation components. In the case of emulsifiable concentrates, the active compound concentration can be from about 5 to 80% by weight. In most cases, formulations in the form of dusts comprise from 5 to 20% by weight of active compound, sprayable solutions comprise about 2 to 20% by weight. In the case of granules, the active compound content depends partially on whether the active compound is present in liquid or solid form and on which granulation auxiliaries, fillers, etc., are used.

The required application rate may also vary with external conditions such as, inter alia, temperature and humidity. It may vary within wide limits, for example between 0.1 g/ha and 5.0 kg/ha or more of active substance. However, it is preferably between 0.1 g/ha and 1.0 kg/ha. Owing to the synergistic effects between Bt vegetable and insecticide, particular preference is given to application rates of from 0.1 to 500 g/ha.

For compounds of the formula (I), preference is given to application rates of from 10 to 500 g/ha, particular preference is given to 10 to 200 g/ha.

In a particular embodiment of the method according to the invention, the compound of the formula (I) is employed in an application rate of from 0.1 g/ha to 5.0 kg/ha, preferably from 0.1 to 500 g/ha and particularly preferably from 50 to 500 g/ha and especially preferably from 50 to 200 g/ha.

In their commercial formulations and in the use forms prepared from these formulations, the active compounds according to the invention may be present as mixtures with other active compounds, such as insecticides, attractants, sterilants, acaricides, nematicides, fungicides, growth-regulating substances or herbicides.

Particularly favourable examples of co-components in mixtures are the following compounds:

Fungicides:

Inhibitors of Nucleic Acid Synthesis benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid Inhibitors of Mitosis and Cell Division benomyl, carbendazim, diethofencarb, fuberidazole, pencycuron, thiabendazole, thiophanat-methyl, zoxamide Inhibitors of Respiratory Chain Complex I/II diflumetorim bixafen, boscalid, carboxin, fenfuram, fluopyram, flutolanil, furametpyr, mepronil, oxycarboxin, penthiopyrad, thifluzamide, N-[2-(1,3-dimethylbutyl)phenyl]-5-fluoro-1,3-dimethyl-1H-pyrazole-4-carboxamide Inhibitors of Respiratory Chain Complex III amisulbrom, azoxystrobin, cyazofamid, dimoxystrobin, enestrobin, famoxadone, fenamidone, fluoxastrobin, kresoxim-methyl, metominostrobin, orysastrobin, pyraclostrobin, pyribencarb, picoxystrobin, trifloxystrobin Decouplers dinocap, fluazinam Inhibitors of ATP Production fentin acetate, fentin chloride, fentin hydroxide, silthiofam Inhibitors of Amino Acid Biosynthesis and Protein Biosynthesis andoprim, blasticidin-S, cyprodinil, kasugamycin, kasugamycin hydrochloride hydrate, mepanipyrim, pyrimethanil Inhibitors of Signal Transduction fenpiclonil, fludioxonil, quinoxyfen Inhibitors of Lipid and Membrane Synthesis chlozolinate, iprodione, procymidone, vinclozolin ampropylfos, potassium-ampropylfos, edifenphos, iprobenfos (IBP), isoprothiolane, pyrazophos tolclofos-methyl, biphenyl iodocarb, propamocarb, propamocarb hydrochloride Inhibitors of Ergosterol Biosynthesis fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, spiroxamine, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine Inhibitors of Cell Wall Synthesis benthiavalicarb, bialaphos, dimethomorph, flumorph, iprovalicarb, polyoxins, polyoxorim, validamycin A Inhibitors of Melanin Biosynthesis capropamid, diclocymet, fenoxanil, phthalid, pyroquilon, tricyclazole Resistance Induction acibenzolar-S-methyl, probenazole, tiadinil Multisite captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulfamide, fluopicolid, fluoroimid, fosetyl-Al, hexachlorobenzene, 8-hydroxyquinoline sulphate, iprodione, irumamycin, isotianil, methasulfocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzenesulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3(trifluoromethyl)phenyl] ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio] methyl]-.alpha.-(methoxymethylene)benzacetate, 4-chloro-alpha-propynyloxy-N-[2-[3-methoxy-4-(2-propynyloxy) phenyl]ethyl]benzacetamide, (2S)—N-[2-[4-[[3-(4-chlorophenyl)-2-propynyl]oxy]-3-methoxyphenyl]ethyl]-3-methyl-2-[(methylsulphonyl)amino]butanamide, 5-chloro-7-(4-methylpiperidin-1-yl)-6-(2,4,6-trifluorophenyl) [1,2,4] triazolo[1,5-a]pyrimidine, 5-chloro-6-(2,4,6-trifluorophenyl)-N-[(1R)-1,2,2-trimethylpropyl][1,2,4] triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N—{(Z)-[(cyclopropylmethoxy)imino][6-(difluoromethoxy)-2,3-difluorophenyl]methyl}-2-benzacetamide, N-(3-ethyl-3,5,5- trimethylcyclohexyl)-3-formylamino-2-hydroxybenzamide, 2-[[[[1-[3-(1-fluoro-2-phenyl-ethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
Acetylcholine Esterase (AChE) Inhibitors
carbamates,
for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, fenoxycarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
organophosphates,
for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion
Sodium Channel Modulators/Voltage-Dependent Sodium Channel Blockers
pyrethroids,
for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocytrin, cycloprothrin, cyfluthrin, cyhalothrin, cypermethrin (alpha-, beta-, theta-, zeta-), cyphenothrin, deltamethrin, eflusilanate, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, pyrethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)
DDT
oxadiazines,
for example indoxacarb
semicarbazones,
for example metaflumizone (BAS3201)
Acetylcholine Receptor Agonists/Antagonists
chloronicotinyls,
for example acetamiprid, AKD 1022, clothianidin, dinotefuran, imidacloprid, imidaclothiz, nitenpyram, nithiazine, thiacloprid, thiamethoxam
nicotine, bensultap, cartap
Acetylcholine Receptor Modulators
spinosyns,
for example spinosad, spinetoram
GABA-Controlled Chloride Channel Antagonists
organochlorines,
for example camphechlor, chlordane, endosulphan, gamma-HCH, HCH, heptachlor, lindane, methoxychlor
fiprols,
for example acetoprole, ethiprole, fipronil, pyrafluprole, pyriprole, vaniliprole
Chloride Channel Activators
mectins,
for example abarmectin, emamectin, emamectin-benzoate, ivermectin, lepimectin, milbemycin
Juvenile hormone mimetics,
for example diofenolan, epofenonane, fenoxycarb, hydroprene, kinoprene, methoprene, pyriproxifen, triprene
Ecdysone Agonists/Disruptors
diacylhydrazines,
for example chromafenozide, halofenozide, methoxyfenozide, tebufenozide
Chitin Biosynthesis Inhibitors
benzoylureas, for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron
 buprofezin
 cyromazine
Oxidative Phosphorylation Inhibitors, ATP Disruptors
 diafenthiuron
  organotin compounds, for example azocyclotin, cyhexatin, fenbutatin-oxide
Oxidative Phosphorylation Decouplers Acting by Interrupting the H-Proton Gradient
pyrroles, for example chlorfenapyr
dinitrophenols, for example binapacyrl, dinobuton, dinocap, DNOC, meptyldinocap
Site-I Electron Transport Inhibitors
METIs, for example fenazaquin, fenpyroximate, pyrimidifen, pyridaben, tebufenpyrad, tolfenpyrad
hydramethylnon
dicofol
Site-II Electron Transport Inhibitors
rotenone
Site-III Electron Transport Inhibitors
acequinocyl, fluacrypyrim
Microbial Disruptors of the Insect Gut Membrane
*Bacillus thuringiensis* strains
Lipid Synthesis Inhibitors
tetronic acids, for example spirodiclofen, spiromesifen
tetramic acids,
for example spirotetramate, cis-3-(2,5-dimethylphenyl)-4-hydroxy-8-methoxy-1-azaspiro[4.5]dec-3-en-2-one
carboxamides,
for example flonicamid
octopaminergic agonists,
for example amitraz
Inhibitors of Magnesium-Stimulated ATPase,
  propargite
  nereistoxin analogues,
    for example thiocyclam hydrogen oxalate, thiosultap-sodium
Ryanodin Receptor Agonists
benzoic acid dicarboxamides,
for example flubendiamide
anthranilamides,
for example Rynaxypyr (3-bromo-N-{4-chloro-2-methyl-6-[(methylamino)carbonyl]phenyl}-1-(3-chloropyridin-2-yl)-1H-pyrazole-5-carboxamide), Cyazapyr (ISO-proposed) (3-bromo-N-{4-cyano-2-methyl-6-[(methylamino)carbonyl]phenyl}-1-(3-chloropyridin-2-yl)-1H-pyrazole-5-carboxamide) (known from WO 2004067528)
Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.
Active Compounds with Unknown or Unspecific Mechanisms of Action
4-{[(6-bromopyrid-3-yl)methyl](2-fluoroethyl)amino}furan-2(5H)-one (known from WO 2007/115644),
4-{[(6-fluoropyrid-3-yl)methyl](2,2-difluoroethyl)amino}furan-2(5H)-one (known from WO 2007/115644),
4-{[(2-chloro-1,3-thiazol-5-yl)methyl](2-fluoroethyl)amino}furan-2(5H)-one (known from WO 2007/115644),
4-{[(6-chloropyrid-3-yl)methyl](2-fluoroethyl)amino}furan-2(5H)-one (known from WO 2007/115644),
4-{[(6-chloropyrid-3-yl)methyl](2,2-difluoroethyl)amino}furan-2(5H)-one (known from WO 2007/115644),
4-{[(6-chloro-5-fluoropyrid-3-yl)methyl](methyl)amino}furan-2(5H)-one (known from WO 2007/115643),
4-{[(5,6-dichloropyrid-3-yl)methyl](2-fluoroethyl)amino}furan-2(5H)-one (known from WO 2007/115646),
4-{[(6-chloro-5-fluoropyrid-3-yl)methyl](cyclopropyl)amino}furan-2(5H)-one (known from WO 2007/115643),
4-{[(6-chloropyrid-3-yl)methyl](cyclopropyl)amino}furan-2(5H)-one (known from EP-A-0 539 588) and 4-{[(6-chloropyrid-3-yl)methyl](methyl)amino}furan-2(5H)-one (known from EP-A-0 539 588).
fumigants, for example aluminium phosphide, methyl bromide, sulphuryl fluoride
antifeedants,
for example cryolite, pymetrozine, pyrifluquinazon
mite growth inhibitors,
for example clofentezine, etoxazole, hexythiazox
amidoflumet, benclothiaz, benzoximate, bifenazate, bromopropylate, buprofezin, chinomethionat, chlordimeform, chlorobenzilate, chloropicrin, clothiazoben, cyclopene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin or cyflumetofen, cyanopyrafen.

A mixture with other known active compounds, such as herbicides, fertilizers, growth regulators, safeners, semiochemicals, or else with agents for improving the plant properties, is also possible.

The active compound content of the use forms prepared from the commercially available formulations can be from 0.00000001 to 95% by weight, preferably between 0.00001 and 1% by weight, of active compound.

TABLE 1

| Plant: maize | |
|---|---|
| Structure affected or principle expressed | Feature of the plant/tolerance to |
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acid, cyclohexanedione |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylates, oxadiazoles etc. |
| cytochrome P450 e.g. P450 SU1 | xenobiotics and herbicides, such as sulphonylurea |
| dimboa biosynthesis (Bx1-Gen) | *Helminthosporium turcicum, Rhopalosiphum maydis, Diplodia maydis, Ostrinia nubilalis*, Lepidoptera sp. |
| CMIII (small basic peptide building block from maize grain) | plant pathogens e.g. *Fusarium, Alternaria*, Sclerotina |
| Com-SAFP (zeamatin) | plant pathogens, e.g. *Fusarium, Alternaria*, Sclerotina, *Rhizoctonia, Chaetomium*, Phycomycen |
| Hm1-gene | *Cochliobulus* |
| chitinases | plant pathogens |
| glucanases | plant pathogens |
| envelope proteins | viruses, such as the Maize dwarf mosaic virus (MDMV) |
| toxins of *Bacillus thuringiensis*, VIP 3, *Bacillus cereus* toxin, *Photorabdus* and *Xenorhabdus* toxins | Lepidoptera, Coleoptera, Diptera, nematodes, e.g. *Ostrinia nubilalis, Heliothis zea*, armyworms e.g. *Spodoptera frugiperda*, Western corn rootworm, *Sesamia* sp., Aprotis ipsilon, Asian corn borer, weevils |
| 3-hydroxysteroid oxidase | Lepidoptera, Coleoptera, Diptera, nematodes, e.g. *Ostrinia nubilalis, Heliothis zea*, armyworms e.g. *Spodoptera frugiperda*, Western corn rootworm, *Sesamia* sp., Aprotis ipsilon, Asian corn borer, weevils |
| peroxidase | Lepidoptera, Coleoptera, Diptera, nematodes, e.g. *Ostrinia nubilalis, Heliothis zea*, armyworms e.g. *Spodoptera frugiperda*, Western corn rootworm, *Sesamia* sp., Aprotis ipsilon, Asian corn borer, weevils |
| aminopeptidase inhibitors, e.g. leucine aminopeptidase inhibitors (LAPI) | Lepidoptera, Coleoptera, Diptera, nematodes, e.g. *Ostrinia nubilalis, Heliothis zea*, armyworms e.g. *Spodoptera frugiperda*, Western corn rootworm, *Sesamia* sp., Aprotis ipsilon, Asian corn borer, weevils |

TABLE 1-continued

| Structure affected/protein expressed | Feature of the plant/tolerance to |
|---|---|
| limonene synthase | Western corn rootworm |
| lectin | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., Aprotis ipsilon, Asian corn borer, weevils |
| protease inhibitors e.g. cystatin, patatin, virgiferin, CPTI | weevils, Western corn rootworm |
| ribosome-inactivating protein | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., Aprotis ipsilon, Asian corn borer, weevils |
| 5C9-maize polypeptide | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., Aprotis ipsilon, Asian corn borer, weevils |
| HMG-CoA reductase | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., Aprotis ipsilon, Asian corn borer, weevils |

Plant: Wheat

| Structure affected/protein expressed | Feature of the plant/tolerance to |
|---|---|
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acid, cyclohexanedione |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 | xenobiotics and herbicides, such as sulphonylurea compounds |
| antifungal polypeptide AlyAFP | plant pathogens, e.g. *Septoria* and *Fusarium* |
| glucose oxidase | plant pathogens, e.g. *Fusarium*, *Septoria* |
| pyrrolnitrin synthesis gene | plant pathogens, e.g. *Fusarium*, *Septoria* |
| serine/threonine kinases | plant pathogens, e.g. *Fusarium*, *Septoria* and other diseases |
| polypeptide having the effect of triggering a hypersensitivity reaction | plant pathogens, e.g. *Fusarium*, *Septoria* and other diseases |
| systemic aquired resistance (SAR) genes | viral, bacterial, fungal and nematodal pathogens |
| chitinases | plant pathogens |
| glucanases | plant pathogens |
| double-strand ribonuclease | viruses such as, for example, BYDV and MSMV |
| envelope proteins | viruses such as, for example, BYDV and MSMV |
| toxins of *Bacillus thuringiensis*, VIP 3, *Bacillus cereus* toxins, *Photorabdus* and *Xenorhabdus* toxins | Lepidoptera, Coleoptera, Diptera, nematodes |
| 3-hydroxysteroid oxidase | Lepidoptera, Coleoptera, Diptera, nematodes |
| peroxidase | Lepidoptera, Coleoptera, Diptera, nematodes |
| aminopeptidase inhibitors, e.g. leucine aminopeptidase inhibitor | Lepidoptera, Coleoptera, Diptera, nematodes |
| lectins | Lepidoptera, Coleoptera, Diptera, nematodes, aphids |
| protease inhibitors, e.g. cystatin, patatin, virgiferin, CPTI | Lepidoptera, Coleoptera, Diptera, nematodes, aphids |
| ribosome-inactivating protein | Lepidoptera, Coleoptera, Diptera, nematodes, aphids |
| HMG-CoA reductase | Lepidoptera, Coleoptera, Diptera, nematodes, e.g. *Ostrinia nubilalis*, *Heliothis zea*, armyworms e.g. *Spodoptera frugiperda*, Western corn rootworm, *Sesamia* sp., Aprotis ipsilon, Asian corn borer, weevils |

Plant: Barley

| Structure affected/protein expressed | Feature of the plant/tolerance to |
|---|---|
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 | xenobiotics and herbicides, such as sulphonylurea compounds |
| antifungal polypeptide AlyAFP | plant pathogens, e.g. *Septoria* and *Fusarium* |
| glucose oxidase | plant pathogens, e.g. *Fusarium*, *Septoria* |
| pyrrolnitrin synthesis gene | plant pathogens, e.g. *Fusarium*, *Septoria* |
| serine/threonine kinases | plant pathogens, e.g. *Fusarium*, *Septoria* and other diseases |
| polypeptide having the effect of triggering a hypersensitivity reaction | plant pathogens, e.g. *Fusarium*, *Septoria* and other diseases |
| systemic aquired resistance (SAR) genes | viral, bacterial, fungal and nematodal pathogens |
| chitinases | plant pathogens |
| glucanases | plant pathogens |
| double-strand ribonuclease | viruses such as, for example, BYDV and MSMV |
| envelope proteins | viruses such as, for example, BYDV and MSMV |

TABLE 1-continued

| | |
|---|---|
| toxins of *Bacillus thuringiensis*, | Lepidoptera, Coleoptera, Diptera, |
| VIP 3, *Bacillus cereus* toxins, *Photorabdus* and *Xenorhabdus* toxins | nematodes |
| 3-hydroxysteroid oxidase | Lepidoptera, Coleoptera, Diptera, nematodes |
| peroxidase | Lepidoptera, Coleoptera, Diptera, nematodes |
| aminopeptidase inhibitors, e.g. leucine aminopeptidase inhibitor | Lepidoptera, Coleoptera, Diptera, nematodes |
| lectins | Lepidoptera, Coleoptera, Diptera, nematodes, aphids |
| protease inhibitors, e.g. cystatin, patatin, virgiferin, CPTI | Lepidoptera, Coleoptera, Diptera, nematodes, aphids |
| ribosome-inactivating protein | Lepidoptera, Coleoptera, Diptera, nematodes, aphids |
| HMG-CoA reductase | Lepidoptera, Coleoptera, Diptera, nematodes, aphids |

Plant: Rice

| Structure affected/principle expressed | Feature of the plant/tolerance to |
|---|---|
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 | xenobiotics and herbicides, such as sulphonylurea compounds |
| antifungal polypeptide AlyAFP | plant pathogens |
| glucose oxidase | plant pathogens |
| pyrrolnitrin synthesis gene | plant pathogens |
| serine/threonine kinases | plant pathogens |
| phenylalanine ammonia lyase (PAL) | plant pathogens, e.g. bacterial foliar mildew and inducible rice blast |
| phytoalexins | plant pathogens, e.g. bacterial foliar mildew and rice blast |
| B-1,3-glucanase (antisense) | plant pathogens, e.g. bacterial foliar mildew and rice blast |
| receptor kinase | plant pathogens, e.g. bacterial foliar mildew and rice blast |
| polypeptide having the effect of triggering a hypersensitivity reaction | plant pathogens |
| systemic aquired resistance (SAR) genes | viral, bacterial, fungal and nematodal pathogens |
| chitinases | plant pathogens, e.g. bacterial foliar mildew and rice blast |
| glucanases | plant pathogens |
| double-strand ribonuclease | viruses such as, for example, BYDV and MSMV |
| envelope proteins | viruses such as, for example, BYDV and MSMV |
| toxins of *Bacillus thuringiensis*, | Lepidoptera, e.g. stem borer, Coleoptera, |
| VIP 3, *Bacillus cereus* toxins, *Photorabdus* and *Xenorhabdus* toxins | e.g. weevils such as *Lissorhoptrus oryzophilus*, Diptera, rice planthoppers, e.g. rice brown planthopper |
| 3-hydroxysteroid oxidase | Lepidoptera, e.g. stem borer, Coleoptera, e.g. weevils such as *Lissorhoptrus oryzophilus*, Diptera, rice planthoppers, e.g. rice brown planthopper |
| peroxidase | Lepidoptera, e.g. stem borer, Coleoptera, e.g. weevils such as *Lissorhoptrus oryzophilus*, Diptera, rice planthoppers, e.g. rice brown planthopper |
| aminopeptidase inhibitors, e.g. leucine aminopeptidase inhibitor | Lepidoptera, e.g. stem borer, Coleoptera, e.g. weevils such as *Lissorhoptrus oryzophilus*, Diptera, rice planthoppers, e.g. rice brown planthopper |
| lectins | Lepidoptera, e.g. stem borer, Coleoptera, e.g. weevils such as *Lissorhoptrus oryzophilus*, Diptera, rice planthoppers, e.g. rice brown planthopper |
| protease inhibitors | Lepidoptera, e.g. stem borer, Coleoptera, e.g. weevils such as *Lissorhoptrus oryzophilus*, Diptera, rice planthoppers e.g. rice brown planthopper |
| ribosome-inactivating protein | Lepidoptera, e.g. stem borer, Coleoptera, e.g. weevils such as *Lissorhoptrus oryzophilus*, Diptera, rice planthoppers, e.g. rice brown planthopper |
| HMG-CoA reductase | Lepidoptera, e.g. stem borer, Coleoptera, e.g. weevils such as *Lissorhoptrus oryzophilus*, Diptera, rice planthoppers e.g. rice brown planthopper |

Plant: Soya bean

| Structure affected/principle expressed | Feature of the plant/tolerance to |
|---|---|
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phosphoshikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides, such as sulphonylurea compounds |
| antifungal polypeptide AlyAFP | bacterial and fungal pathogens such as, for example, *Fusarium*, *Sclerotinia*, stem rot |
| oxalate oxidase | bacterial and fungal pathogens such as, for example, *Fusarium*, *Sclerotinia*, stem rot |
| glucose oxidase | bacterial and fungal pathogens such as, for example, *Fusarium*, *Sclerotinia*, stem rot |
| pyrrolnitrin synthesis gene | bacterial and fungal pathogens such as, for example, *Fusarium*, *Sclerotinia*, stem rot |
| serine/threonine kinases | bacterial and fungal pathogens such as, for example, *Fusarium*, *Sclerotinia*, stem rot |
| phenylalanine ammonia lyase (PAL) | bacterial and fungal pathogens such as, for example, *Fusarium*, *Sclerotinia*, stem rot |
| phytoalexins | plant pathogens, e.g. bacterial foliar mildew and rice blast |
| B-1,3-glucanase (antisense) | plant pathogens, e.g. bacterial foliar mildew and rice blast |

TABLE 1-continued

| | |
|---|---|
| receptor kinase | bacterial and fungal pathogens such as, for example, *Fusarium*, *Sclerotinia*, stem rot plant pathogens |
| polypeptide having the effect of triggering a hypersensitivity reaction | |
| systemic aquired resistance (SAR) genes | viral, bacterial, fungal and nematodal pathogens |
| chitinases | bacterial and fungal pathogens such as, for example, *Fusarium*, *Sclerotinia*, stem rot |
| glucanases | bacterial and fungal pathogens such as, for example, *Fusarium*, *Sclerotinia*, stem rot |
| double-strand ribonuclease | viruses such as, for example, BPMV and SbMV |
| envelope proteins | viruses such as, for example, BYDV and MSMV |
| toxins of *Bacillus thuringiensis*, VIP 3, *Bacillus cereus* toxins, *Photorabdus* and *Xenorhabdus* toxins | Lepidoptera, Coleoptera, aphids |
| 3-hydroxysteroid oxidase | Lepidoptera, Coleoptera, aphids |
| peroxidase | Lepidoptera, Coleoptera, aphids |
| aminopeptidase inhibitors, e.g. leucine aminopeptidase inhibitor | Lepidoptera, Coleoptera, aphids |
| lectins | Lepidoptera, Coleoptera, aphids |
| protease inhibitors, e.g. virgiferin | Lepidoptera, Coleoptera, aphids |
| ribosome-inactivating protein | Lepidoptera, Coleoptera, aphids |
| HMG-CoA reductase | Lepidoptera, Coleoptera, aphids |
| barnase | nematodes, e.g. root-knot nematodes and cyst nematodes |
| hatching factor for cyst nematodes | cyst nematodes |
| principles for preventing food uptake | nematodes, e.g. root-knot nematodes and cyst nematodes |

Plant: Potato

| Structure affected/protein expressed | Feature of the plant/tolerance to |
|---|---|
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides, such as sulphonylurea compounds |
| polyphenol oxidase or polyphenol oxidase (antisense) | black spot |
| metallothionein | bacterial and fungal pathogens such as, for example, *Phytophtora*, *Phytophtora*, *Verticillium*, *Rhizoctonia* |
| ribonuclease | |
| antifungal polypeptide AlyAFP | bacterial and fungal pathogens such as, for example, *Phytophtora* |
| oxalate oxidase | bacterial and fungal pathogens such as, for example, *Phytophtora*, *Verticillium*, *Rhizoctonia* |
| glucose oxidase | bacterial and fungal pathogens such as, for example, *Phytophtora*, *Verticillium*, *Rhizoctonia* |
| pyrrolnitrin synthesis gene | bacterial and fungal pathogens such as, for example, *Phytophtora*, *Verticillium*, *Rhizoctonia* |
| serine/threonine kinases | bacterial and fungal pathogens such as, for example, *Phytophtora*, *Verticillium*, *Rhizoctonia* |
| cecropin B | bacteria such as, for example, *Corynebacterium sepedonicum*, *Erwinia carotovora* |
| phenylalanine ammonia lyase (PAL) | bacterial and fungal pathogens such as, for example, *Phytophtora*, *Verticillium*, *Rhizoctonia* |
| phytoalexins | bacterial and fungal pathogens such as, for example, *Phytophtora*, *Verticillium*, *Rhizoctonia* |
| B-1,3-glucanase (antisense) | bacterial and fungal pathogens such as, for example, *Phytophtora*, *Verticillium*, *Rhizoctonia* |
| receptor kinase | bacterial and fungal pathogens such as, for example, *Phytophtora*, *Verticillium*, *Rhizoctonia* |
| polypeptide having the effect of triggering a hypersensitivity reaction | bacterial and fungal pathogens such as, for example, *Phytophtora*, *Verticillium*, *Rhizoctonia* |
| systemic aquired resistance (SAR) genes | viral, bacterial, fungal and nematodal pathogens |
| chitinases | bacterial and fungal pathogens such as, for example, *Phytophtora*, *Verticillium*, *Rhizoctonia* |
| barnase | bacterial and fungal pathogens such as, for example, *Phytophtora*, *Verticillium*, *Rhizoctonia* |
| gene 49 for controlling disease resistance | bacterial and fungal pathogens such as, for example, *Phytophtora*, *Verticillium*, *Rhizoctonia* |
| trans-aldolase (antisense) | black spot |
| glucanases | bacterial and fungal pathogens such as, for example, *Phytophtora*, *Verticillium*, *Rhizoctonia* |
| double-strand ribonuclease | viruses such as, for example, PLRV, PVY and TRV |
| envelope proteins | viruses such as, for example, PLRV, PVY and TRV |
| 17 kDa or 60 kDa protein | viruses such as, for example, PLRV, PVY and TRV |
| nuclear inclusion proteins, e.g. a or b | viruses such as, for example, PLRV, PVY and TRV |
| pseudoubiquitin | viruses such as, for example, PLRV, PVY and TRV |
| replicase | viruses such as, for example, PLRV, PVY and TRV |
| toxins of *Bacillus thuringiensis*, VIP 3, *Bacillus cereus* toxins, *Photorabdus* and *Xenorhabdus* toxins | Coleoptera, e.g. Colorado beetle, aphids |
| 3-hydroxysteroid oxidase | Coleoptera, e.g. Colorado beetle, aphids |
| peroxidase | Coleoptera, e.g. Colorado beetle, aphids |
| aminopeptidase inhibitors, e.g. leucine aminopeptidase inhibitor | Coleoptera, e.g. Colorado beetle, aphids |
| stilbene synthase | Coleoptera, e.g. Colorado beetle, aphids |
| lectins | Coleoptera, e.g. Colorado beetle, aphids |
| protease inhibitors, e.g. cystatin, patatin | Coleoptera, e.g. Colorado beetle, aphids |
| ribosomene-inactivating protein | Coleoptera, e.g. Colorado beetle, aphids |
| HMG-CoA reductase | Coleoptera, e.g. Colorado beetle, aphids |
| hatching factor for cyst nematodes | cyst nematodes |
| barnase | nematodes, e.g. root-knot nematodes and cyst nematodes |
| principles for preventing food uptake | nematodes, e.g. root-knot nematodes and cyst nematodes |

TABLE 1-continued

Plant: Tomato

| Structure affected/principle expressed | Feature of the plant/tolerance to |
|---|---|
| acetolactate synthase (ALS) | sulphonylurea compounds, imidazolinones triazolepyrimidines, pyrimidyloxybenzoates, phthalides |
| acetyl-CoA carboxylase (ACCase) | aryloxyphenoxyalkanecarboxylic acid, cyclohexanedione |
| hydroxyphenylpyruvate dioxygenase (HPPD) | isooxazoles, such as isoxaflutol or isoxachlortol, triones, such as mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles, such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides, such as sulphonylurea compounds |
| polyphenol oxidase or polyphenol oxidase (antisense) | black spot |
| metallothionein | bacterial and fungal pathogens such as, for example, *Phytophtora* |
| ribonuclease | *Phytophtora*, *Verticillium*, *Rhizoctonia* |
| antifungal polypeptide AlyAFP | bacterial and fungal pathogens such as, for example, bacterial blotch, *Fusarium*, soft rot, powdery mildew, foliar blight, leaf mould etc. |
| oxalate oxidase | bacterial and fungal pathogens such as, for example, bacterial blotch, *Fusarium*, soft rot, powdery mildew, foliar blight, leaf mould etc. |
| glucose oxidase | bacterial and fungal pathogens such as, for example, bacterial blotch, *Fusarium*, soft rot, powdery mildew, foliar blight, leaf mould etc. |
| pyrrolnitrin synthesis gene | bacterial and fungal pathogens such as, for example, bacterial blotch, *Fusarium*, soft rot, powdery mildew, foliar blight, leaf mould etc. |
| serine/threonine kinases | bacterial and fungal pathogens such as, for example, bacterial blotch, *Fusarium*, soft rot, powdery mildew, foliar blight, leaf mould etc. |
| cecropin B | bacterial and fungal pathogens such as, for example, bacterial blotch, *Fusarium*, soft rot, powdery mildew, foliar blight, leaf mould etc. |
| phenylalanine ammonia lyase (PAL) | bacterial and fungal pathogens such as, for example, bacterial blotch, *Fusarium*, soft rot, powdery mildew, foliar blight, leaf mould etc. |
| Cf genes, e.g. Cf9 Cf5 Cf4 Cf2 | leaf mould |
| osmotin | early blight |
| alpha hordothionin | bakteria |
| systemin | bacterial and fungal pathogens such as, for example, bacterial blotch, *Fusarium*, soft rot, powdery mildew, foliar blight, leaf mould etc. |
| polygalacturonase inhibitors | bacterial and fungal pathogens such as, for example, bacterial blotch, *Fusarium*, soft rot, powdery mildew, foliar blight, leaf mould etc. |
| Prf control gene | bacterial and fungal pathogens such as, for example, bacterial blotch, *Fusarium*, soft rot, powdery mildew, foliar blight, leaf mould etc. |
| fusarium resistance site phytoalexins | *Fusarium* bacterial and fungal pathogens such as, for example, bacterial blotch, *Fusarium*, soft rot, powdery mildew, foliar blight, leaf mould etc. |
| B-1,3-glucanase (antisense) | bacterial and fungal pathogens such as, for example, bacterial blotch, *Fusarium*, soft rot, powdery mildew, foliar blight, leaf mould etc. |
| receptor kinase | bacterial and fungal pathogens such as, for example, bacterial blotch, *Fusarium*, soft rot, powdery mildew, foliar blight, leaf mould etc. |
| polypeptide having the effect of triggering a hypersensitivity reaction | bacterial and fungal pathogens such as, for example, bacterial blotch, *Fusarium*, soft rot, powdery mildew, foliar blight, leaf mould etc. |
| systemic aquired resistance (SAR) genes | viral, bacterial, fungal and nematodal pathogens |
| chitinases | bacterial and fungal pathogens such as, for example, bacterial blotch, *Fusarium*, soft rot, powdery mildew, foliar blight, leaf mould etc. |
| barnase | bacterial and fungal pathogens such as, for example, bacterial blotch, *Fusarium*, soft rot, powdery mildew, foliar blight, leaf mould etc. |
| glucanases | bacterial and fungal pathogens such as, for example, bacterial blotch, *Fusarium*, soft rot, powdery mildew, foliar blight, leaf mould etc. |
| double-strand ribonuclease | viruses such as, for example, PLRV, PVY and ToMoV |
| envelope proteins | viruses such as, for example, PLRV, PVY and ToMoV |
| 17 kDa or 60 kDa protein | viruses such as, for example, PLRV, PVY and ToMoV |
| nuclear inclusion proteins e.g. a or b or | viruses such as, for example, PLRV, PVY and ToMoV |
| nucleoprotein | TRV |
| pseudoubiquitin | viruses such as, for example, PLRV, PVY and ToMoV |
| replicase | viruses such as, for example, PLRV, PVY and ToMoV |
| toxins of *Bacillus thuringiensis*, VIP 3, *Bacillus cereus* toxins, *Photorabdus* and *Xenorhabdus* toxins | Lepidoptera e.g. *Heliothis*, whitefly aphids |
| 3-hydroxysteroid oxidase | Lepidoptera e.g. *Heliothis*, whitefly, aphids |
| peroxidase | Lepidoptera e.g. *Heliothis*, whitefly, aphids |
| aminopeptidase inhibitors, e.g. leucine | Lepidoptera e.g. *Heliothis*, whitefly, aphids |
| aminopeptidase inhibitor | aphids |
| lectins | Lepidoptera e.g. *Heliothis*, whitefly, aphids |
| protease inhibitors, e.g. cystatin, patatin | Lepidoptera e.g. *Heliothis*, whitefly, aphids |
| ribosome-inactivating protein | Lepidoptera e.g. *Heliothis*, whitefly, aphids |
| stilbene synthase | Lepidoptera e.g. *Heliothis*, whitefly, aphids |
| HMG-CoA reductase | Lepidoptera e.g. *Heliothis*, whitefly, aphids |
| hatching factor for cyst nematodes | cyst nematodes |
| barnase | nematodes, e.g. root-knot nematodes and cyst nematodes |
| principles for preventing food uptake | nematodes, e.g. root-knot nematodes and cyst nematodes |

TABLE 1-continued

Plant: Bell Pepper

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens |
| metallothionein | bacterial and fungal pathogens |
| ribonuclease | bacterial and fungal pathogens |
| antifungal polypeptid AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| cecropin B | bacterial and fungal pathogens, rot, leaf mould, etc. |
| phenylalanine ammonia lyase (PAL) | bacterial and fungal pathogens |
| Cf genes, e.g. Cf9 Ct5 Cf4 Cf2 | bacterial and fungal pathogens |
| osmotin | bacterial and fungal pathogens |
| alpha hordothionine | bacterial and fungal pathogens |
| systemin | bacterial and fungal pathogens |
| polygalacturonase inhibitors | bacterial and fungal pathogens |
| Prf control gene | bacterial and fungal pathogens |
| 12 Fusarium resistance site | Fusarium |
| phytoalexins | bacterial and fungal pathogens |
| B-1,3-glucanase (antisense) | bacterial and fungal pathogens |
| receptor kinase | bacterial and fungal pathogens |
| polypeptide having the effect of triggering a hypersensitivity reaction | bacterial and fungal pathogens |
| systemic aquired resistance (SAR) genes | viral, bacterial, fungal and nematodal pathogens |
| chitinases | bacterial and fungal pathogens |
| barnase | bacterial and fungal pathogens |
| glucanases | bacterial and fungal pathogens |
| double-strand ribonuclease | viruses such as, for example, CMV, TEV |
| envelope proteins | viruses such as, for example, CMV, TEV |
| 17 kDa or 60 kDa protein | viruses such as, for example, CMV, TEV |
| nuclear inclusion proteins e.g. a or b or nucleoprotein | viruses such as, for example, CMV, TEV |
| pseudoubiquitin | viruses such as, for example, CMV, TEV |
| replicase | viruses such as, for example, CMV, TEV |
| toxins of Bacillus thuringiensis, VIP 3, Bacillus cereus toxins, Photorabdus and Xenorhabdus toxins | Lepidoptera, whitefly, aphids |
| 3-hydroxysteroid oxidase | Lepidoptera, whitefly, aphids |
| peroxidase | Lepidoptera, whitefly, aphids |
| aminopeptidase inhibitors, e.g. leucine aminopeptidase inhibitor | Lepidoptera, whitefly, aphids |
| lectins | Lepidoptera, whitefly, aphids |
| protease inhibitors, e.g. cystatin, patatin | Lepidoptera, whitefly, aphids |
| ribosome-inactivating protein | Lepidoptera, whitefly, aphids |
| stilbene synthase | Lepidoptera, whitefly, aphids |
| HMG-CoA reductase | Lepidoptera, whitefly, aphids |
| hatching factor for cyst nematodes | cyst nematodes |
| barnase | nematodes, e.g. root-knot nematodes and cyst nematodes |
| principles for preventing food uptake | nematodes, e.g. root-knot nematodes and cyst nematodes |

Plant: Grapevines

| Structure affected/principle expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens such as Botrytis and powdery mildew |
| metallothionein | bacterial and fungal pathogens such as Botrytis and powdery mildew |
| ribonuclease | bacterial and fungal pathogens such as Botrytis and powdery mildew |
| antifungal polypeptide AlyAFP | bacterial and fungal pathogens such as Botrytis and powdery mildew |
| oxalate oxidase | bacterial and fungal pathogens such as Botrytis and powdery mildew |
| glucose oxidase | bacterial and fungal pathogens such as Botrytis and powdery mildew |
| pyrrolnitrin synthesis genes | bacterial and fungal pathogens such as Botrytis and powdery mildew |
| serine/threonine kinases | bacterial and fungal pathogens such as Botrytis and powdery mildew |
| cecropin B | bacterial and fungal pathogens such as Botrytis and powdery mildew |
| phenylalanine ammonia lyase (PAL) | bacterial and fungal pathogens such as Botrytis and powdery mildew |
| Cf genes, e.g. Cf9 Cf5 Cf4 Cf2 | bacterial and fungal pathogens such as Botrytis and powdery mildew |
| osmotin | bacterial and fungal pathogens such as Botrytis and powdery mildew |
| alpha hordothionine | bacterial and fungal pathogens such as Botrytis and powdery mildew |
| systemin | bacterial and fungal pathogens such as Botrytis and powdery mildew |
| polygalacturonase inhibitors | bacterial and fungal pathogens such as Botrytis and powdery mildew |
| Prf control gene | bacterial and fungal pathogens such as Botrytis and powdery mildew |

TABLE 1-continued

| Structure affected/protein expressed | Feature of the plant/tolerance to |
|---|---|
| phytoalexins | bacterial and fungal pathogens such as Botrytis and powdery mildew |
| B-1,3-glucanase (antisense) | bacterial and fungal pathogens such as Botrytis and powdery mildew |
| receptor kinase | bacterial and fungal pathogens such as Botrytis and powdery mildew |
| polypeptide having the effect of triggering a hypersensitivity reaction | bacterial and fungal pathogens such as Botrytis and powdery mildew |
| systemic aquired resistance (SAR) genes | viral, bacterial, fungal and nematodal pathogens |
| chitinases | bacterial and fungal pathogens such as Botrytis and powdery mildew |
| barnase | bacterial and fungal pathogens such as Botrytis and powdery mildew |
| glucanases | bacterial and fungal pathogens such as Botrytis and powdery mildew |
| double-strand ribonuclease | viruses |
| envelope proteins | viruses |
| 17 kDa or 60 kDa protein | viruses |
| nuclear inclusion proteins e.g. a or b or nucleoprotein | viruses |
| pseudoubiquitin | viruses |
| replicase | viruses |
| toxins of Bacillus thuringiensis, VIP 3, Bacillus cereus toxins, Photorabdus and Xenorhabdus toxins | Lepidoptera, aphids |
| 3-hydroxysteroid oxidase | Lepidoptera, aphids |
| peroxidase | Lepidoptera, aphids |
| aminopeptidase inhibitors, e.g. leucine aminopeptidase inhibitor | Lepidoptera, aphids |
| lectins | Lepidoptera, aphids |
| protease inhibitors, e.g. cystatin, patatin | Lepidoptera, aphids |
| ribosome-inactivating protein | Lepidoptera, aphids |
| stilbene synthase | Lepidoptera, aphids, diseases |
| HMG-CoA reductase | Lepidoptera, aphids |
| hatching factor for cyst nematodes | cyst nematodes |
| barnase | nematodes, e.g. root-knot nematodes and cyst nematodes or general diseases |
| CBI | root-knot nematodes |
| principles for preventing food uptake | nematodes, e.g. root-knot nematodes or root-cyst nematodes |

Plant: Oilseed rape

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens such as Cylindrosporium, Phoma, Sclerotinia |
| metallothionein | bacterial and fungal pathogens such as Cylindrosporium, Phoma, Sclerotinia |
| ribonuclease | bacterial and fungal pathogens such as Cylindrosporium, Phoma, Sclerotinia |
| antifungal polypeptid AlyAFP | bacterial and fungal pathogens such as Cylindrosporium, Phoma, Sclerotinia |
| oxalate oxidase | bacterial and fungal pathogens such as Cylindrosporium, Phoma, Sclerotinia |
| glucose oxidase | bacterial and fungal pathogens such as Cylindrosporium, Phoma, Sclerotinia |
| pyrrolnitrin synthesis genes | bacterial and fungal pathogens such as Cylindrosporium, Phoma, Sclerotinia |
| serine/threonine kinases | bacterial and fungal pathogens such as Cylindrosporium, Phoma, Sclerotinia |
| cecropin B | bacterial and fungal pathogens such as Cylindrosporium, Phoma, Sclerotinia |
| phenylalanine ammonia lyase (PAL) | bacterial and fungal pathogens such as Cylindrosporium, Phoma, Sclerotinia |
| Cf genes, e.g. Cf9 Cf5 Cf4 Cf2 | bacterial and fungal pathogens such as Cylindrosporium, Phoma, Sclerotinia |
| osmotin | bacterial and fungal pathogens such as Cylindrosporium, Phoma, Sclerotinia |
| alpha hordothionine | bacterial and fungal pathogens such as Cylindrosporium, Phoma, Sclerotinia |
| systemin | bacterial and fungal pathogens such as Cylindrosporium, Phoma, Sclerotinia |
| polygalacturonase inhibitors | bacterial and fungal pathogens such as Cylindrosporium, Phoma, Sclerotinia |
| Prf control gene | bacterial and fungal pathogens such as Cylindrosporium, Phoma, Sclerotinia |
| phytoalexins | bacterial and fungal pathogens such as Cylindrosporium, Phoma, Sclerotinia |
| B-1,3-glucanase (antisense) | bacterial and fungal pathogens such as Cylindrosporium, Phoma, Sclerotinia |
| receptor kinase | bacterial and fungal pathogens such as Cylindrosporium, Phoma, Sclerotinia |
| polypeptide having the effect of triggering a hypersensitivity reaction | bacterial and fungal pathogens such as Cylindrosporium, Phoma, Sclerotinia |
| systemic aquired resistance (SAR) genes | viral, bacterial, fungal and nematodal pathogens |
| chitinases | bacterial and fungal pathogens such as Cylindrosporium, Phoma, Sclerotinia |
| barnase | bacterial and fungal pathogens such as Cylindrosporium, Phoma, Sclerotinia nematodes |
| glucanases | bacterial and fungal pathogens such as Cylindrosporium, Phoma, Sclerotinia |
| double-strand ribonuclease | viruses |
| envelope proteins | viruses |
| 17 kDa or 60 kDa protein | viruses |
| nuclear inclusion proteins e.g. a or b or nucleoprotein | viruses |
| pseudoubiquitin | viruses |
| replicase | viruses |
| toxins of Bacillus thuringiensis, VIP 3, Bacillus cereus toxins, Photorabdus and Xenorhabdus toxins | Lepidoptera, aphids |
| 3-hydroxysteroid oxidase | Lepidoptera, aphids |
| peroxidase | Lepidoptera, aphids |
| aminopeptidase inhibitors, e.g. leucine aminopeptidase inhibitor | Lepidoptera, aphids |
| lectins | Lepidoptera, aphids |
| protease inhibitors, e.g. cystatin, patatin, CPTI | Lepidoptera, aphids |
| ribosome-inactivating protein | Lepidoptera, aphids |
| stilbene synthase | Lepidoptera, aphids, diseases |
| HMG-CoA reductase | Lepidoptera, aphids |
| hatching factor for cyst nematodes | cyst nematodes |

TABLE 1-continued

| Structure affected/protein expressed | Feature of the plant/tolerance to |
|---|---|
| barnase | nematodes, e.g. root-knot nematodes and cyst nematodes |
| CBI | root-knot nematodes |
| principles for preventing food uptake | nematodes, e.g. root-knot nematodes and |
| induced at nematode feeding sites | root-cyst nematodes |

Plant: *Brassica* vegetables (cabbage, Brussels sprouts etc.)

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens |
| metallothionein | bacterial and fungal pathogens |
| ribonuclease | bacterial and fungal pathogens |
| antifungal polypeptid AlyAFP | bacterial and fungal pathogens |
| oxalate oxidase | bacterial and fungal pathogens |
| glucose oxidase | bacterial and fungal pathogens |
| pyrrolnitrin synthesis genes | bacterial and fungal pathogens |
| serine/threonine kinases | bacterial and fungal pathogens |
| cecropin B | bacterial and fungal pathogens |
| phenylalanine ammonia lyase (PAL) | bacterial and fungal pathogens |
| Cf genes, e.g. Cf9 Cf5 Cf4 Cf2 | bacterial and fungal pathogens |
| osmotin | bacterial and fungal pathogens |
| alpha hordothionine | bacterial and fungal pathogens |
| systemin | bacterial and fungal pathogens |
| polygalacturonase inhibitors | bacterial and fungal pathogens |
| Prf control gene | bacterial and fungal pathogens |
| phytoalexins | bacterial and fungal pathogens |
| B-1,3-glucanase (antisense) | bacterial and fungal pathogens |
| receptor kinase | bacterial and fungal pathogens |
| polypeptide having the effect of triggering a hypersensitivity reaction | bacterial and fungal pathogens |
| systemic aquired resistance (SAR) genes | viral, bacterial, fungal and nematodal pathogens |
| chitinases | bacterial and fungal pathogens |
| barnase | bacterial and fungal pathogens |
| glucanases | bacterial and fungal pathogens |
| double-strand ribonuclease | viruses |
| envelope proteins | viruses |
| 17 kDa or 60 kDa protein | viruses |
| nuclear inclusion proteins e.g. a or b or nucleoprotein | viruses |
| pseudoubiquitin | viruses |
| replicase | viruses |
| toxins of *Bacillus thuringiensis*, | Lepidoptera, aphids |
| VIP 3, *Bacillus cereus* toxins, *Photorabdus* and *Xenorhabdus* toxins | |
| 3-hydroxysteroid oxidase | Lepidoptera, aphids |
| peroxidase | Lepidoptera, aphids |
| aminopeptidase inhibitors, e.g. leucine aminopeptidase inhibitor | Lepidoptera, aphids |
| lectins | Lepidoptera, aphids |
| protease inhibitors, e.g. cystatin, patatin, CPTI | Lepidoptera, aphids |
| ribosome-inactivating protein | Lepidoptera, aphids |
| stilbene synthase | Lepidoptera, aphids, diseases |
| HMG-CoA reductase | Lepidoptera, aphids |
| hatching factor for cyst nematodes | cyst nematodes |
| barnase | nematodes, e.g. root-knot nematodes and cyst nematodes |
| CBI | root-knot nematodes |
| principles for preventing food uptake | nematodes, e.g. root-knot nematodes and |
| induced at nematode feeding sites | root-cyst nematodes cyst nematodes |

Plants: Pomaceous fruit, e.g. apples, pears

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial and fungal pathogens such as storage scab on apples or fire-blight |
| metallothionein | bacterial and fungal pathogens such as storage scab on apples or fire-blight |
| ribonuclease | bacterial and fungal pathogens such as storage scab on apples or fire-blight |
| antifungal polypeptid AlyAFP | bacterial and fungal pathogens such as storage scab on apples or fire-blight |
| oxalate oxidase | bacterial and fungal pathogens such as storage scab on apples or fire-blight |
| glucose oxidase | bacterial and fungal pathogens such as storage scab on apples or fire-blight |
| pyrrolnitrin synthesis genes | bacterial and fungal pathogens such as storage scab on apples or fire-blight |
| serine/threonine kinases | bacterial and fungal pathogens such as storage scab on apples or fire-blight |
| cecropin B | bacterial and fungal pathogens such as storage scab on apples or fire-blight |
| phenylalanine ammonia lyase (PAL) | bacterial and fungal pathogens such as storage scab on apples or fire-blight |
| Cf genes, e.g. Cf9 Cf5 Cf4 Cf2 | bacterial and fungal pathogens such as storage scab on apples or fire-blight |
| osmotin | bacterial and fungal pathogens such as storage scab on apples or fire-blight |

TABLE 1-continued

| | |
|---|---|
| alpha hordothionine | bacterial and fungal pathogens such as storage scab on apples or fire-blight |
| systemin | bacterial and fungal pathogens such as storage scab on apples or fire-blight |
| polygalacturonase inhibitors | bacterial and fungal pathogens such as storage scab on apples or fire-blight |
| Prf control gene | bacterial and fungal pathogens such as storage scab on apples or fire-blight |
| phytoalexins | bacterial and fungal pathogens such as storage scab on apples or fire-blight |
| B-1,3-glucanase (antisense) | bacterial and fungal pathogens such as storage scab on apples or fire-blight |
| receptor kinase | bacterial and fungal pathogens such as storage scab on apples or fire-blight |
| polypeptide having the effect of triggering a hypersensitivity reaction | bacterial and fungal pathogens such as storage scab on apples or fire-blight |
| systemic aquired resistance (SAR) genes | viral, bacterial, fungal and nematodal pathogens |
| lytic protein | bacterial and fungal pathogens such as storage scab on apples or fire-blight |
| lysozyme | bacterial and fungal pathogens such as storage scab on apples or fire-blight |
| chitinases | bacterial and fungal pathogens such as storage scab on apples or fire-blight |
| barnase | bacterial and fungal pathogens such as storage scab on apples or fire-blight |
| glucanases | bacterial and fungal pathogens such as storage scab on apples or fire-blight |
| double-strand ribonuclease | viruses |
| envelope proteins | viruses |
| 17 kDa or 60 kDa protein | viruses |
| nuclear inclusion proteins e.g. a or b or nucleoprotein | viruses |
| pseudoubiquitin | viruses |
| replicase | viruses |
| toxins of *Bacillus thuringiensis*, VIP 3, *Bacillus cereus* toxins, *Photorabdus* and *Xenorhabdus* toxins | Lepidoptera, aphids, mites |
| 3-hydroxysteroid oxidase | Lepidoptera, aphids, mites |
| peroxidase | Lepidoptera, aphids, mites |
| aminopeptidase inhibitors, e.g. leucine aminopeptidase inhibitor | Lepidoptera, aphids, mites |
| lectins | Lepidoptera, aphids, mites |
| protease inhibitors, e.g. cystatin, patatin, CPTI | Lepidoptera, aphids, mites |
| ribosome-inactivating protein | Lepidoptera, aphids, mites |
| stilbene synthase | Lepidoptera, aphids, diseases, mites |
| HMG-CoA reductase | Lepidoptera, aphids, mites |
| hatching factor for cyst nematodes | cyst nematodes |
| barnase | nematodes, e.g. root-knot nematodes and cyst nematodes |
| CBI | root-knot nematodes |
| principles for preventing food uptake | nematodes, e.g. root-knot nematodes and root-cyst nematodes |
| induced at nematode feeding sites | |

| Plant: Melon | |
|---|---|
| Structure affected/protein expressed | Feature of the plant/tolerance to |
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens such as *Phytophtora* |
| metallothionein | bacterial or fungal pathogens such as *Phytophtora* |
| ribonuclease | bacterial or fungal pathogens such as *Phytophtora* |
| antifungal polypeptid AlyAFP | bacterial or fungal pathogens such as *Phytophtora* |
| oxalate oxidase | bacterial or fungal pathogens such as *Phytophtora* |
| glucose oxidase | bacterial or fungal pathogens such as *Phytophtora* |
| pyrrolnitrin synthesis genes | bacterial or fungal pathogens such as *Phytophtora* |
| serine/threonine kinases | bacterial or fungal pathogens such as *Phytophtora* |
| cecropin B | bacterial or fungal pathogens such as *Phytophtora* |
| phenylalanine ammonia lyase (PAL) | bacterial or fungal pathogens such as *Phytophtora* |
| Cf genes, e.g. Cf9 Cf5 Cf4 Cf2 | bacterial or fungal pathogens such as *Phytophtora* |
| osmotin | bacterial or fungal pathogens such as *Phytophtora* |
| alpha hordothionine | bacterial or fungal pathogens such as *Phytophtora* |
| systemin | bacterial or fungal pathogens such as *Phytophtora* |
| polygalacturonase inhibitors | bacterial or fungal pathogens such as *Phytophtora* |
| Prf control gene | bacterial or fungal pathogens such as *Phytophtora* |
| phytoalexins | bacterial or fungal pathogens such as *Phytophtora* |
| B-1,3-glucanase (antisense) | bacterial or fungal pathogens such as *Phytophtora* |
| receptor kinase | bacterial or fungal pathogens such as *Phytophtora* |
| polypeptide having the effect of triggering a hypersensitivity reaction | bacterial or fungal pathogens such as *Phytophtora* |
| systemic aquired resistance (SAR) genes | viral, bacterial, fungal and nematodal pathogens |
| lytic protein | bacterial or fungal pathogens such as *Phytophtora* |
| lysozyme | bacterial or fungal pathogens such as *Phytophtora* |
| chitinases | bacterial or fungal pathogens such as *Phytophtora* |
| barnase | bacterial or fungal pathogens such as *Phytophtora* |
| glucanases | bacterial or fungal pathogens such as *Phytophtora* |
| double-strand ribonuclease | viruses such as CMV, PRSV, WMV2, SMV, ZYMV |
| envelope proteins | viruses such as CMV, PRSV, WMV2, SMV, ZYMV |
| 17 kDa or 60 kDa protein | viruses such as CMV, PRSV, WMV2, SMV, ZYMV |
| nuclear inclusion proteins e.g. a or b or nucleoprotein | viruses such as CMV, PRSV, WMV2, SMV, ZYMV |
| pseudoubiquitin | viruses such as CMV, PRSV, WMV2, SMV, ZYMV |

TABLE 1-continued

| | |
|---|---|
| replicase | viruses such as CMV, PRSV, WMV2, SMV, ZYMV |
| toxins of *Bacillus thuringiensis*, VIP 3, *Bacillus cereus* toxins, *Photorabdus* and *Xenorhabdus* toxins | Lepidoptera, aphids, mites |
| 3-hydroxysteroid oxidase | Lepidoptera, aphids, mites, whitefly |
| peroxidase | Lepidoptera, aphids, mites, whitefly |
| aminopeptidase inhibitors, e.g. leucine aminopeptidase inhibitor | Lepidoptera, aphids, mites, whitefly |
| lectins | Lepidoptera, aphids, mites, whitefly |
| protease inhibitors, e.g. cystatin, patatin, CPTI, virgiferin | Lepidoptera, aphids, mites, whitefly |
| ribosome-inactivating protein | Lepidoptera, aphids, mites, whitefly |
| stilbene synthase | Lepidoptera, aphids, mites, whitefly |
| HMG-CoA reductase | Lepidoptera, aphids, mites, whitefly |
| hatching factor for cyst nematodes | cyst nematodes |
| barnase | nematodes, e.g. root-knot nematodes and cyst nematodes |
| CBI | root-knot nematodes |
| principles for preventing food uptake | nematodes, e.g. root-knot nematodes and |
| induced at nematode feeding sites | root-cyst nematodes |

Plant: Banana

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |
| lytic protein | bacterial or fungal pathogens |
| lysozyme | bacterial or fungal pathogens |
| chitinases | bacterial or fungal pathogens |
| barnase | bacterial or fungal pathogens |
| glucanases | bacterial or fungal pathogens |
| double-strand ribonuclease | viruses such as the Banana Bunchy Top Virus (BBTV) |
| envelope proteins | viruses such as the Banana Bunchy Top Virus (BBTV) |
| 17 kDa or 60 kDa protein | viruses such as the Banana Bunchy Top Virus (BBTV) |
| nuclear inclusion proteins e.g. a or b or nucleoprotein | viruses such as the Banana Bunchy Top Virus (BBTV) |
| pseudoubiquitin | viruses such as the Banana Bunchy Top Virus (BBTV) |
| replicase | viruses such as the Banana Bunchy Top Virus (BBTV) |
| toxins of *Bacillus thuringiensis*, VIP 3, *Bacillus cereus* toxins, *Photorabdus* and *Xenorhabdus* toxins | Lepidoptera, aphids, mites, nematodes |
| 3-hydroxysteroid oxidase | Lepidoptera, aphids, mites, nematodes |
| peroxidase | Lepidoptera, aphids, mites, nematodes |
| aminopeptidase inhibitors, e.g. leucine aminopeptidase inhibitor | Lepidoptera, aphids, mites, nematodes |
| lectins | Lepidoptera, aphids, mites, nematodes |
| protease inhibitors, e.g. cystatin, patatin, CPTI, virgiferin | Lepidoptera, aphids, mites, nematodes |
| ribosome-inactivating protein | Lepidoptera, aphids, mites, nematodes |
| stilbene synthase | Lepidoptera, aphids, mites, nematodes |
| HMG-CoA reductase | Lepidoptera, aphids, mites, nematodes |
| hatching factor for cyst nematodes | cyst nematodes |
| barnase | nematodes, e.g. root-knot nematodes and cyst nematodes |
| CBI | root-knot nematodes |
| principles for preventing food uptake | nematodes, e.g. root-knot nematodes and |
| induced at nematode feeding sites | root-cyst nematodes |

Plant: Cotton

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthese |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |

TABLE 1-continued

| Feature affected/protein expressed | Feature of the plant/tolerance to |
|---|---|
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |
| lytic protein | bacterial or fungal pathogens |
| lysozyme | bacterial or fungal pathogens |
| chitinases | bacterial or fungal pathogens |
| barnase | bacterial or fungal pathogens |
| glucanases | bacterial or fungal pathogens |
| double-strand ribonuclease | viruses such as the wound tumour virus (WTV) |
| envelope proteins | viruses such as the wound tumour virus (WTV) |
| 17 kDa or 60 kDa protein | viruses such as the wound tumour virus (WTV) |
| nuclear inclusion proteins e.g. a or b or nucleoprotein | viruses such as the wound tumour virus (WTV) |
| pseudoubiquitin | viruses such as the wound tumour virus (WTV) |
| replicase | viruses such as the wound tumour virus (WTV) |
| toxins of *Bacillus thuringiensis*, VIP 3, *Bacillus cereus* toxins, *Photorabdus* and *Xenorhabdus* toxins | Lepidoptera, aphids, mites, nematodes, whitefly |
| 3-hydroxysteroid oxidase | Lepidoptera, aphids, mites, nematodes, whitefly |
| peroxidase | Lepidoptera, aphids, mites, nematodes, whitefly |
| aminopeptidase inhibitors, e.g. leucine aminopeptidase inhibitor | Lepidoptera, aphids, mites, nematodes, whitefly |
| lectins | Lepidoptera, aphids, mites, nematodes, whitefly |
| protease inhibitors, e.g. cystatin, patatin, CPTI, virgiferin | Lepidoptera, aphids, mites, nematodes, whitefly |
| ribosome-inactivating protein | Lepidoptera, aphids, mites, nematodes, whitefly |
| stilbene synthase | Lepidoptera, aphids, mites, nematodes, whitefly |
| HMG-CoA reductase | Lepidoptera, aphids, mites, nematodes, whitefly |
| hatching factor for cyst nematodes | cyst nematodes |
| barnase | nematodes, e.g. root-knot nematodes and cyst nematodes |
| CBI | root-knot nematodes |
| principles for preventing food uptake | nematodes, e.g. root-knot nematodes and |
| induced at nematode feeding sites | root-cyst nematodes |

TABLE 1-continued

Plant: Sugar cane

| Feature affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |
| oxalate oxidase | bacterial or fungal pathogens |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |
| lytic protein | bacterial or fungal pathogens |
| lysozyme | bacterial or fungal pathogens, e.g. *Clavibacter* |
| chitinases | bacterial or fungal pathogens |
| barnase | bacterial or fungal pathogens |
| glucanases | bacterial or fungal pathogens |
| double-strand ribonuclease | viruses such as SCMV, SrMV |
| envelope proteins | viruses such as SCMV, SrMV |
| 17 kDa or 60 kDa protein | viruses such as SCMV, SrMV |
| nuclear inclusion proteins e.g. a or b or nucleoprotein | viruses such as SCMV, SrMV |
| pseudoubiquitin | viruses such as SCMV, SrMV |
| replicase | viruses such as SCMV, SrMV |
| toxins of *Bacillus thuringiensis*, | Lepidoptera, aphids, mites, nematodes, |

TABLE 1-continued

| Structure affected/protein expressed | Feature of the plant/tolerance to |
|---|---|
| VIP 3, *Bacillus cereus* toxins, *Photorabdus* and *Xenorhabdus* toxins | whitefly, beetles such as e.g. the Mexican rice borer |
| 3-hydroxysteroid oxidase | Lepidoptera, aphids, mites, nematodes, whitefly, beetles such as e.g. the Mexican rice borer |
| peroxidase | Lepidoptera, aphids, mites, nematodes, whitefly, beetles such as e.g. the Mexican rice borer |
| aminopeptidase inhibitors, e.g. leucine aminopeptidase inhibitor | Lepidoptera, aphids, mites, nematodes, whitefly, beetles such as e.g. the Mexican rice borer |
| lectins | Lepidoptera, aphids, mites, nematodes, whitefly, beetles such as e.g. the Mexican rice borer |
| protease inhibitors, e.g. cystatin, patatin, CPTI, virgiferin | Lepidoptera, aphids, mites, nematodes, whitefly, beetles such as e.g. the Mexican rice borer |
| ribosome-inactivating protein | Lepidoptera, aphids, mites, nematodes, whitefly, beetles such as e.g. the Mexican rice borer |
| stilbene synthase | Lepidoptera, aphids, mites, nematodes, whitefly, beetles such as e.g. the Mexican rice borer |
| HMG-CoA reductase | Lepidoptera, aphids, mites, nematodes, whitefly, beetles such as e.g. the Mexican rice borer |
| hatching factor for cyst nematodes | cyst nematodes |
| barnase | nematodes, e.g. root-knot nematodes and cyst nematodes |
| CBI | root-knot nematodes |
| principles for preventing food uptake | nematodes, e.g. root-knot nematodes and |
| induced at nematode feeding sites | root-cyst nematodes |

Plant: Sunflower

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |
| oxalate oxidase | bacterial or fungal pathogens, e.g. *Sclerotinia* |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |
| lytic protein | bacterial or fungal pathogens |
| lysozyme | bacterial or fungal pathogens |
| chitinases | bacterial or fungal pathogens |
| barnase | bacterial or fungal pathogens |
| glucanases | bacterial or fungal pathogens |
| double-strand ribonuclease | viruses such as CMV, TMV |
| envelope proteins | viruses such as CMV, TMV |
| 17 kDa or 60 kDa protein | viruses such as CMV, TMV |
| nuclear inclusion proteins e.g. a or b or nucleoprotein | viruses such as CMV, TMV |
| pseudoubiquitin | viruses such as CMV, TMV |
| replicase | viruses such as CMV, TMV |
| toxins of *Bacillus thuringiensis*, | Lepidoptera, aphids, mites, nematodes, whitefly, beetles |
| VIP 3, *Bacillus cereus* toxins, *Photorabdus* and *Xenorhabdus* toxins | whitefly, beetles |
| 3-hydroxysteroid oxidase | Lepidoptera, aphids, mites, nematodes, whitefly, beetles |
| peroxidase | Lepidoptera, aphids, mites, nematodes, whitefly, beetles |
| aminopeptidase inhibitors, e.g. leucine aminopeptidase inhibitor | Lepidoptera, aphids, mites, nematodes, whitefly, beetles |
| lectins | Lepidoptera, aphids, mites, nematodes, whitefly, beetles |
| protease inhibitors, e.g. cystatin, patatin, CPTI, virgiferin | Lepidoptera, aphids, mites, nematodes, whitefly, beetles |
| ribosome-inactivating protein | Lepidoptera, aphids, mites, nematodes, whitefly, beetles |
| stilbene synthase | Lepidoptera, aphids, mites, nematodes, whitefly, beetles |
| HMG-CoA reductase | Lepidoptera, aphids, mites, nematodes, whitefly, beetles |
| hatching factor for cyst nematodes | cyst nematodes |
| barnase | nematodes, e.g. root-knot nematodes and cyst nematodes |
| CBI | root-knot nematodes |
| principles for preventing food uptake | nematodes, e.g. root-knot nematodes and |
| induced at nematode feeding sites | root-cyst nematodes |

Plants: Sugar beet, turnips

| Structure affected/protein expressed | Feature of the plant/tolerance to |
|---|---|
| acetolactate synthase (ALS) | sulphonylurea compounds, imidazolinones triazolopyrimidines, pyrimidyloxybenzoates, phthalides |
| acetyl-CoA carboxylase (ACCase) | aryloxyphenoxyalkanecarboxylic acids, cyclohexanediones |
| hydroxyphenylpyruvate dioxygenase (HPPD) | isoxazoles such as, for example, isoxaflutole or isoxachlortole, triones such as, for example, mesotrione or sulcotrione |
| phosphinothricin acetyltransferase | phosphinothricin |
| O-methyl transferase | modified lignin content |
| glutamine synthetase | glufosinate, bialaphos |

TABLE 1-continued

| | |
|---|---|
| adenylosuccinate lyase (ADSL) | inhibitors of IMP and AMP synthesis |
| adenylosuccinate synthase | inhibitors of adenylosuccinate synthesis |
| anthranilate synthase | inhibitors of tryptophan synthesis and degradation |
| nitrilase | 3,5-dihalo-4-hydroxybenzonitriles such as bromoxynil and loxinyl |
| 5-enolpyruvyl-3-phospho-shikimate synthase (EPSPS) | glyphosate or sulphosate |
| glyphosate oxidoreductase | glyphosate or sulphosate |
| protoporphyrinogen oxidase (PROTOX) | diphenyl ethers, cyclic imides, phenylpyrazoles, pyridine derivatives, phenopylate, oxadiazoles etc. |
| cytochrome P450 e.g. P450 SU1 or selection | xenobiotics and herbicides such as, for example, sulphonylurea compounds |
| polyphenol oxidase or polyphenol oxidase (antisense) | bacterial or fungal pathogens |
| metallothionein | bacterial or fungal pathogens |
| ribonuclease | bacterial or fungal pathogens |
| antifungal polypeptid AlyAFP | bacterial or fungal pathogens |
| oxalate oxidase | bacterial or fungal pathogens, e.g. Sclerotinia |
| glucose oxidase | bacterial or fungal pathogens |
| pyrrolnitrin synthesis genes | bacterial or fungal pathogens |
| serine/threonine kinases | bacterial or fungal pathogens |
| cecropin B | bacterial or fungal pathogens |
| phenylalanine ammonia lyase (PAL) | bacterial or fungal pathogens |
| Cf genes, e.g. Cf9 Cf5 Cf4 Cf2 | bacterial or fungal pathogens |
| osmotin | bacterial or fungal pathogens |
| alpha hordothionine | bacterial or fungal pathogens |
| systemin | bacterial or fungal pathogens |
| polygalacturonase inhibitors | bacterial or fungal pathogens |
| Prf control gene | bacterial or fungal pathogens |
| phytoalexins | bacterial or fungal pathogens |
| B-1,3-glucanase (antisense) | bacterial or fungal pathogens |
| AX + WIN-proteins | bacterial and fungal pathogens such as Cercospora beticola |
| receptor kinase | bacterial or fungal pathogens |
| polypeptide having the effect of triggering a hypersensitivity reaction | bacterial or fungal pathogens |
| systemic aquired resistance (SAR) genes | viral, bacterial, fungal and nematodal pathogens |
| lytic protein | bacterial or fungal pathogens |
| lysozyme | bacterial or fungal pathogens |
| chitinases | bacterial or fungal pathogens |
| barnase | bacterial or fungal pathogens |
| glucanases | bacterial or fungal pathogens |
| double-strand ribonuclease | viruses such as, for example, BNYVV |
| envelope proteins | viruses such as, for example, BNYVV |
| 17 kDa or 60 kDa protein | viruses such as, for example, BNYVV |
| nuclear inclusion proteins e.g. a or b or nucleoprotein | viruses such as, for example, BNYVV |
| pseudoubiquitin | viruses such as, for example, BNYVV |
| replicase | viruses such as, for example, BNYVV |
| toxins of *Bacillus thuringiensis*, VIP 3, *Bacillus cereus* toxins, *Photorabdus* and *Xenorhabdus* toxins | Lepidoptera, aphids, mites, nematodes, whitefly, beetles, root-flies |
| 3-hydroxysteroid oxidase | Lepidoptera, aphids, mites, nematodes, whitefly, beetles, root-flies |
| peroxidase | Lepidoptera, aphids, mites, nematodes, whitefly, beetles, root-flies |
| aminopeptidase inhibitors, e.g. leucine aminopeptidase inhibitor | Lepidoptera, aphids, mites, nematodes, whitefly, beetles, root-flies |
| lectins | Lepidoptera, aphids, mites, nematodes, whitefly, beetles, root-flies |
| protease inhibitors, e.g. cystatin, patatin, CPTI, virgiferin | Lepidoptera, aphids, mites, nematodes, whitefly, beetles, root-flies |
| ribosome-inactivating protein | Lepidoptera, aphids, mites, nematodes, whitefly, beetles, root-flies |
| stilbene synthase | Lepidoptera, aphids, mites, nematodes, whitefly, beetles, root-flies |
| HMG-CoA reductase | Lepidoptera, aphids, mites, nematodes, whitefly, beetles, root-flies |
| hatching factor for cyst nematodes | cyst nematodes |
| barnase | nematodes, e.g. root-knot nematodes and cyst nematodes |
| beet cyst nematode resistance site | cyst nematodes |
| CBI | root-knot nematodes |
| principles for preventing food uptake induced | nematodes, e.g. root-knot nematodes and root-cyst nematodes |

TABLE 2

| AP | Control of |
|---|---|
| CryIA(a) | *Adoxophyes* spp. |
| CryIA(a) | *Agrotis* spp. |
| CryIA(a) | *Alabama argiliaceae* |
| CryIA(a) | *Anticarsia gemmatalis* |
| CryIA(a) | *Chilo* spp. |
| CryIA(a) | *Clysia ambiguella* |
| CryIA(a) | *Crocidolomia binotalis* |
| CryIA(a) | *Cydia* spp. |
| CryIA(a) | *Diparopsis castanea* |
| CryIA(a) | *Earias* spp. |
| CryIA(a) | *Ephestia* spp. |
| CryIA(a) | *Heliothis* spp. |
| CryIA(a) | *Heliula undalis* |
| CryIA(a) | *Keiferia lycopersicella* |
| CryIA(a) | *Leucoptera scitella* |
| CryIA(a) | *Lithocollethis* spp. |
| CryIA(a) | *Lobesia botrana* |
| CryIA(a) | *Ostrinia nubilalis* |
| CryIA(a) | *Pandemis* spp. |
| CryIA(a) | *Pectinophora gossyp.* |
| CryIA(a) | *Phyllocnistis citrella* |
| CryIA(a) | *Pieris* spp. |
| CryIA(a) | *Plutella xylostella* |
| CryIA(a) | *Scirpophaga* spp. |
| CryIA(a) | *Sesamia* spp. |
| CryIA(a) | *Sparganothis* spp. |
| CryIA(a) | *Spodoptera* spp. |
| CryIA(a) | *Tortrix* spp. |
| CryIA(a) | *Trichoplusia ni* |
| CryIA(a) | *Agriotes* spp. |
| CryIA(a) | *Anthonomus grandis* |
| CryIA(a) | *Curculio* spp. |
| CryIA(a) | *Diabrotica balteata* |
| CryIA(a) | *Leptinotarsa* spp. |
| CryIA(a) | *Lissorhoptrus* spp. |
| CryIA(a) | *Otiorhynchus* spp. |
| CryIA(a) | *Aleurothrixus* spp. |
| CryIA(a) | *Aleyrodes* spp. |
| CryIA(a) | *Aonidiella* spp. |
| CryIA(a) | *Aphididea* spp. |
| CryIA(a) | *Aphis* spp. |
| CryIA(a) | *Bemisia tabaci* |
| CryIA(a) | *Empoasca* spp. |
| CryIA(a) | *Mycus* spp. |
| CryIA(a) | *Nephotettix* spp. |
| CryIA(a) | *Nilaparvata* spp. |
| CryIA(a) | *Pseudococcus* spp. |
| CryIA(a) | *Psylla* spp. |
| CryIA(a) | *Quadraspidiotus* spp. |
| CryIA(a) | *Schizaphis* spp. |
| CryIA(a) | *Trialeurodes* spp. |
| CryIA(a) | *Lyriomyza* spp. |
| CryIA(a) | *Oscinella* spp. |
| CryIA(a) | *Phorbia* spp. |
| CryIA(a) | *Frankliniella* spp. |
| CryIA(a) | *Thrips* spp. |
| CryIA(a) | *Scirtothrips aurantii* |
| CryIA(a) | *Aceria* spp. |
| CryIA(a) | *Aculus* spp. |
| CryIA(a) | *Brevipaipus* spp. |
| CryIA(a) | *Panonychus* spp. |
| CryIA(a) | *Phyllocoptruta* spp. |
| CryIA(a) | *Tetranychus* spp. |

TABLE 2-continued

| AP | Control of |
|---|---|
| CryIA(a) | *Heterodera* spp. |
| CryIA(a) | *Meloidogyne* spp. |
| CryIA(b) | *Adoxophyes* spp |
| CryIA(b) | *Agrotis* spp |
| CryIA(b) | *Alabama argillaceae* |
| CryIA(b) | *Anticarsia gemmatalis* |
| CryIA(b) | *Chilo* spp. |
| CryIA(b) | *Ciysia ambiguella* |
| CryIA(b) | *Crocidolomia binotaiis* |
| CryIA(b) | *Cydia* spp. |
| CryIA(b) | *Diparopsis castanea* |
| CryIA(b) | *Earias* spp. |
| CryIA(b) | *Ephestia* spp. |
| CryIA(b) | *Heliothis* spp. |
| CryIA(b) | *Hellula undalis* |
| CryIA(b) | *Keiferia lycopersicella* |
| CryIA(b) | *Leucoptera scitella* |
| CryIA(b) | *Lithocollethis* spp. |
| CryIA(b) | *Lobesia botrana* |
| CryIA(b) | *Ostrinia nubilalis* |
| CryIA(b) | *Pandemis* spp. |
| CryIA(b) | *Pectinophora gossyp.* |
| CryIA(b) | *Phyllocnistis citrella* |
| CryIA(b) | *Pieris* spp. |
| CryIA(b) | *Plutelia xyiostella* |
| CryIA(b) | *Scirpophaga* spp. |
| CryIA(b) | *Sesamia* spp. |
| CryIA(b) | *Sparganothis* spp. |
| CryIA(b) | *Spodoptera* spp. |
| CryIA(b) | *Tortrix* spp. |
| CryIA(b) | *Trichoplusia ni* |
| CryIA(b) | *Agriotes* spp. |
| CryIA(b) | *Anthonomus grandis* |
| CryIA(b) | *Curculio* spp. |
| CryIA(b) | *Diabrotica balteata* |
| CryIA(b) | *Leptinotarsa* spp. |
| CryIA(b) | *Lissorhoptrus* spp. |
| CryIA(b) | *Otiorhynchus* spp. |
| CryIA(b) | *Aleurothrixus* spp. |
| CryIA(b) | *Aleyrodes* spp. |
| CryIA(b) | *Aonidiella* spp. |
| CryIA(b) | *Aphididae* spp. |
| CryIA(b) | *Aphis* spp. |
| CryIA(b) | *Bemisia tabaci* |
| CryIA(b) | *Empoasca* spp. |
| CryIA(b) | *Mycus* spp. |
| CryIA(b) | *Nephotettix* spp. |
| CryIA(b) | *Nilaparvata* spp. |
| CryIA(b) | *Pseudococcus* spp. |
| CryIA(b) | *Psylla* spp. |
| CryIA(b) | *Quadraspidiotus* spp. |
| CryIA(b) | *Schizaphis* spp. |
| CryIA(b) | *Trialeurodes* spp. |
| CryIA(b) | *Lyriomyza* spp. |
| CryIA(b) | *Oscinella* spp. |
| CryIA(b) | *Phorbia* spp. |
| CryIA(b) | *Frankliniella* spp. |
| CryIA(b) | *Thrips* spp. |
| CryIA(b) | *Scirtothrips aurantii* |
| CryIA(b) | *Aceria* spp. |
| CryIA(b) | *Aculus* spp. |
| CryIA(b) | *Brevipalpus* spp. |
| CryIA(b) | *Panonychus* spp. |
| CryIA(b) | *Phyllocoptruta* spp. |
| CryIA(b) | *Tetranychus* spp. |
| CryIA(b) | *Heterodera* spp. |
| CryIA(b) | *Meloidogyne* spp. |
| CryIA(c) | *Adoxophyes* spp. |
| CryIA(c) | *Agrotis* spp. |
| CryIA(c) | *Alabama argillaceae* |
| CryIA(c) | *Anticarsia gemmatalis* |
| CryIA(c) | *Chilo* spp. |
| CryIA(c) | *Ciysia ambiguella* |
| CryIA(c) | *Crocidolomia binotalis* |
| CryIA(c) | *Cydia* spp. |
| CryIA(c) | *Diparopsis castanea* |
| CryIA(c) | *Earias* spp. |
| CryIA(c) | *Ephestia* spp. |
| CryIA(c) | *Heliothis* spp. |
| CryIA(c) | *Hellula undalis* |
| CryIA(c) | *Keiferia lycopersicella* |
| CryIA(c) | *Leucoptera scitella* |
| CryIA(c) | *Lithocollethis* spp. |
| CryIA(c) | *Lobesia botrana* |
| CryIA(c) | *Ostrinia nubilalis* |
| CryIA(c) | *Pandemis* spp. |
| CryIA(c) | *Pectinophora gossypielia.* |
| CryIA(c) | *Phyllocnistis citrella* |
| CryIA(c) | *Pieris* spp. |
| CryIA(c) | *Plutella xyiostella* |
| CryIA(c) | *Scirpophaga* spp. |
| CryIA(c) | *Sesamia* spp. |
| CryIA(c) | *Sparganothis* spp. |
| CryIA(c) | *Spodoptera* spp. |
| CryIA(c) | *Tortrix* spp. |
| CryIA(c) | *Trichoplusia ni* |
| CryIA(c) | *Agriotes* spp. |
| CryIA(c) | *Anthonomus grandis* |
| CryIA(c) | *Curculio* spp. |
| CryIA(c) | *Diabrotica baiteata* |
| CryIA(c) | *Leptinotarsa* spp. |
| CryIA(c) | *Lissorhoptrus* spp. |
| CryIA(c) | *Otiorhynchus* spp. |
| CryIA(c) | *Aleurothrixus* spp. |
| CryIA(c) | *Aleyrodes* spp. |
| CryIA(c) | *Aonidiella* spp. |
| CryIA(c) | *Aphididae* spp. |
| CryIA(c) | *Aphis* spp. |
| CryIA(c) | *Bemisia tabaci* |
| CryIA(c) | *Empoasca* spp. |
| CryIA(c) | *Mycus* spp. |
| CryIA(c) | *Nephotettix* spp. |
| CryIA(c) | *Nilaparvata* spp. |
| CryIA(c) | *Pseudococcus* spp. |
| CryIA(c) | *Psylla* spp. |
| CryIA(c) | *Quadraspidiotus* spp. |
| CryIA(c) | *Schizaphis* spp. |
| CryIA(c) | *Trialeurodes* spp. |
| CryIA(c) | *Lyriomyza* spp. |
| CryIA(c) | *Oscinelia* spp. |
| CryIA(c) | *Phorbia* spp. |
| CryIA(c) | *Frankliniella* spp. |
| CryIA(c) | *Thrips* spp. |
| CryIA(c) | *Scirtothrips aurantii* |
| CryIA(c) | *Aceria* spp. |
| CryIA(c) | *Aculus* spp. |
| CryIA(c) | *Brevipalpus* spp. |
| CryIA(c) | *Panonychus* spp. |
| CryIA(c) | *Phyllocoptruta* spp. |
| CryIA(c) | *Tetranychus* spp. |
| CryIA(c) | *Heterodera* spp. |
| CryIA(c) | *Meloidogyne* spp. |
| CryIIA | *Adoxophyes* spp. |
| CryIIA | *Agrotis* spp. |
| CryIIA | *Alabama argillaceae* |
| CryIIA | *Anticarsia gemmatalis* |
| CryIIA | *Chilo* spp. |
| CryIIA | *Clysia ambiguella* |
| CryIIA | *Crocidolomia binotalis* |
| CryIIA | *Cydia* spp. |
| CryIIA | *Diparopsis castanea* |
| CryIIA | *Earias* spp. |
| CryIIA | *Ephestia* spp. |
| CryIIA | *Heliothis* spp. |
| CryIIA | *Hellula undalis* |
| CryIIA | *Keiferia lycopersicella* |
| CryIIA | *Leucoptera scitella* |
| CryIIA | *Lithocoliethis* spp. |
| CryIIA | *Lobesia botrana* |
| CryIIA | *Ostrinia nubilalis* |
| CryIIA | *Pandemis* spp. |
| CryIIA | *Pectinophora gossyp.* |
| CryIIA | *Phyllocnistis citrella* |
| CryIIA | *Pieris* spp. |
| CryIIA | *Plutella xylostella* |
| CryIIA | *Scirpophaga* spp. |

TABLE 2-continued

| AP | Control of |
|---|---|
| CryIIA | *Sesamia* spp. |
| CryIIA | *Sparganothis* spp. |
| CryIIA | *Spodoptera* spp. |
| CryIIA | *Tortrix* spp. |
| CryIIA | *Trichoplusia ni* |
| CryIIA | *Agriotes* spp. |
| CryIIA | *Anthonomus grandis* |
| CryIIA | *Curculio* spp. |
| CryIIA | *Diabrotica balteata* |
| CryIIA | *Leptinotarsa* spp. |
| CryIIA | *Lissorhoptrus* spp. |
| CryIIA | *Otiorhynchus* spp. |
| CryIIA | *Aleurothrixus* spp. |
| CryIIA | *Aleyrodes* spp. |
| CryIIA | *Aonidiella* spp. |
| CryIIA | *Aphididae* spp. |
| CryIIA | *Aphis* spp. |
| CryIIA | *Bemisia tabaci* |
| CryIIA | *Empoasca* spp. |
| CryIIA | *Mycus* spp. |
| CryIIA | *Nephotettix* spp. |
| CryIIA | *Nilaparvata* spp. |
| CryIIA | *Pseudococcus* spp. |
| CryIIA | *Psyila* spp. |
| CryIIA | *Quadraspidiotus* spp. |
| CryIIA | *Schizaphis* spp. |
| CryIIA | *Trialeurodes* spp. |
| CryIIA | *Lyriomyza* spp. |
| CryIIA | *Oscinella* spp. |
| CryIIA | *Phorbia* spp. |
| CryIIA | *Frankliniella* spp. |
| CryIIA | *Thrips* spp. |
| CryIIA | *Scirtothrips aurantii* |
| CryIIA | *Aceria* spp. |
| CryIIA | *Acutus* spp. |
| CryIIA | *Brevipalpus* spp. |
| CryIIA | *Panonychus* spp. |
| CryIIA | *Phyllocoptruta* spp. |
| CryIIA | *Tetranychus* spp. |
| CryIIA | *Heterodera* spp. |
| CryIIA | *Meloidogyne* spp. |
| CryIIIA | *Adoxophyes* spp. |
| CryIIIA | *Agrotis* spp. |
| CryIIIA | *Alabama argiiiaceae* |
| CryIIIA | *Anticarsia gemmataiis* |
| CryIIIA | *Chilo* spp. |
| CryIIIA | *Ciysia ambiguelia* |
| CryIIIA | *Crocodolomia binotalis* |
| CryIIIA | *Cydia* spp. |
| CryIIIA | *Diparopsis castanea* |
| CryIIIA | *Earias* spp. |
| CryIIIA | *Ephestia* spp. |
| CryIIIA | *Heliothis* spp. |
| CryIIIA | *Hellula undalis* |
| CryIIIA | *Keiferia lycopersicella* |
| CryIIIA | *Leucoptera scitella* |
| CryIIIA | *Lithocollethis* spp. |
| CryIIIA | *Lobesia botrana* |
| CryIIIA | *Ostrinia nubilalis* |
| CryIIIA | *Pandemis* spp. |
| CryIIIA | *Pectinophora gossyp.* |
| CryIIIA | *Phyllocnistis citrella* |
| CryIIIA | *Pieris* spp. |
| CryIIIA | *Plutella xylostella* |
| CryIIIA | *Scirpophaga* spp. |
| CryIIIA | *Sesamia* spp. |
| CryIIIA | *Sparganothis* spp. |
| CryIIIA | *Spodoptera* spp. |
| CryIIIA | *Tortrix* spp. |
| CryIIIA | *Trichoplusia ni* |
| CryIIIA | *Agriotes* spp. |
| CryIIIA | *Anthonomus grandis* |
| CryIIIA | *Curculio* spp. |
| CryIIIA | *Diabrotica balteata* |
| CryIIIA | *Leptinotarsa* spp. |
| CryIIIA | *Lissorhoptrus* spp. |
| CryIIIA | *Otiorhynchus* spp. |
| CryIIIA | *Aleurothrixus* spp. |
| CryIIIA | *Aleyrodes* spp. |
| CryIIIA | *Aonidiella* spp. |
| CryIIIA | *Aphididae* spp. |
| CryIIIA | *Aphis* spp. |
| CryIIIA | *Bemisia tabaci* |
| CryIIIA | *Empoasca* spp. |
| CryIIIA | *Mycus* spp. |
| CryIIIA | *Nephotettix* spp. |
| CryIIIA | *Nilaparvata* spp. |
| CryIIIA | *Pseudococcus* spp. |
| CryIIIA | *Psylla* spp. |
| CryIIIA | *Quadraspidiotus* spp. |
| CryIIIA | *Schizaphis* spp. |
| CryIIIA | *Trialeurodes* spp. |
| CryIIIA | *Lyriomyza* spp. |
| CryIIIA | *Oscinella* spp. |
| CryIIIA | *Phorbia* spp. |
| CryIIIA | *Frankliniella* spp. |
| CryIIIA | *Thrips* spp. |
| CryIIIA | *Scirtothrips aurantii* |
| CryIIIA | *Aceria* spp. |
| CryIIIA | *Aculus* spp. |
| CryIIIA | *Brevipalpus* spp. |
| CryIIIA | *Panonychus* spp. |
| CryIIIA | *Phyllocoptruta* spp. |
| CryIIIA | *Tetranychus* spp. |
| CryIIIA | *Heterodera* spp. |
| CryIIIA | *Meloidogyne* spp. |
| CryIIIB2 | *Adoxophyes* spp. |
| CryIIIB2 | *Agrotis* spp. |
| CryIIIB2 | *Alabama argiilaceae* |
| CryIIIB2 | *Anticarsia gemmatalis* |
| CryIIIB2 | *Chilo* spp. |
| CryIIIB2 | *Clysia ambiguella* |
| CryIIIB2 | *Crocidolomia binotaiis* |
| CryIIIB2 | *Cydia* spp. |
| CryIIIB2 | *Diparopsis castanea* |
| CryIIIB2 | *Earias* spp. |
| CryIIIB2 | *Ephestia* spp. |
| CryIIIB2 | *Heliothis* spp. |
| CryIIIB2 | *Hellula undalis* |
| CryIIIB2 | *Keiferia lycopersicella* |
| CryIIIB2 | *Leucoptera sectelia* |
| CryIIIB2 | *Lithocollethis* spp. |
| CryIIIB2 | *Lobesia botrana* |
| CryIIIB2 | *Ostrinia nubilalis* |
| CryIIIB2 | *Pandemis* spp. |
| CryIIIB2 | *Pectinophora gossyp.* |
| CryIIIB2 | *Phyllocnistis citrella* |
| CryIIIB2 | *Pieris* spp. |
| CryIIIB2 | *Plutella xylostella* |
| CryIIIB2 | *Scirpophaga* spp. |
| CryIIIB2 | *Sesamia* spp. |
| CryIIIB2 | *Sparganothis* spp. |
| CryIIIB2 | *Spodoptera* spp. |
| CryIIIB2 | *Tortrix* spp. |
| CryIIIB2 | *Trichoplusia ni* |
| CryIIIB2 | *Agriotes* spp. |
| CryIIIB2 | *Anthonomus grandis* |
| CryIIIB2 | *Curculio* spp. |
| CryIIIB2 | *Diabrotica balteata* |
| CryIIIB2 | *Leptinotarsa* spp. |
| CryIIIB2 | *Lissorhoptrus* spp. |
| CryIIIB2 | *Otiorhynchus* spp. |
| CryIIIB2 | *Aleurothrixus* spp. |
| CryIIIB2 | *Aleyrodes* spp. |
| CryIIIB2 | *Aonidiella* spp. |
| CryIIIB2 | *Aphididae* spp. |
| CryIIIB2 | *Aphis* spp. |
| CryIIIB2 | *Bemisia tabaci* |
| CryIIIB2 | *Empoasca* spp. |
| CryIIIB2 | *Mycus* spp. |
| CryIIIB2 | *Nephotettix* spp. |
| CryIIIB2 | *Nilaparvata* spp. |
| CryIIIB2 | *Pseudococcus* spp. |
| CryIIIB2 | *Psylla* spp. |
| CryIIIB2 | *Quadraspidiotus* spp. |
| CryIIIB2 | *Schizaphis* spp. |

TABLE 2-continued

| AP | Control of |
|---|---|
| CryIIIB2 | Trialeurodes spp. |
| CryIIIB2 | Lyriomyza spp. |
| CryIIIB2 | Oscinella spp. |
| CryIIIB2 | Phorbia spp. |
| CryIIIB2 | Frankliniella spp. |
| CryIIIB2 | Thrips spp. |
| CryIIIB2 | Scirtothrips aurantii |
| CryIIIB2 | Aceria spp. |
| CryIIIB2 | Acutus spp. |
| CryIIIB2 | Brevipalpus spp. |
| CryIIIB2 | Panonychus spp. |
| CryIIIB2 | Phyllocoptruta spp. |
| CryIIIB2 | Tetranychus spp. |
| CryIIIB2 | Heterodera spp. |
| CryIIIB2 | Meloidogyne spp. |
| CytA | Adoxophyes spp. |
| CytA | Agrotis spp. |
| CytA | Alabama argiilaceae |
| CytA | Anticarsia gemmatalis |
| CytA | Chilo spp. |
| CytA | Clysia ambiguella |
| CytA | Crocidolomia binotaiis |
| CytA | Cydia spp. |
| CytA | Diparopsis castanea |
| CytA | Earias spp. |
| CytA | Ephestia spp. |
| CytA | Heliothis spp. |
| CytA | Hellula undalis |
| CytA | Keiferia lycopersicella |
| CytA | Leucoptera scitelia |
| CytA | Lithocollethis spp. |
| CytA | Lobesia botrana |
| CytA | Ostrinia nubilalis |
| CytA | Pandemis spp. |
| CytA | Pectinophora gossyp. |
| CytA | Phyllocnistis citrella |
| CytA | Pieris spp. |
| CytA | Plutella xylostella |
| CytA | Scirpophaga spp. |
| CytA | Sesamia spp. |
| CytA | Sparganothis spp. |
| CytA | Spodoptera spp. |
| CytA | Tortrix spp. |
| CytA | Trichoplusia ni |
| CytA | Agriotes spp. |
| CytA | Anthonomus grandis |
| CytA | Curculio spp. |
| CytA | Diabrotica balteata |
| CytA | Leptinotarsa spp. |
| CytA | Lissorhoptrus spp. |
| CytA | Otiorhynchus spp. |
| CytA | Aleurothrixus spp. |
| CytA | Aleyrodes spp. |
| CytA | Aonidiella spp. |
| CytA | Aphididae spp. |
| CytA | Aphis spp. |
| CytA | Bemisia tabaci |
| CytA | Empoasca spp. |
| CytA | Mycus spp. |
| CytA | Nephotettix spp. |
| CytA | Nilaparvata spp. |
| CytA | Pseudococcus spp. |
| CytA | Psylla spp. |
| CytA | Quadraspidiotus spp. |
| CytA | Schizaphis spp. |
| CytA | Trialeurodes spp. |
| CytA | Lyriomyza spp. |
| CytA | Oscinella spp. |
| CytA | Phorbia spp. |
| CytA | Frankliniella spp. |
| CytA | Thrips spp. |
| CytA | Scirtothrips aurantii |
| CytA | Aceria spp. |
| CytA | Acutus spp. |
| CytA | Brevipalpus spp. |
| CytA | Panonychus spp. |
| CytA | Phyllocoptruta spp. |
| CytA | Tetranychus spp. |

TABLE 2-continued

| AP | Control of |
|---|---|
| CytA | Heterodera spp. |
| CytA | Meloidogyne spp. |
| VIP3 | Adoxophyes spp. |
| VIP3 | Agrotis spp. |
| VIP3 | Alabama argillaceae |
| VIP3 | Anticarsia gemmatalis |
| VIP3 | Chilo spp. |
| VIP3 | Clysia ambiguella |
| VIP3 | Crocidolomia binotalis |
| VIP3 | Cydia spp. |
| VIP3 | Diparopsis castanea |
| VIP3 | Earias spp. |
| VIP3 | Ephestia spp. |
| VIP3 | Heliothis spp. |
| VIP3 | Hellula undalis |
| VIP3 | Keiferia lycopersicella |
| VIP3 | Leucoptera scitella |
| VIP3 | Lithocollethis spp. |
| VIP3 | Lobesia botrana |
| VIP3 | Ostrinia nubilalis |
| VIP3 | Pandemis spp. |
| VIP3 | Pectinophora gossyp. |
| VIP3 | Phyllocnistis citrella |
| VIP3 | Pieris spp. |
| VIP3 | Piutella xylostella |
| VIP3 | Scirpophaga spp. |
| VIP3 | Sesamia spp. |
| VIP3 | Sparganothis spp. |
| VIP3 | Spodoptera spp. |
| VIP3 | Tortrix spp. |
| VIP3 | Trichoplusia ni |
| VIP3 | Agriotes spp. |
| VIP3 | Anthonomus grandis |
| VIP3 | Curculio spp. |
| VIP3 | Diabrotica balteata |
| VIP3 | Leptinotarsa spp. |
| VIP3 | Lissorhoptrus spp. |
| VIP3 | Otiorhynchus spp. |
| VIP3 | Aleurothrixus spp. |
| VIP3 | Aleyrodes spp. |
| VIP3 | Aonidiella spp. |
| VIP3 | Aphididae spp. |
| VIP3 | Aphis spp. |
| VIP3 | Bemisia tabaci |
| VIP3 | Empoasca spp. |
| VIP3 | Mycus spp. |
| VIP3 | Nephotettix spp. |
| VIP3 | Niiaparvata spp. |
| VIP3 | Pseudococcus spp. |
| VIP3 | Psylla spp. |
| VIP3 | Quadraspidiotus spp. |
| VIP3 | Schizaphis spp. |
| VIP3 | Trialeurodes spp. |
| VIP3 | Lyriomyza spp. |
| VIP3 | Oscinella spp. |
| VIP3 | Phorbia spp. |
| VIP3 | Frankliniella spp. |
| VIP3 | Thrips spp. |
| VIP3 | Scirtothrips aurantii |
| VIP3 | Aceria spp. |
| VIP3 | Acutus spp. |
| VIP3 | Brevipalpus spp. |
| VIP3 | Panonychus spp. |
| VIP3 | Phyllocoptruta spp. |
| VIP3 | Tetranychus spp. |
| VIP3 | Heterodera spp. |
| VIP3 | Meloidogyne spp. |
| GL | Adoxophyes spp. |
| GL | Agrotis spp. |
| GL | Alabama argillaceae |
| GL | Anticarsia gemmatalis |
| GL | Chilo spp. |
| GL | Clysia ambiguella |
| GL | Crocidolomia binotaiis |
| GL | Cydia spp. |
| GL | Diparopsis castanea |
| GL | Earias spp. |
| GL | Ephestia spp. |

TABLE 2-continued

| AP | Control of |
|----|------------|
| GL | *Heliothis* spp. |
| GL | *Hellula undalis* |
| GL | *Keiferia lycopersicella* |
| GL | *Leucoptera scitella* |
| GL | *Lithocollethis* spp. |
| GL | *Lobesia botrana* |
| GL | *Ostrinia nubilalis* |
| GL | *Pandemis* spp. |
| GL | *Pectinophora gossyp.* |
| GL | *Phyliocnistis citrella* |
| GL | *Pieris* spp. |
| GL | *Plutella xylostella* |
| GL | *Scirpophaga* spp. |
| GL | *Sesamia* spp. |
| GL | *Sparganothis* spp. |
| GL | *Spodoptera* spp. |
| GL | *Tortrix* spp. |
| GL | *Trichoplusia ni* |
| GL | *Agriotes* spp. |
| GL | *Anthonomus grandis* |
| GL | *Curculio* spp. |
| GL | *Diabrotica balteata* |
| GL | *Leptinotarsa* spp. |
| GL | *Lissorhoptrus* spp. |
| GL | *Otiorhynchus* spp. |
| GL | *Aleurothrixus* spp. |
| GL | *Aleyrodes* spp. |
| GL | *Aonidiella* spp. |
| GL | *Aphididae* spp. |
| GL | *Aphis* spp. |
| GL | *Bemisia tabaci* |
| GL | *Empoasca* spp. |
| GL | *Mycus* spp. |
| GL | *Nephotettix* spp. |
| GL | *Nilaparvata* spp. |
| GL | *Pseudococcus* spp. |
| GL | *Psylia* spp. |
| GL | *Quadraspidiotus* spp. |
| GL | *Schizaphis* spp. |
| GL | *Trialeurodes* spp. |
| GL | *Lyriomyza* spp. |
| GL | *Oscinella* spp. |
| GL | *Phorbia* spp. |
| GL | *Frankliniella* spp. |
| GL | *Thrips* spp. |
| GL | *Scirtothrips aurantii* |
| GL | *Aceria* spp. |
| GL | *Aculus* spp. |
| GL | *Brevipalpus* spp. |
| GL | *Panonychus* spp. |
| GL | *Phyliocoptruta* spp. |
| GL | *Tetranychus* spp. |
| GL | *Heterodera* spp. |
| GL | *Meioidogyne* spp. |
| PL | *Adoxophyes* spp. |
| PL | *Agrotis* spp. |
| PL | *Alabama argillaceae* |
| PL | *Anticarsia gemmatalis* |
| PL | *Chilo* spp. |
| PL | *Clysia ambiguella* |
| PL | *Crocidolomia binotalis* |
| PL | *Cydia* spp. |
| PL | *Diparopsis castanea* |
| PL | *Earias* spp. |
| PL | *Ephestia* spp. |
| PL | *Heliothis* spp. |
| PL | *Hellula undaiis* |
| PL | *Keiferia lycopersicella* |
| PL | *Leucoptera scitella* |
| PL | *Lithocollethis* spp. |
| PL | *Lobesia botrana* |
| PL | *Ostrinia nubilalis* |
| PL | *Pandemis* spp. |
| PL | *Pectinophora gossyp.* |
| PL | *Phyllocnistis citrella* |
| PL | *Pieris* spp. |
| PL | *Plutella xylostella* |
| PL | *Scirpophaga* spp. |
| PL | *Sesamia* spp. |
| PL | *Sparganothis* spp. |
| PL | *Spodoptera* spp. |
| PL | *Tortrix* spp. |
| PL | *Trichoplusia ni* |
| PL | *Agriotes* spp. |
| PL | *Anthonomus grandis* |
| PL | *Curculio* spp. |
| PL | *Diabrotica balteata* |
| PL | *Leptinotarsa* spp. |
| PL | *Lissorhoptrus* spp. |
| PL | *Otiorhynchus* spp. |
| PL | *Aleurothrixus* spp. |
| PL | *Aleyrodes* spp. |
| PL | *Aonidiella* spp. |
| PL | *Aphididae* spp. |
| PL | *Aphis* spp. |
| PL | *Bemisia tabaci* |
| PL | *Empoasca* spp. |
| PL | *Mycus* spp. |
| PL | *Nephotettix* spp. |
| PL | *Nilaparvata* spp. |
| PL | *Pseudococcus* spp. |
| PL | *Psylla* spp. |
| PL | *Quadraspidiotus* spp. |
| PL | *Schizaphis* spp. |
| PL | *Trialeurodes* spp. |
| PL | *Lyriomyza* spp. |
| PL | *Oscinella* spp. |
| PL | *Phorbia* spp. |
| PL | *Frankliniella* spp. |
| PL | *Thrips* spp. |
| PL | *Scirtothrips aurantii* |
| PL | *Aceria* spp. |
| PL | *Aculus* spp. |
| PL | *Brevipalpus* spp. |
| PL | *Panonychus* spp. |
| PL | *Phyllocoptruta* spp. |
| PL | *Tetranychus* spp. |
| PL | *Heterodera* spp. |
| PL | *Meloidogyne* spp. |
| XN | *Adoxophyes* spp. |
| XN | *Agrotis* spp. |
| XN | *Alabama argiliaceae* |
| XN | *Anticarsia gemmatalis* |
| XN | *Chilo* spp. |
| XN | *Clysia ambiguella* |
| XN | *Crocidolomia binotalis* |
| XN | *Cydia* spp. |
| XN | *Diparopsis castanea* |
| XN | *Earias* spp. |
| XN | *Ephestia* spp. |
| XN | *Heliothis* spp. |
| XN | *Helluia undaiis* |
| XN | *Keiferia lycopersicella* |
| XN | *Leucoptera scitella* |
| XN | *Lithocollethis* spp. |
| XN | *Lobesia botrana* |
| XN | *Ostrinia nubilalis* |
| XN | *Pandemis* spp. |
| XN | *Pectinophora gossyp.* |
| XN | *Phyllocnistis citrella* |
| XN | *Pieris* spp. |
| XN | *Plutella xylostella* |
| XN | *Scirpophaga* spp. |
| XN | *Sesamia* spp. |
| XN | *Sparganothis* spp. |
| XN | *Spodoptera* spp. |
| XN | *Tortrix* spp. |
| XN | *Trichoplusia ni* |
| XN | *Agriotes* spp. |
| XN | *Anthonomus grandis* |
| XN | *Curculio* spp. |
| XN | *Diabrotica balteata* |
| XN | *Leptinotarsa* spp. |
| XN | *Lissorhoptrus* spp. |
| XN | *Otiorhynchus* spp. |
| XN | *Aleurothrixus* spp. |

TABLE 2-continued

| AP | Control of |
|---|---|
| XN | *Aleyrodes* spp. |
| XN | *Aonidiella* spp. |
| XN | *Aphididae* spp. |
| XN | *Aphis* spp. |
| XN | *Bemisia tabaci* |
| XN | *Empoasca* spp. |
| XN | *Mycus* spp. |
| XN | *Nephotettix* spp. |
| XN | *Nilaparvata* spp. |
| XN | *Pseudococcus* spp. |
| XN | *Psylla* spp. |
| XN | *Quadraspidiotus* spp. |
| XN | *Schizaphis* spp. |
| XN | *Trialeurodes* spp. |
| XN | *Lyriomyza* spp. |
| XN | *Oscinella* spp. |
| XN | *Phorbia* spp. |
| XN | *Frankliniella* spp. |
| XN | *Thrips* spp. |
| XN | *Scirtothrips aurantii* |
| XN | *Aceria* spp. |
| XN | *Aculus* spp. |
| XN | *Brevipalpus* spp. |
| XN | *Panonychus* spp. |
| XN | *Phyllocoptruta* spp. |
| XN | *Tetranychus* spp. |
| XN | *Heterodera* spp. |
| XN | *Meloidogyne* spp. |
| Plnh. | *Adoxophyes* spp. |
| Plnh. | *Agrotis* spp. |
| Plnh. | *Alabama argiliaceae* |
| Plnh. | *Anticarsia gemmatalis* |
| Plnh. | *Chilo* spp. |
| Plnh. | *Clysia ambiguella* |
| Plnh. | *Crocidolomia binotalis* |
| Plnh. | *Cydia* spp. |
| Plnh. | *Diparopsis castanea* |
| Plnh. | *Earias* spp. |
| Plnh. | *Ephestia* spp. |
| Plnh. | *Heliothis* spp. |
| Plnh. | *Heliuia undalis* |
| Plnh. | *Keiferia lycopersicella* |
| Plnh. | *Leucoptera scitella* |
| Plnh. | *Lithocollethis* spp. |
| Plnh. | *Lobesia botrana* |
| Plnh. | *Ostrinia nubilalis* |
| Plnh. | *Pandemis* spp. |
| Plnh. | *Pectinophora gossyp.* |
| Plnh. | *Phyllocnistis citrelia* |
| Plnh. | *Pieris* spp. |
| Plnh. | *Plutella xylostella* |
| Plnh. | *Scirpophaga* spp. |
| Plnh. | *Sesamia* spp. |
| Plnh. | *Sparganothis* spp. |
| Plnh. | *Spodoptera* spp. |
| Plnh. | *Tortrix* spp. |
| Plnh. | *Trichoplusia ni* |
| Plnh. | *Agriotes* spp. |
| Plnh. | *Anthonomus grandis* |
| Plnh. | *Curculio* spp. |
| Plnh. | *Diabrotica balteata* |
| Plnh. | *Leptinotarsa* spp. |
| Plnh. | *Lissorhoptrus* spp. |
| Plnh. | *Otiorhynchus* spp. |
| Plnh. | *Aleurothrixus* spp. |
| Plnh. | *Aleyrodes* spp. |
| Plnh. | *Aonidiella* spp. |
| Plnh. | *Aphididae* spp. |
| Plnh. | *Aphis* spp. |
| Plnh. | *Bemisia tabaci* |
| Plnh. | *Empoasca* spp. |
| Plnh. | *Mycus* spp. |
| Plnh. | *Nephotettix* spp. |
| Plnh. | *Nilaparvata* spp. |
| Plnh. | *Pseudococcus* spp. |
| Plnh. | *Psylla* spp. |
| Plnh. | *Quadraspidiotus* spp. |
| Plnh. | *Schizaphis* spp. |
| Plnh. | *Trialeurodes* spp. |
| Plnh. | *Lyriomyza* spp. |
| Plnh. | *Oscinella* spp. |
| Plnh. | *Phorbia* spp. |
| Plnh. | *Frankliniella* spp. |
| Plnh. | *Thrips* spp. |
| Plnh. | *Scirtothrips aurantii* |
| Plnh. | *Aceria* spp. |
| Plnh. | *Acutus* spp. |
| Plnh. | *Brevipalpus* spp. |
| Plnh. | *Panonychus* spp. |
| Plnh. | *Phyllocoptruta* spp. |
| Plnh. | *Tetranychus* spp. |
| Plnh. | *Heterodera* spp. |
| Plnh. | *Meloidogyne* spp. |
| PLec. | *Adoxophyes* spp. |
| PLec. | *Agrotis* spp. |
| PLec. | *Alabama argillaceae* |
| PLec. | *Anticarsia gemmatalis* |
| PLec. | *Chilo* spp. |
| PLec. | *Clysia ambiguella* |
| PLec. | *Crocidolomia binotalis* |
| PLec. | *Cydia* spp. |
| PLec. | *Diparopsis castanea* |
| PLec. | *Earias* spp. |
| PLec. | *Ephestia* spp. |
| PLec. | *Heliothis* spp. |
| PLec. | *Hellula undalis* |
| PLec. | *Keiferia lycopersicella* |
| PLec. | *Leucoptera scitella* |
| PLec. | *Lithocollethis* spp. |
| PLec. | *Lobesia botrana* |
| PLec. | *Ostrinia nubilalis* |
| PLec. | *Pandemis* spp. |
| PLec. | *Pectinophora gossyp.* |
| PLec. | *Phyllocnistis citrella* |
| PLec. | *Pieris* spp. |
| PLec. | *Plutella xylostella* |
| PLec. | *Scirpophaga* spp. |
| PLec. | *Sesamia* spp. |
| PLec. | *Sparganothis* spp. |
| PLec. | *Spodoptera* spp. |
| PLec. | *Tortrix* spp. |
| PLec. | *Trichoplusia ni* |
| PLec. | *Agriotes* spp. |
| PLec. | *Anthonomus grandis* |
| PLec. | *Curculio* spp. |
| PLec. | *Diabrotica balteata* |
| PLec. | *Leptinotarsa* spp. |
| PLec. | *Lissorhoptrus* spp. |
| PLec. | *Otiorhynchus* spp. |
| PLec. | *Aleurothrixus* spp. |
| PLec. | *Aleyrodes* spp. |
| PLec. | *Aonidiella* spp. |
| PLec. | *Aphididae* spp. |
| PLec. | *Aphis* spp. |
| PLec. | *Bemisia tabaci* |
| PLec. | *Empoasca* spp. |
| PLec. | *Mycus* spp. |
| PLec. | *Nephotettix* spp. |
| PLec. | *Nilaparvata* spp. |
| PLec. | *Pseudococcus* spp. |
| PLec. | *Psylia* spp. |
| PLec. | *Quadraspidiotus* spp. |
| PLec. | *Schizaphis* spp. |
| PLec. | *Trialeurodes* spp. |
| PLec. | *Lyriomyza* spp. |
| PLec. | *Oscinella* spp. |
| PLec. | *Phorbia* spp. |
| PLec. | *Frankliniella* spp. |
| PLec. | *Thrips* spp. |
| PLec. | *Scirtothrips aurantii* |
| PLec. | *Aceria* spp. |
| PLec. | *Aculus* spp. |
| PLec. | *Brevipalpus* spp. |
| PLec. | *Panonychus* spp. |
| PLec. | *Phyllocoptruta* spp. |
| PLec. | *Tetranychus* spp. |

TABLE 2-continued

| AP | Control of |
|---|---|
| PLec. | *Heterodera* spp. |
| PLec. | *Meloidogyne* spp. |
| Aggl. | *Adoxophyes* spp. |
| Aggl. | *Agrotis* spp. |
| Aggl. | *Alabama argillaceae* |
| Aggl. | *Anticarsia gemmatalis* |
| Aggl. | *Chilo* spp. |
| Aggl. | *Clysia ambiguella* |
| Aggl. | *Crocidolomia binotalis* |
| Aggl. | *Cydia* spp. |
| Aggl. | *Diparopsis castanea* |
| Aggl. | *Earias* spp. |
| Aggl. | *Ephestia* spp. |
| Aggl. | *Heliothis* spp. |
| Aggl. | *Hellula undalis* |
| Aggl. | *Keiferia lycopersicella* |
| Aggl. | *Leucoptera scitella* |
| Aggl. | *Lithocollethis* spp. |
| Aggl. | *Lobesia botrana* |
| Aggl. | *Ostrinia nubilalis* |
| Aggl. | *Pandemis* spp. |
| Aggl. | *Pectinophora gossyp.* |
| Aggl. | *Phyllocnistis citrella* |
| Aggl. | *Pieris* spp. |
| Aggl. | *Plutiia xylostella* |
| Aggl. | *Scirpophaga* spp. |
| Aggl. | *Sesamia* spp. |
| Aggl. | *Sparganothis* spp. |
| Aggl. | *Spodoptera* spp. |
| Aggl. | *Tortrix* spp. |
| Aggl. | *Trichoplusia ni* |
| Aggl. | *Agriotes* spp. |
| Aggl. | *Anthonomus grandis* |
| Aggl. | *Curculio* spp. |
| Aggl. | *Diabrotica balteata* |
| Aggl. | *Leptinotarsa* spp. |
| Aggl. | *Lissorhoptrus* spp. |
| Aggl. | *Otiorhynchus* spp. |
| Aggl. | *Aleurothrixus* spp. |
| Aggl. | *Aleyrodes* spp. |
| Aggl. | *Aonidiella* spp. |
| Aggl. | *Aphididae* spp. |
| Aggl. | *Aphis* spp. |
| Aggl. | *Bemisia tabaci* |
| Aggl. | *Empoasca* spp. |
| Aggl. | *Mycus* spp. |
| Aggl. | *Nephotettix* spp. |
| Aggl. | *Nilaparvata* spp. |
| Aggl. | *Pseudococcus* spp. |
| Aggl. | *Psylla* spp. |
| Aggl. | *Quadraspidiotus* spp. |
| Aggl. | *Schizaphis* spp. |
| Aggl. | *Trialeurodes* spp. |
| Aggl. | *Lyriomyza* spp. |
| Aggl. | *Oscinella* spp. |
| Aggl. | *Phorbia* spp. |
| Aggl. | *Frankliniella* spp. |
| Aggl. | *Thrips* spp. |
| Aggl. | *Scirtothrips aurantii* |
| Aggl. | *Aceria* spp. |
| Aggl. | *Aculus* spp. |
| Aggl. | *Brevipalpus* spp. |
| Aggl. | *Panonychus* spp. |
| Aggl. | *Phyllocoptruta* spp |
| Aggl. | *Tetranychus* spp. |
| Aggl. | *Heterodera* spp. |
| Aggl. | *Meloidogyne* spp. |
| CO | *Adoxophyes* spp. |
| CO | *Agrotis* spp. |
| CO | *Alabama argiliaceae* |
| CO | *Anticarsia gemmatalis* |
| CO | *Chilo* spp. |
| CO | *Ciysia ambiguella* |
| CO | *Crocidolomia binotalis* |
| CO | *Cydia* spp. |
| CO | *Diparopsis castanea* |
| CO | *Earias* spp. |
| CO | *Ephestia* spp. |
| CO | *Heliothis* spp. |
| CO | *Hellula undalis* |
| CO | *Keiferia lycopersicella* |
| CO | *Leucoptera scitella* |
| CO | *Lithocollethis* spp. |
| CO | *Lobesia botrana* |
| CO | *Ostrinia nubilalis* |
| CO | *Pandemis* spp. |
| CO | *Pectinophora gossyp.* |
| CO | *Phyllocnistis citrella* |
| CO | *Pieris* spp. |
| CO | *Plutella xylostella* |
| CO | *Scirpophaga* spp. |
| CO | *Sesamia* spp. |
| CO | *Sparganothis* spp. |
| CO | *Spodoptera* spp. |
| CO | *Tortrix* spp. |
| CO | *Trichoplusia ni* |
| CO | *Agriotes* spp. |
| CO | *Anthonomus grandis* |
| CO | *Curculio* spp. |
| CO | *Diabrotica balteata* |
| CO | *Leptinotarsa* spp. |
| CO | *Lissorhoptrus* spp. |
| CO | *Otiorhynchus* spp. |
| CO | *Aleurothrixus* spp. |
| CO | *Aleyrodes* spp. |
| CO | *Aonidielia* spp. |
| CO | *Aphididae* spp. |
| CO | *Aphis* spp. |
| CO | *Bemisia tabaci* |
| CO | *Empoasca* spp. |
| CO | *Mycus* spp. |
| CO | *Nephotettix* spp. |
| CO | *Nilaparvata* spp. |
| CO | *Pseudococcus* spp. |
| CO | *Psylla* spp. |
| CO | *Quadraspidiotus* spp. |
| CO | *Schizaphis* spp. |
| CO | *Trialeurodes* spp. |
| CO | *Lyriomyza* spp. |
| CO | *Oscinella* spp. |
| CO | *Phorbia* spp. |
| CO | *Frankliniella* spp. |
| CO | *Thrips* spp. |
| CO | *Scirtothrips aurantii* |
| CO | *Aceria* spp. |
| CO | *Acutus* spp. |
| CO | *Brevipalpus* spp. |
| CO | *Panonychus* spp. |
| CO | *Phyllocoptruta* spp. |
| CO | *Tetranychus* spp. |
| CO | *Heterodera* spp. |
| CO | *Meloidogyne* spp. |
| CH | *Adoxophyes* spp. |
| CH | *Agrotis* spp. |
| CH | *Alabama argillaceae* |
| CH | *Anticarsia gemmatalis* |
| CH | *Chilo* spp. |
| CH | *Clysia ambiguella* |
| CH | *Crocidolomia binotalis* |
| CH | *Cydia* spp. |
| CH | *Diparopsis castanea* |
| CH | *Earias* spp. |
| CH | *Ephestia* spp. |
| CH | *Heliothis* spp. |
| CH | *Hellula undalis* |
| CH | *Keiferia lycopersicella* |
| CH | *Leucoptera scitella* |
| CH | *Lithocollethis* spp. |
| CH | *Lobesia botrana* |
| CH | *Ostrinia nubilalis* |
| CH | *Pandemis* spp. |
| CH | *Pectinophora gossyp.* |
| CH | *Phyllocnistis citrella* |
| CH | *Pieris* spp. |
| CH | *Plutella xylostella* |
| CH | *Scirpophaga* spp. |

TABLE 2-continued

| AP | Control of |
|---|---|
| CH | *Sesamia* spp. |
| CH | *Sparganothis* spp. |
| CH | *Spodoptera* spp. |
| CH | *Tortrix* spp. |
| CH | *Trichoplusia ni* |
| CH | *Agriotes* spp. |
| CH | *Anthonomus grandis* |
| CH | *Curculio* spp. |
| CH | *Diabrotica balteata* |
| CH | *Leptinotarsa* spp. |
| CH | *Lissorhoptrus* spp. |
| CH | *Otiorhynohus* spp. |
| CH | *Aleurothrixus* spp. |
| CH | *Aleyrodes* spp. |
| CH | *Aonidiella* spp. |
| CH | *Aphididae* spp. |
| CH | *Aphis* spp. |
| CH | *Bemisia tabaci* |
| CH | *Empoasca* spp. |
| CH | *Mycus* spp. |
| CH | *Nephotettix* spp. |
| CH | *Nilaparvata* spp. |
| CH | *Pseudococcus* spp. |
| CH | *Psylla* spp. |
| CH | *Quadraspidiotus* spp. |
| CH | *Schizaphis* spp. |
| CH | *Trialeurodes* spp. |
| CH | *Lyriomyza* spp. |
| CH | *Oscinella* spp. |
| CH | *Phorbia* spp. |
| CH | *Frankliniella* spp. |
| CH | *Thrips* spp. |
| CH | *Scirtothrips aurantii* |
| CH | *Aceria* spp. |
| CH | *Aculus* spp. |
| CH | *Brevipalpus* spp. |
| CH | *Panonychus* spp. |
| CH | *Phyllocoptruta* spp. |
| CH | *Tetranychus* spp. |
| CH | *Heterodera* spp. |
| CH | *Meloidogyne* spp. |
| SS | *Adoxophyes* spp. |
| SS | *Agrotis* spp. |
| SS | *Alabama argillaceae* |
| SS | *Anticarsia gemmatalis* |
| SS | *Chilo* spp. |
| SS | *Clysia ambiguella* |
| SS | *Crocidolomia binotalis* |
| SS | *Cydia* spp. |
| SS | *Diparopsis castanea* |
| SS | *Earias* spp. |
| SS | *Ephestia* spp. |
| SS | *Heliothis* spp. |
| SS | *Hellula undalis* |
| SS | *Keiferia lycopersicella* |
| SS | *Leucoptera scitella* |
| SS | *Lithocollethis* spp. |
| SS | *Lobesia botrana* |
| SS | *Ostrinia nubilalis* |
| SS | *Pandemis* spp. |
| SS | *Pectinophora gossyp.* |
| SS | *Phyllocnistis citrella* |
| SS | *Pieris* spp. |
| SS | *Plutella xylostella* |
| SS | *Scirpophaga* spp. |
| SS | *Sesamia* spp. |
| SS | *Sparganothis* spp. |
| SS | *Spodoptera* spp. |
| SS | *Tortrix* spp. |
| SS | *Trichopiusia ni* |
| SS | *Agriotes* spp. |
| SS | *Anthonomus grandis* |
| SS | *Curculio* spp. |
| SS | *Diabrotica balteata* |
| SS | *Leptinotarsa* spp. |
| SS | *Lissorhoptrus* spp. |
| SS | *Otiorhynchus* spp. |
| SS | *Aleurothrixus* spp. |
| SS | *Aleyrodes* spp. |
| SS | *Aonidielia* spp. |
| SS | *Aphididae* spp. |
| SS | *Aphis* spp. |
| SS | *Bemisia tabaci* |
| SS | *Empoasca* spp. |
| SS | *Mycus* spp. |
| SS | *Nephotettix* spp. |
| SS | *Nilaparvata* spp. |
| SS | *Pseudococcus* spp. |
| SS | *Psylla* spp. |
| SS | *Quadraspidiotus* spp. |
| SS | *Schizaphis* spp. |
| SS | *Trialeurodes* spp. |
| SS | *Lyriomyza* spp. |
| SS | *Oscinella* spp. |
| SS | *Phorbia* spp. |
| SS | *Frankliniella* spp. |
| SS | *Thrips* spp. |
| SS | *Scirtothrips aurantii* |
| SS | *Aceria* spp. |
| SS | *Aculus* spp. |
| SS | *Brevipalpus* spp. |
| SS | *Panonychus* spp. |
| SS | *Phyllocoptruta* spp. |
| SS | *Tetranychus* spp. |
| SS | *Heterodera* spp. |
| SS | *Meloidogyne* spp. |
| HO | *Adoxophyes* spp. |
| HO | *Agrotis* spp. |
| HO | *Alabama argillaceae* |
| HO | *Anticarsia gemmatalis* |
| HO | *Chilo* spp. |
| HO | *Clysia ambiguella* |
| HO | *Crocidolomia binotalis* |
| HO | *Cydia* spp. |
| HO | *Diparopsis castanea* |
| HO | *Earias* spp. |
| HO | *Ephestia* spp. |
| HO | *Heliothis* spp. |
| HO | *Hellula undalis* |
| HO | *Keiferia lycopersicella* |
| HO | *Leucoptera scitella* |
| HO | *Lithocollethis* spp. |
| HO | *Lobesia botrana* |
| HO | *Ostrinia nubilalis* |
| HO | *Pandemis* spp. |
| HO | *Pectinophora gossypiella* |
| HO | *Phyllocnistis citrella* |
| HO | *Pieris* spp. |
| HO | *Plutella xylostella* |
| HO | *Scirpophaga* spp. |
| HO | *Sesamia* spp. |
| HO | *Sparganothis* spp. |
| HO | *Spodoptera* spp. |
| HO | *Tortrix* spp. |
| HO | *Trichoplusia ni* |
| HO | *Agriotes* spp. |
| HO | *Anthonomus grandis* |
| HO | *Curculio* spp. |
| HO | *Diabrotica balteata* |
| HO | *Leptinotarsa* spp. |
| HO | *Lissorhoptrus* spp. |
| HO | *Otiorhynchus* spp. |
| HO | *Aleurothrixus* spp. |
| HO | *Aleyrodes* spp. |
| HO | *Aonidiella* spp. |
| HO | *Aphididae* spp. |
| HO | *Aphis* spp. |
| HO | *Bemisia tabaci* |
| HO | *Empoasca* spp. |
| HO | *Mycus* spp. |
| HO | *Nephotettix* spp. |
| HO | *Nilaparvata* spp. |
| HO | *Pseudococcus* spp. |
| HO | *Psylla* spp. |
| HO | *Quadraspidiotus* spp. |

TABLE 2-continued

| AP | Control of |
|---|---|
| HO | *Schizaphis* spp. |
| HO | *Trialeurodes* spp. |
| HO | *Lyriomyza* spp. |
| HO | *Oscinella* spp. |
| HO | *Phorbia* spp. |
| HO | *Frankliniella* spp. |
| HO | *Thrips* spp. |
| HO | *Scirtothrips aurantii* |
| HO | *Aceria* spp. |
| HO | *Acutus* spp. |
| HO | *Brevipalpus* spp. |
| HO | *Panonychus* spp. |
| HO | *Phyllocoptruta* spp. |
| HO | *Tetranychus* spp. |
| HO | *Heterodera* spp. |
| HO | *Meloidogyne* spp. |

In the table, the following abbreviations were used:
active principle of the transgenic plant: AP
*Photorhabdus luminescens*: PL
*Xenorhabdus nematophilus*: XN
proteinase inhibitors: Plnh.
plant lectins PLec.
agglutinines: Aggl.
3-hydroxysteroid oxidase: HO
cholesterol oxidase: CO
chitinase: CH
glucanase: GL
stilbene synthase: SS

TABLE 3

| Principle | Tolerance to | Plant |
|---|---|---|
| ALS | sulphonylurea compounds etc.*** | cotton |
| ALS | sulphonylurea compounds etc.*** | rice |
| ALS | sulphonylurea compounds etc.*** | *Brassica* |
| ALS | sulphonylurea compounds etc.*** | potatoes |
| ALS | sulphonylurea compounds etc.*** | tomatoes |
| ALS | sulphonylurea compounds etc.*** | pumpkin |
| ALS | sulphonylurea compounds etc.*** | soya beans |
| ALS | sulphonylurea compounds etc.*** | maize |
| ALS | sulphonylurea compounds etc.*** | wheat |
| ALS | sulphonylurea compounds etc.*** | pome fruit |
| ALS | sulphonylurea compounds etc.*** | stone fruit |
| ALS | sulphonylurea compounds etc.*** | citrus fruit |
| ACCase | +++ | cotton |
| ACCase | +++ | rice |
| ACCase | +++ | *Brassica* |
| ACCase | +++ | potato |
| ACCase | +++ | tomatoes |
| ACCase | +++ | pumpkin |
| ACCase | +++ | soya beans |
| ACCase | +++ | maize |
| ACCase | +++ | wheat |
| ACCase | +++ | pome fruit |
| ACCase | +++ | stone fruit |
| ACCase | +++ | citrus fruit |
| HPPD | isoxaflutole, isoxachlortole, sulcotrione, mesotrione | cotton |
| HPPD | isoxaflutole, isoxachlortole, sulcotrione, mesotrione | rice |
| HPPD | isoxaflutole, isoxachlortole, sulcotrione, mesotrione | *Brassica* |
| HPPD | isoxaflutole, isoxachlortole, sulcotrione, mesotrione | potatoes |
| HPPD | isoxaflutole, isoxachlortole, sulcotrione, mesotrione | tomatoes |
| HPPD | isoxaflutole, isoxachlortole, sulcotrione, mesotrione | pumpkin |
| HPPD | isoxaflutole, isoxachlortole, sulcotrione, mesotrione | soya beans |
| HPPD | isoxaflutole, isoxachlortole, sulcotrione, mesotrione | maize |
| HPPD | isoxaflutole, isoxachlortole, sulcotrione, mesotrione | wheat |

TABLE 3-continued

| Principle | Tolerance to | Plant |
|---|---|---|
| HPPD | isoxaflutole, isoxachlortole, sulcotrione, mesotrione | pome fruit |
| HPPD | isoxaflutole, isoxachlortole, sulcotrione, mesotrione | stone fruit |
| HPPD | isoxaflutole, isoxachlortole, sulcotrione, mesotrione | citrus fruit |
| nitrilase | bromoxynil, loxynil | cotton |
| nitrilase | bromoxynil, loxynil | rice |
| nitrilase | bromoxynil, loxynil | *Brassica* |
| nitrilase | bromoxynil, loxynil | potatoes |
| nitrilase | bromoxynil, loxynil | tomatoes |
| nitrilase | bromoxynil, loxynil | pumpkin |
| nitrilase | bromoxynil, loxynil | soya beans |
| nitrilase | bromoxynil, loxynil | maize |
| nitrilase | bromoxynil, loxynil | wheat |
| nitrilase | bromoxynil, loxynil | pome fruit |
| nitrilase | bromoxynil, loxynil | stone fruit |
| nitrilase | bromoxynil, loxynil | citrus fruit |
| IPS | chloroactanilides&&& | cotton |
| IPS | chloroactanilides&&& | rice |
| IPS | chloroactanilides&&& | *Brassica* |
| IPS | chloroactanilides&&& | potatoes |
| IPS | chloroactanilides&&& | tomatoes |
| IPS | chloroactanilides&&& | pumpkin |
| IPS | chloroactanilides&&& | soya beans |
| IPS | chloroactanilides&&& | maize |
| IPS | chloroactanilides&&& | wheat |
| IPS | chloroactanilides&&& | pome fruit |
| IPS | chloroactanilides&&& | stone fruit |
| IPS | chloroactanilides&&& | citrus fruit |
| HOM | 2,4-D, mecoprop-P | cotton |
| HOM | 2,4-D, mecoprop-P | rice |
| HOM | 2,4-D, mecoprop-P | *Brassica* |
| HOM | 2,4-D, mecoprop-P | potatoes |
| HOM | 2,4-D, mecoprop-P | tomatoes |
| HOM | 2,4-D, mecoprop-P | pumpkin |
| HOM | 2,4-D, mecoprop-P | soya beans |
| HOM | 2,4-D, mecoprop-P | maize |
| HOM | 2,4-D, mecoprop-P | wheat |
| HOM | 2,4-D, mecoprop-P | pome fruit |
| HOM | 2,4-D, mecoprop-P | stone fruit |
| HOM | 2,4-D, mecoprop-P | citrus fruit |
| PROTOX | Protox inhibitors/// | cotton |
| PROTOX | Protox inhibitors/// | rice |
| PROTOX | Protox inhibitors/// | *Brassica* |
| PROTOX | Protox inhibitors/// | potatoes |
| PROTOX | Protox inhibitors/// | tomatoes |
| PROTOX | Protox inhibitors/// | pumpkin |
| PROTOX | Protox inhibitors/// | soya beans |
| PROTOX | Protox inhibitors/// | maize |
| PROTOX | Protox inhibitors/// | wheat |
| PROTOX | Protox inhibitors/// | pome fruit |
| PROTOX | Protox inhibitors/// | stone fruit |
| PROTOX | Protox inhibitors/// | citrus fruit |
| EPSPS | glyphosate and/or sulphosate | cotton |
| EPSPS | glyphosate and/or sulphosate | rice |
| EPSPS | glyphosate and/or sulphosate | *Brassica* |
| EPSPS | glyphosate and/or sulphosate | potatoes |
| EPSPS | glyphosate and/or sulphosate | tomatoes |
| EPSPS | glyphosate and/or sulphosate | pumpkin |
| EPSPS | glyphosate and/or sulphosate | soya beans |
| EPSPS | glyphosate and/or sulphosate | maize |
| EPSPS | glyphosate and/or sulphosate | wheat |
| EPSPS | glyphosate and/or sulphosate | pome fruit |
| EPSPS | glyphosate and/or sulphosate | stone fruit |
| EPSPS | glyphosate and/or sulphosate | citrus fruit |
| GS | gluphosinate and/or bialaphos | cotton |
| GS | gluphosinate and/or bialaphos | rice |
| GS | gluphosinate and/or bialaphos | *Brassica* |
| GS | gluphosinate and/or bialaphos | potatoes |
| GS | gluphosinate and/or bialaphos | tomatoes |
| GS | gluphosinate and/or bialaphos | pumpkin |
| GS | gluphosinate and/or bialaphos | soya beans |
| GS | gluphosinate and/or bialaphos | maize |
| GS | gluphosinate and/or bialaphos | wheat |
| GS | gluphosinate and/or bialaphos | pome fruit |

TABLE 3-continued

| Principle | Tolerance to | Plant |
|---|---|---|
| GS | gluphosinate and/or bialaphos | stone fruit |
| GS | gluphosinate and/or bialaphos | citrus fruit |

Abbreviations:
acetyl-CoA carboxylase: ACCase
acetolactate synthase: ALS
hydroxyphenylpyruvate dioxygenase: HPPD
inhibition of protein synthesis: IPS
hormone imitation: HO
glutamine synthetase: GS
protoporphyrinogen oxidase: PROTOX
5-enolpyruvyl-3-phosphoshikimate synthase: EPSPS
***included are sulphonylurea compounds, imidazolinones, triazolopyrimidines, dimethoxypyrimidines and N-acylsulphonamides: sulphonylurea compounds such as chlorsulfuron, chlorimuron, ethamethsulfuron, metsulfuron, primisulfuron, prosulfuron, triasulfuron, cinosulfuron, trifusulfuron, oxasulfuron, bensulfuron, tribenuron, ACC 322140, fluzasulfuron, ethoxysulfuron, fluzasulfuron, nicosulfuron, rimsulfuron, thifensulfuron, pyrazosulfuron, clopyrasulfuron, NC 330, azimsulfuron, imazosulfuron, sulfosulfuron, amidosulfuron, flupyrsulfuron, CGA 362622
imidazolinones such as imazamethabenz, imazaquin, imazamethypyr, imazethapyr, imazapyr and imazamox;
triazolopyrimidines such as DE 511, flumetsulam and chloransulam;
dimethoxypyrimidines such as, for example, pyrithiobac, pyriminobac, bispyribac and pyribenzoxim.
+++Tolerance to diclofop-methyl, fluazifop-P-butyl, haloxyfop-P-methyl, haloxyfop-P-ethyl, quizalafop-P-ethyl, clodinafop-propargyl, fenoxaprop-ethyl, tepraloxydim, alloxydim, sethoxydim, cycloxydim, cloproxydim, tralkoxydim, butoxydim, caloxydim, clefoxydim, clethodim.
&&&chloroacetanilides such as, for example, alachlor, acetochlor, dimethenamid
///Protox inhibitors: for example diphenyl ethers such as, for example, acifluorfen, aclonifen, bifenox, chlornitrofen, ethoxyfen, fluoroglucofen, fomesafen, lactofen, oxyfluorfen; imides such as, for example, azafenidin, carfentrazone-ethyl, cinidon-ethyl, flumiclorac-pentyl, flumioxazin, fluthiacet-methyl, oxadiargyl, oxadiazon, pentoxazone, sulfentrazone, imides and other compounds such as, for example, flumipropyn, flupropacil, nipyraclofen and thidiazimin; and also fluazola and pyraflufen-ethyl.

TABLE 4

List of examples of genetically modified plants having modified properties

| Genetically modified plants | Genetically modified properties |
|---|---|
| Dianthus caryophyllus (carnation) line 66 [Florigene Pty. Ltd.] | Longer-lasting as a result of reduced ethylene accumulation owing to the expression of ACC synthase; tolerant to sulphonylurea herbicides |
| Dianthus caryophyllus (carnation) lines 4, 11, 15, 16 [Florigene Pty. Ltd.] | Modified flower colour; tolerant to sulphonyl-urea herbicides |
| Dianthus caryophyllus (carnation) lines 959A, 988A, 1226A, 1351A, 1363A, 1400A [Florigene Pty. Ltd.] | Modified flower colour; tolerant to sulphonyl-urea herbicides |
| Brassica napus (Argentine oilseed rape) lines 23-18-17, 23-198 [Monsanto Company] | Modified fatty acid content in the seeds |
| Zea mays L. (maize) lines REN-ØØØ38-3 (LY038) [Monsanto Company] | Elevated lysine content |
| Zea mays L. (maize) lines REN-ØØØ38-3, MON-ØØ81Ø-6 (MON-ØØ81Ø-6 × LY038) [Monsanto Company] | Elevated lysine content, corn borer resistant |
| Cucumis melo (melon) lines A, B | Delayed maturity as a result of the expression of S-adenosylmethionine |

TABLE 4-continued

List of examples of genetically modified plants having modified properties

| Genetically modified plants | Genetically modified properties |
|---|---|
| [Agritope Inc.] | hydrolase |
| Carica papaya (papaya) lines 55-1/63-1 [Cornell University] | Resistant to the papaya ring spot virus (PRSV) |
| Solanum tuberosum L. (potato) lines RBMT21-129, RBMT21-350, RBMT22-082 [Monsanto Company] | Resistant to the Colorado beetle and the potato leaf roll virus (PLRV) |
| Solanum tuberosum L. (potato) lines RBMT15-101, SEMT15-02, SEMT15-15 [Monsanto Company] | Resistant to the Colorado beetle and the potato virus Y (PVY) |
| Glycine max L. (soya bean) lines DD-Ø26ØØ5-3 (G94-1, G94-19, G168 [DuPont Canada Agricultural Products] | Modified fatty acid content in the seeds, in particular elevated oleic acid content |
| Glycine max L. (soya bean) lines OT96-15 [Agriculture & Agri-Food Canada] | Modified fatty acid content in the seeds, in particular reduced linolenic acid content |
| Cucurbita pepo (pumpkin) line ZW20 [Upjohn (USA); Seminis Vegetable Inc. (Canada)] | Resistant to viral infections, watermelon mosaic virus (WMV) 2 and zucchini yellow mosaic virus (ZYMV) |
| Cucurbita pepo (pumpkin) line CZW-3 [Asgrow (USA); Seminis Vegetable Inc. (Canada)] | Resistance to viral infections, cucumber mosaic virus (CMV), watermelon mosaic virus (WMV) 2 and zucchini yellow mosaic virus (ZYMV) |
| Nicotiana tabacum L. (tobacco) line Vector 21-41 [Vector Tobacco] | Reduced nicotine content |
| Lycopersicon esculentum (tomato) line 1345-4 [DNA Plant Technology] | Longer lasting as a result of reduced ethylene accumulation owing to the expression of ACC synthase |
| Lycopersicon esculentum (tomato) line 35 1 N [Agritope Inc.] | Delayed maturity as a result of the expression of S-adenosylmethionine hydrolase |
| Lycopersicon esculentum (tomato) line CGN-89322-3 (8338) [Monsanto Company] | Delayed maturity as a result of the expression of ACCd |
| Lycopersicon esculentum (tomato) lines B, Da, F [Zeneca Seeds] | Delayed softening as a result of a reduced expression of polygalacturonase |
| Lycopersicon esculentum (tomato) line CGN-89564-2 (FLAVR SAVR) [Calgene Inc.] | Delayed softening as a result of a reduced expression of polygalacturonase |
| cotton Line DP444 BG/RR [Delta and Pine Land Co.] | Early maturation, stacked gene variety with Lepidoptera resistance as a result of cloning the genes for Cry1Ac toxin formation (Bollgard) and glyphosate resistance (Roundup Ready) |
| maize VSN-BT (MON 810) | Resistance to the European corn borer |
| maize HCL201CRW2RR2 × LH324 | Resistance to beetles such as the Western corn rootworm and glyphosate resistance (Roundup Ready) |

TABLE 5

| No. | Line/trait | Trade name | Plant | Company | Genetically modified properties |
|---|---|---|---|---|---|
| B-1 | ASR368 | | Agrostis stolonifera Creeping Bentgrass | Scotts Seeds | Glyphosate tolerance derived by inserting a modified 5-enolpyruvylshikimate-3-phosphate synthase (EPSPS) encoding gene from Agrobacterium tumefaciens. |
| B-2 | H7-1 | Roundup Ready Sugar Beet | Beta vulgaris (Sugar Beet) | Monsanto Company | Glyphosate herbicide tolerant sugar beet produced by inserting a gene encoding the enzyme 5-enolypyruvylshikimate-3-phosphate synthase (EPSPS) from the CP4 strain of Agrobacterium tumefaciens. |

TABLE 5-continued

| No. | Line/trait | Trade name | Plant | Company | Genetically modified properties |
|---|---|---|---|---|---|
| B-3 | T120-7 | | *Beta vulgaris* (Sugar Beet) | Bayer CropScience (Aventis CropScience (AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. |
| B-4 | GTSB77 | | *Beta vulgaris* (Sugar Beet) | Novartis Seeds; Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*. |
| B-5 | 23-18-17, 23-198 | | *Brassica napus* (Argentine Canola) | Monsanto Company (formerly Calgene) | High laurate (12:0) and myristate (14:0) canola produced by inserting a thioesterase encoding gene from the California bay laurel (*Umbellularia californica*). |
| B-6 | 45A37, 46A40 | | *Brassica napus* (Argentine Canola) | Pioneer Hi-Bred International Inc. | High oleic acid and low linolenic acid canola produced through a combination of chemical mutagenesis to select for a fatty acid desaturase mutant with elevated oleic acid, and traditional back-crossing to introduce the low linolenic acid trait. |
| B-7 | 46A12, 46A16 | | *Brassica napus* (Argentine Canola) | Pioneer Hi-Bred International Inc. | Combination of chemical mutagenesis, to achieve the high oleic acid trait, and traditional breeding with registered canola varieties. |
| B-8 | GT200 | | *Brassica napus* (Argentine Canola) | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. |
| B-9 | GT73, RT73 | Roundup Ready ™ canola | *Brassica napus* (Argentine Canola) | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. |
| B-10 | HCN10 | | *Brassica napus* (Argentine Canola) | Aventis CropScience | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. |
| B-11 | Topas 19/2 (HCN92) | InVigor ® Canola | *Brassica napus* (Argentine Canola) | Bayer CropScience (Aventis CropScience (AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. |
| B-12 | MS1, RF1 =>PGS1 | | *Brassica napus* (Argentine Canola) | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. |
| B-13 | MS1, RF2 =>PGS2 | | *Brassica napus* (Argentine Canola) | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. |

TABLE 5-continued

| No. | Line/trait | Trade name | Plant | Company | Genetically modified properties |
|---|---|---|---|---|---|
| B-14 | MS8 × RF3 | InVigor ® Canola | *Brassica napus* (Argentine Canola) | Bayer CropScience (Aventis CropScience (AgrEvo)) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. |
| B-15 | NS738, NS1471, NS1473 | | *Brassica napus* (Argentine Canola) | Pioneer Hi-Bred International Inc. | Selection of somaclonal variants with altered acetolactate synthase (ALS) enzymes, following chemical mutagenesis. Two lines (P1, P2) were initially selected with modifications at different unlinked loci. NS738 contains the P2 mutation only. |
| B-16 | OXY-235 | | *Brassica napus* (Argentine Canola) | Aventis CropScience (formerly Rhone Poulenc Inc.) | Tolerance to the herbicides bromoxynil and ioxynil by incorporation of the nitrilase gene (oxy) from *Klebsiella pneumoniae*. |
| B-17 | MS8 | InVigor ® Canola | *Brassica napus* (Argentine Canola) | Bayer CropScience | Traits: Glufosinate tolerance, Male sterility Genes: bar, barnase |
| B-18 | PHY14, PHY35 | | *Brassica napus* (Argentine Canola) | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. |
| B-19 | PHY36 | | *Brassica napus* (Argentine Canola) | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. |
| B-20 | RF1, (B93-101) | InVigor ® Canola | *Brassica napus* (Argentine Canola) | Bayer CropScience | Genes: bar, barstar, neomycin phosphotransferase II (npt II); Traits: Fertility restoration, Glufosinate tolerance, Kanamycin resistance |
| B-21 | RF2, (B94-101) | | *Brassica napus* (Argentine Canola) | Bayer CropScience | Genes: bar, barstar, neomycin phosphotransferase II (npt II); Traits: Fertility restoration, Glufosinate tolerance, Kanamycin resistance |
| B-22 | RF3, ACS-BNØØ3-6 | InVigor ® Canola | *Brassica napus* (Argentine Canola) | Bayer CropScience | Traits: Fertility restoration, Glufosinate tolerance; Genes bar, barstar |
| B-23 | MS1 (B91-4) | InVigor ® Canola | *Brassica napus* (Argentine Canola) | Bayer CropScience | Traits: Glufosinate tolerance, Kanamycin resistance, Male sterility; Genes: bar, barnase, neomycin phosphotransferase II (npt II) |
| B-24 | T45 (HCN28) | InVigor ® Canola | *Brassica napus* (Argentine Canola) | Bayer CropScience (Aventis CropScience (AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. |
| B-25 | HCR-1 | | *Brassica rapa* (Polish Canola) | Bayer CropScience (Aventis CropScience (AgrEvo)) | Introduction of the glufosinate ammonium herbicide tolerance trait from transgenic *B. napus* line T45. This trait is mediated by the phosphinothricin acetyltransferase (PAT) encoding gene from *S. viridochromogenes*. |
| B-26 | ZSR500/502 | | *Brassica rapa* (Polish Canola) | Monsanto Company | Introduction of a modified 5-enol-pyruvylshikimate-3-phosphate synthase (EPSPS) and a gene from *Achromobacter* sp that degrades glyphosate by conversion to aminomethylphosphonic acid (AMPA) and glyoxylate by interspecific crossing with GT73. |
| B-27 | 55-1/63-1 | | *Carica papaya* (Papaya) | Cornell University | Papaya ringspot virus (PRSV) resistant *papaya* produced by inserting the coat protein (CP) encoding sequences from this plant potyvirus. |

TABLE 5-continued

| No. | Line/trait | Trade name | Plant | Company | Genetically modified properties |
|---|---|---|---|---|---|
| B-28 | RM3-3, RM3-4, RM3-6 | | *Cichorium intybus* (Chicory) | Bejo Zaden BV | Male sterility was via insertion of the barnase ribonuclease gene from *Bacillus amyloliquefaciens*; PPT resistance was via the bar gene from *S. hygroscopicus*, which encodes the PAT enzyme. |
| B-29 | A, B | | *Cucumis melo* (Melon) | Agritope Inc. | Reduced accumulation of S-adenosylmethionine (SAM), and consequently reduced ethylene synthesis, by introduction of the gene encoding S-adenosylmethionine hydrolase. |
| B-30 | CZW-3 | | *Cucurbita pepo* (Squash) | Asgrow (USA); Seminis Vegetable Inc. (Canada) | Cucumber mosiac virus (CMV), zucchini yellows mosaic (ZYMV) and watermelon mosaic virus (WMV) 2 resistant squash (*Curcurbita pepo*) produced by inserting the coat protein (CP) encoding sequences from each of these plant viruses into the host genome. |
| B-31 | ZW20 | | *Cucurbita pepo* (*Squash*) | Upjohn (USA); Seminis Vegetable Inc. (Canada) | Zucchini yellows mosaic (ZYMV) and watermelon mosaic virus (WMV) 2 resistant squash (*Curcurbita pepo*) produced by inserting the coat protein (CP) encoding sequences from each of these plant potyviruses into the host genome. |
| B-32 | 66 | | *Dianthus caryophyllus* (Carnation) | Florigene Pty Ltd. | Delayed senescence and sulfonylurea herbicide tolerant carnations produced by inserting a truncated copy of the carnation aminocyclopropane cyclase (ACC) synthase encoding gene in order to suppress expression of the endogenous unmodified gene, which is required for normal ethylene biosynthesis. Tolerance to sulfonyl urea herbicides was via the introduction of a chlorsulfuron tolerant version of the acetolactate synthase (ALS) encoding gene from tobacco. |
| B-33 | 4, 11, 15, 16 | | *Dianthus caryophyllus* (Carnation) | Florigene Pty Ltd. | Modified colour and sulfonylurea herbicide tolerant carnations produced by inserting two anthocyanin biosynthetic genes whose expression results in a violet/mauve colouration. Tolerance to sulfonyl urea herbicides was via the introduction of a chlorsulfuron tolerant version of the acetolactate synthase (ALS) encoding gene from tobacco. |
| B-34 | 11363 | Moonshadow | *Dianthus caryophyllus* (Carnation) | Florigene Pty Ltd. | Traits: Coloration; Genes als, dihydroflavonol reductase (dfr), flavonoid 3',5'hydroxylase (F3'5'H) |
| B-35 | 959A, 988A, 1226A, 1351A, 1363A, 1400A | | *Dianthus caryophyllus* (Carnation) | Florigene Pty Ltd. | Introduction of two anthocyanin biosynthetic genes to result in a violet/mauve colouration; Introduction of a variant form of acetolactate synthase (ALS). |
| B-36 | 123.2. (40619) | Moonshade | *Dianthus caryophyllus* (Carnation) | Florigene Pty Ltd. | Traits: Coloration; Genes als, dihydroflavonol reductase (dfr), flavonoid 3',5'hydroxylase (F3'5'H) |
| B-37 | 123.8.8 (40685) | Moonvista | *Dianthus caryophyllus* (Carnation) | Florigene Pty Ltd. | |
| B-38 | 11 (7442) | Moondust | *Dianthus caryophyllus* (Carnation) | Florigene Pty Ltd. | |
| B-39 | A2704-12, A2704-21, A5547-35 | | *Glycine max* L. (Soybean) | Aventis CropScience | Glufosinate ammonium herbicide tolerant soybean produced by inserting a modified phosphinothricin acetyltransferase (PAT) encoding gene from the soil bacterium *Streptomyces viridochromogenes*. |
| B-40 | A5547-127 | LibertyLink ® Soybean | *Glycine max* L. (Soybean) | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| B-41 | G94-1, G94-19, G168 | | *Glycine max* L. (Soybean) | DuPont Canada Agricultural Products | High oleic acid soybean produced by inserting a second copy of the fatty acid desaturase (GmFad2-1) encoding gene from soybean, which resulted in "silencing" of the endogenous host gene. |

TABLE 5-continued

| No. | Line/trait | Trade name | Plant | Company | Genetically modified properties |
|---|---|---|---|---|---|
| B-42 | GTS 40-3-2 | Roundup Ready ™ soybeans | Glycine max L. (Soybean) | Monsanto Company | Glyphosate tolerant soybean variety produced by inserting a modified 5-enolpyruvylshikimate-3-phosphate synthase (EPSPS) encoding gene from the soil bacterium Agrobacterium tumefaciens. |
| B-43 | GU262 | | Glycine max L. (Soybean) | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium Streptomyces viridochromogenes. |
| B-44 | MON89788 | Roundup RReady2Yield ™ soybean | Glycine max L. (Soybean) | Monsanto Company | Glyphosate-tolerant soybean produced by inserting a modified 5-enolpyruvylshikimate-3-phosphate synthase (EPSPS) encoding aroA (epsps) gene from Agrobacterium tumefaciens CP4. |
| B-45 | OT96-15 | | Glycine max L. (Soybean) | Agriculture & Agri-Food Canada | Low linolenic acid soybean produced through traditional cross-breeding to incorporate the novel trait from a naturally occurring fan1 gene mutant that was selected for low linolenic acid. |
| B-46 | W62, W98 | | Glycine max L. (Soybean) | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium Streptomyces hygroscopicus. |
| B-47 | 15985 | Bollgard II cotton | Gossypium hirsutum L. (Cotton) | Monsanto Company | Insect resistant cotton derived by transformation of the DP50B parent variety, which contained event 531 (expressing Cry1Ac protein), with purified plasmid DNA containing the cry2Ab gene from B. thuringiensis subsp. kurstaki. |
| B-48 | 19-51A | | Gossypium hirsutum L. (Cotton) | DuPont Canada Agricultural Products | Introduction of a variant form of acetolactate synthase (ALS). |
| B-49 | 281-24-236 | | Gossypium hirsutum L. (Cotton) | DOW AgroSciences LLC | Insect-resistant cotton produced by inserting the cry1F gene from Bacillus thuringiensis var. aizawai. The PAT encoding gene from Streptomyces viridochromogenes was introduced as a selectable marker. |
| B-50 | 3006-210-23 | WideStrike ™ | Gossypium hirsutum L. (Cotton) | DOW AgroSciences LLC | Insect-resistant cotton produced by inserting the cry1Ac gene from Bacillus thuringiensis subsp. kurstaki. The PAT encoding gene from Streptomyces viridochromogenes was introduced as a selectable marker. |
| B-51 | 31807/31808 | | Gossypium hirsutum L. (Cotton) | Calgene Inc. | Insect-resistant and bromoxynil herbicide tolerant cotton produced by inserting the cry1Ac gene from Bacillus thuringiensis and a nitrilase encoding gene from Klebsiella pneumoniae. |
| B-52 | BXN | | Gossypium hirsutum L. (Cotton) | Calgene Inc. | Bromoxynil herbicide tolerant cotton produced by inserting a nitrilase encoding gene from Klebsiella pneumoniae. |
| B-53 | COT102 | | Gossypium hirsutum L. (Cotton) | Syngenta Seeds, Inc. | Insect-resistant cotton produced by inserting the vip3A(a) gene from Bacillus thuringiensis AB88. The APH4 encoding gene from E. coli was introduced as a selectable marker. |
| B-54 | DAS-21Ø23-5 × DAS-24236-5 | | Gossypium hirsutum L. (Cotton) | DOW AgroSciences LLC | WideStrike ™, a stacked insect-resistant cotton derived from conventional cross-breeding of parental lines 3006-210-23 (OECD identifier: DAS-21Ø23-5) and 281-24-236 (OECD identifier: DAS-24236-5). |
| B-55 | DAS-21Ø23-5 × DAS-24236-5 × MON88913 | | Gossypium hirsutum L. (Cotton) | DOW AgroSciences LLC and Pioneer Hi-Bred International Inc. | Stacked insect-resistant and glyphosate-tolerant cotton derived from conventional cross-breeding of WideStrike cotton (OECD identifier: DAS-21Ø23-5 × DAS-24236-5) with MON88913, known as RoundupReady Flex (OECD identifier: MON-88913-8). |

TABLE 5-continued

| No. | Line/trait | Trade name | Plant | Company | Genetically modified properties |
|---|---|---|---|---|---|
| B-56 | DAS-21Ø23-5 × DAS-24236-5 × MON-Ø1445-2 | | *Gossypium hirsutum* L. (Cotton) | DOW AgroSciences LLC | WideStrike ™/Roundup Ready ® cotton, a stacked insect-resistant and glyphosate-tolerant cotton derived from conventional cross-breeding of WideStrike cotton (OECD identifier: DAS-21Ø23-5 × DAS-24236-5) with MON1445 (OECD identifier: MON-Ø1445-2). |
| B-57 | LLCotton25 | | *Gossypium hirsutum* L. (Cotton) | Bayer CropScience (Aventis CropScience (AgrEvo)) | Glufosinate ammonium herbicide tolerant cotton produced by inserting a modified phosphinothricin acetyltransferase (PAT) encoding gene from the soil bacterium *Streptomyces hygroscopicus*. |
| B-58 | LLCotton25 × MON15985 | | *Gossypium hirsutum* L. (Cotton) | Bayer CropScience (Aventis CropScience (AgrEvo)) | Stacked herbicide tolerant and insect resistant cotton combining tolerance to glufosinate ammonium herbicide from LLCotton25 (OECD identifier: ACS-GHØØ1-3) with resistance to insects from MON15985 (OECD identifier: MON-15985-7) |
| B-59 | MON1445/1698 | Roundup Ready ™ cotton | *Gossypium hirsutum* L. (Cotton) | Monsanto Company | Glyphosate herbicide tolerant cotton produced by inserting a naturally glyphosate tolerant form of the enzyme 5-enolpyruvyl shikimate-3-phosphate synthase (EPSPS) from *A. tumefaciens* strain CP4. |
| B-60 | MON15985 × MON88913 | | *Gossypium hirsutum* L. (Cotton) | Monsanto Company | Stacked insect resistant and glyphosate tolerant cotton produced by conventional cross-breeding of the parental lines MON88913 (OECD identifier: MON-88913-8) and 15985 (OECD identifier: MON-15985-7). Glyphosate tolerance is derived from MON88913 which contains two genes encoding the enzyme 5-enolypyruvylshikimate-3-phosphate synthase (EPSPS) from the CP4 strain of *Agrobacterium tumefaciens*. Insect resistance is derived MON15985 which was produced by transformation of the DP50B parent variety, which contained event 531 (expressing Cry1Ac protein), with purified plasmid DNA containing the cry2Ab gene from *B. thuringiensis* subsp. *kurstaki*. |
| B-61 | MON-15985-7 × MON-Ø1445-2 | | *Gossypium hirsutum* L. (Cotton) | Monsanto Company | Stacked insect resistant and herbicide tolerant cotton derived from conventional cross-breeding of the parental lines 15985 (OECD identifier: MON-15985-7) and MON1445 (OECD identifier: MON-Ø1445-2). |
| B-62 | MON531/757/1076 | Bollgard ™ (Ingard ®) | *Gossypium hirsutum* L. (Cotton) | Monsanto Company | Insect-resistant cotton produced by inserting the cry1Ac gene from *Bacillus thuringiensis* subsp. *kurstaki* HD-73 (B.t.k.). |
| B-63 | MON88913 | Roundup Ready Flex Cotton | *Gossypium hirsutum* L. (Cotton) | Monsanto Company | Glyphosate herbicide tolerant cotton produced by inserting two genes encoding the enzyme 5-enolypyruvylshikimate-3-phosphate synthase (EPSPS) from the CP4 strain of *Agrobacterium tumefaciens*. |
| B-64 | MON-ØØ531-6 × MON-Ø1445-2 | | *Gossypium hirsutum* L. (Cotton) | Monsanto Company | Stacked insect resistant and herbicide tolerant cotton derived from conventional cross-breeding of the parental lines MON531 (OECD identifier: MON-ØØ531-6) and MON1445 (OECD identifier: MON-Ø1445-2). |
| B-65 | T304-40 | | *Gossypium hirsutum* L. (Cotton) | Bayer BioScience N.V., Technologiepark 38 B-9052 Gent Belgium | Genetic elements which confer the phenotype insect resistant and glufosinate ammonium herbicide tolerance: cry1: Coding sequence of cry gene from *Bacillus thuringiensis* that confers the insect resistance trait. |

TABLE 5-continued

| No. | Line/trait | Trade name | Plant | Company | Genetically modified properties |
|---|---|---|---|---|---|
| B-66 | GHB714 | | Gossypium hirsutum L. (Cotton) | Bayer BioScience N.V., Technologiepark 38 B-9052 Gent Belgium | bar: Coding sequence of the phosphinothricin acetyltransferase gene (bar) from Streptomyces hygroscopicus that confers the herbicide resistance trait. Genetic elements which confer the phenotype insect resistant and glufosinate ammonium herbicide tolerance: cry2: Coding sequence of cry gene from *Bacillus thuringiensis* that confers the insect resistance trait. bar: Coding sequence of the phosphinothricin acetyltransferase gene (bar) from *Streptomyces hygroscopicus* that confers the herbicide resistance trait. |
| B-67 | GHB119 | | Gossypium hirsutum L. (Cotton) | Bayer BioScience N.V., Technologiepark 38 B-9052 Gent Belgium | Genetic elements which confer the phenotype insect resistant and glufosinate ammonium herbicide tolerance: cry2: Coding sequence of cry gene from *Bacillus thuringiensis* that confers the insect resistance trait. bar: Coding sequence of the phosphinothricin acetyltransferase gene (bar) from *Streptomyces hygroscopicus* that confers the herbicide resistance trait. |
| B-68 | T303-3 | | Gossypium hirsutum L. (Cotton) | Bayer BioScience N.V., Technologiepark 38 B-9052 Gent Belgium | cry1: Coding sequence of cry gene from *Bacillus thuringiensis* that confers the insect resistance trait. bar: Coding sequence of the phosphinothricin acetyltransferase gene (bar) from *Streptomyces hygroscopicus* that confers the herbicide resistance trait. |
| B-69 | GHB614 | | Gossypium hirsutum L. (Cotton) | Bayer BioScience N.V., Technologiepark 38 B-9052 Gent Belgium | 2mepsps: Coding sequence of 2mepsps from maize that confers the glyphosate herbicide resistance trait. |
| B-70 | X81359 | | Helianthus annuus (Sunflower) | BASF Inc. | Tolerance to imidazolinone herbicides by selection of a naturally occurring mutant. |
| B-71 | RH44 | | Lens culinaris (Lentil) | BASF Inc. | Selection for a mutagenized version of the enzyme acetohydroxyacid synthase (AHAS), also known as acetolactate synthase (ALS) or acetolactate pyruvate-lyase. |
| B-72 | FP967 | | Linum usitatissimum L. (Flax, Linseed) | University of Saskatchewan, Crop Dev. Centre | A variant form of acetolactate synthase (ALS) was obtained from a chlorsulfuron tolerant line of *A. thaliana* and used to transform flax. |
| B-73 | 5345 | | Lycopersicon esculentum (Tomato) | Monsanto Company | Resistance to lepidopteran pests through the introduction of the cry1Ac gene from *Bacillus thuringiensis* subsp. *Kurstaki*. |
| B-74 | 8338 | | Lycopersicon esculentum (Tomato) | Monsanto Company | Introduction of a gene sequence encoding the enzyme 1-amino-cyclopropane-1-carboxylic acid deaminase (ACCd) that metabolizes the precursor of the fruit ripening hormone ethylene. |
| B-75 | 1345-4 | | Lycopersicon esculentum (Tomato) | DNA Plant Technology Corporation | Delayed ripening tomatoes produced by inserting an additional copy of a truncated gene encoding 1-aminocyclopropane-1-carboxyllic acid (ACC) synthase, which resulted in downregulation of the endogenous ACC synthase and reduced ethylene accumulation. |
| B-76 | 35 1 N | | Lycopersicon esculentum (Tomato) | Agritope Inc. | Introduction of a gene sequence encoding the enzyme S-adenosylmethionine hydrolase that metabolizes the precursor of the fruit ripening hormone ethylene |
| B-77 | B, Da, F | | Lycopersicon esculentum (Tomato) | Zeneca Seeds | Delayed softening tomatoes produced by inserting a truncated version of the polygalacturonase (PG) encoding gene in the sense or anti-sense orientation in order to reduce expression of the endogenous PG gene, and thus reduce pectin degradation. |

TABLE 5-continued

| No. | Line/trait | Trade name | Plant | Company | Genetically modified properties |
|---|---|---|---|---|---|
| B-78 | FLAVR SAVR | FLAVR SAVR | *Lycopersicon esculentum* (Tomato) | Calgene Inc. | Delayed softening tomatoes produced by inserting an additional copy of the polygalacturonase (PG) encoding gene in the anti-sense orientation in order to reduce expression of the endogenous PG gene and thus reduce pectin degradation. |
| B-79 | J101, J163 | Roundup Ready Alfalfa | *Medicago sativa* (Alfalfa) | Monsanto Company and Forage Genetics International | Glyphosate herbicide tolerant alfalfa (lucerne) produced by inserting a gene encoding the enzyme 5-enolypyruvylshikimate-3-phosphate synthase (EPSPS) from the CP4 strain of *Agrobacterium tumefaciens*. |
| B-80 | C/F/93/08-02 | | *Nicotiana tabacum* L. (Tobacco) | Societe National d'Exploitation des Tabacs et Allumettes | Tolerance to the herbicides bromoxynil and ioxynil by incorporation of the nitrilase gene from *Klebsiella pneumoniae*. |
| B-81 | Vector 21-41 | | *Nicotiana tabacum* L. (Tobacco) | Vector Tobacco Inc. | Reduced nicotine content through introduction of a second copy of the tobacco quinolinic acid phosphoribosyltransferase (QTPase) in the antisense orientation. The NPTII encoding gene from *E. coli* was introduced as a selectable marker to identify transformants. |
| B-82 | CL121, CL141, CFX51 | | *Oryza sativa* (Rice) | BASF Inc. | Tolerance to the imidazolinone herbicide, imazethapyr, induced by chemical mutagenesis of the acetolactate synthase (ALS) enzyme using ethyl methanesulfonate (EMS). |
| B-83 | IMINTA-1, IMINTA-4 | Clearfield ™ | *Oryza sativa* (Rice) | BASF Inc. | Tolerance to imidazolinone herbicides induced by chemical mutagenesis of the acetolactate synthase (ALS) enzyme using sodium azide. |
| B-84 | LLRICE06, LLRICE62 | LibertyLink ® Rice | *Oryza sativa* (Rice) | Aventis CropScience | Glufosinate ammonium herbicide tolerant rice produced by inserting a modified phosphinothricin acetyltransferase (PAT) encoding gene from the soil bacterium *Streptomyces hygroscopicus*). |
| B-85 | LLRICE601 | | *Oryza sativa* (Rice) | Bayer CropScience (Aventis CropScience (AgrEvo)) | Glufosinate ammonium herbicide tolerant rice produced by inserting a modified phosphinothricin acetyltransferase (PAT) encoding gene from the soil bacterium *Streptomyces hygroscopicus*). |
| B-86 | PWC16 | | *Oryza sativa* (Rice) | BASF Inc. | Tolerance to the imidazolinone herbicide, imazethapyr, induced by chemical mutagenesis of the acetolactate synthase (ALS) enzyme using ethyl methanesulfonate (EMS). |
| B-87 | ATBT04-6, ATBT04-27, ATBT04-30, ATBT04-31, ATBT04-36, SPBT02-5, SPBT02-7 | NewLeaf Atlantic | *Solanum tuberosum* L. (Potato) | Monsanto Company | Colorado potato beetle resistant potatoes produced by inserting the cry3A gene from *Bacillus thuringiensis* (subsp. *Tenebrionis*). |
| B-88 | BT6, BT10, BT12, BT16, BT17, BT18, BT23 | NewLeaf Russet Burbank | *Solanum tuberosum* L. (Potato) | Monsanto Company | Colorado potato beetle resistant potatoes produced by inserting the cry3A gene from *Bacillus thuringiensis* (subsp. *Tenebrionis*). |
| B-89 | RBMT15-101, SEMT15-02, SEMT15-15 | | *Solanum tuberosum* L. (Potato) | Monsanto Company | Colorado potato beetle and potato virus Y (PVY) resistant potatoes produced by inserting the cry3A gene from *Bacillus thuringiensis* (subsp. *Tenebrionis*) and the coat protein encoding gene from PVY. |
| B-90 | RBMT21-129, RBMT21-350, RBMT22-082 | | *Solanum tuberosum* L. (Potato) | Monsanto Company | Colorado potato beetle and potato leafroll virus (PLRV) resistant potatoes produced by inserting the cry3A gene from *Bacillus thuringiensis* (subsp. *Tenebrionis*) and the replicase encoding gene from PLRV. |
| B-91 | AM02-1003, AM01-1005, AM02- | | *Solanum tuberosum* L. (Potato) | BASF Plant Science GmbH | a) A gene containing the coding region of potato gbss in antisense orientation relative to the promoter, flanked by the gbss promoter from *Solanum tuberosum* and the polyadenylation sequence from |

TABLE 5-continued

| No. | Line/trait | Trade name | Plant | Company | Genetically modified properties |
|---|---|---|---|---|---|
| | 1012, AM02-1017, AM99-1089 and AM99-2003 | | | | *Agrobacterium tumefaciens* nopaline synthase gene has been inserted into potato variety Seresta (lines AM02-1003, AM01-1005, AM02-1012) and Kuras (line AM02-1017) thus reducing the amount of amylose in the starch fraction. An ahas gene (acetohydroxyacid synthase) from *Arabidopsis thaliana* flanked by the nos gene promoter and the octopine synthase polyadenylation sequence from *Agrobacterium tumefaciens* serves as selectable marker gene conferring tolerance to Imazamox.<br>b) AM99-1089 serves as a reference line. The inserted gene consists of the potato gbss (granule bound starch synthase) promoter, the coding region of potato gbss in antisense orientation and the polyadenylation sequence from *Agrobacterium tumefaciens* nopaline synthase gene thus reducing the amount of amylose in the starch fraction. In addition the neomycin phosphotransferase gene (nptII) connected to the *Agrobacterium tumefaciens* nopaline synthase promoter and g7 polyadenylation sequence from *Agrobacterium tumefaciens* has been inserted as selectable marker gene conferring resistance to kanamycin.<br>c) In potato line AM99-2003 a gene consisting of gbss promoter from *Solanum tuberosum*, the coding region fragments of be1 and be2 (starch-branching enzyme) in tandem and antisense orientation relative to the promoter and the nos polyadenylation sequence from *Agrobacterium tumefaciens* have been inserted into potato variety Dinamo thus reducing the amount of amylopectin in the starch fraction of the tuber. In addition the neomycin phosphotransferase gene (nptII) connected to the *Agrobacterium tumefaciens* nopaline synthase promoter and g7 polyadenylation sequence from *Agrobacterium tumefaciens* has been inserted as selectable marker gene conferring resistance to kanamycin. |
| B-92 | EH92-527-1 | Amflora | *Solanum tuberosum* L. (Potato) | BASF Plant Science GmbH | In potato event EH92-527-1 a gene consisting of a potato gbss (granule bound starch synthase) promoter, a fragment of the coding region of potato gbss in antisense orientation relative to the promoter and the polyadenylation sequence from *Agrobacterium tumefaciens* nopaline synthase gene (gene construct pHoxwG) have been inserted into potato variety Prevalent thus reducing the amount of amylose in the starch fraction. In addition the neomycin phosphotransferase gene (nptII) connected to the *Agrobacterium tumefaciens nopaline* synthase promoter and polyadenylation signal has been inserted as selectable marker gene conferring resistance to kanamycin. |
| B-93 | AP205CL | | *Triticum aestivum* (Wheat) | BASF Inc. | Selection for a mutagenized version of the enzyme acetohydroxyacid synthase (AHAS), also known as acetolactate synthase (ALS) or acetolactate pyruvate-lyase. |
| B-94 | AP602CL | | *Triticum aestivum* (Wheat) | BASF Inc. | Selection for a mutagenized version of the enzyme acetohydroxyacid synthase (AHAS), also known as acetolactate synthase (ALS) or acetolactate pyruvate-lyase. |

TABLE 5-continued

| No. | Line/trait | Trade name | Plant | Company | Genetically modified properties |
|---|---|---|---|---|---|
| B-95 | BW255-2, BW238-3 | Clearfield ™ | Triticum aestivum (Wheat) | BASF Inc. | Selection for a mutagenized version of the enzyme acetohydroxyacid synthase (AHAS), also known as acetolactate synthase (ALS) or acetolactate pyruvate-lyase. |
| B-96 | MON71800 | | Triticum aestivum (Wheat) | Monsanto Company | Glyphosate tolerant wheat variety produced by inserting a modified 5-enolpyruvylshikimate-3-phosphate synthase (EPSPS) encoding gene from the soil bacterium Agrobacterium tumefaciens, strain CP4. |
| B-97 | SWP965001 | | Triticum aestivum (Wheat) | Cyanamid Crop Protection | Selection for a mutagenized version of the enzyme acetohydroxyacid synthase (AHAS), also known as acetolactate synthase (ALS) or acetolactate pyruvate-lyase. |
| B-98 | DW2, DW6, DW12 | Clearfield ™ | Triticum aestivum (Wheat) | BASF Inc. | |
| B-99 | BW7 | Clearfield ™ | Triticum aestivum (Wheat) | BASF Inc. | Tolerance to imidazolinone herbicides |
| B-100 | Teal 11A | | Triticum aestivum (Wheat) | BASF Inc. | Selection for a mutagenized version of the enzyme acetohydroxyacid synthase (AHAS), also known as acetolactate synthase (ALS) or acetolactate pyruvate-lyase. |
| B-101 | 176 | Knockout ™, NautureGard ™ | Zea mays L. (Maize) | Syngenta Seeds, Inc., Novartis, Mycogen | Insect-resistant maize produced by inserting the cry1Ab gene from Bacillus thuringiensis subsp. kurstaki. The genetic modification affords resistance to attack by the European corn borer (ECB). |
| B-102 | 3751IR | | Zea mays L. (Maize) | Pioneer Hi-Bred International Inc. | Selection of somaclonal variants by culture of embryos on imidazolinone containing media. |
| B-103 | 676, 678, 680 | LibertyLink ® Male Sterile | Zea mays L. (Maize) | Pioneer Hi-Bred International Inc. | Male-sterile and glufosinate ammonium herbicide tolerant maize produced by inserting genes encoding DNA adenine methylase and phosphinothricin acetyltransferase (PAT) from Escherichia coli and Streptomyces viridochromogenes, respectively. |
| B-104 | ACS-ZMØØ3-2 × MON-ØØ81Ø-6 | | Zea mays L. (Maize) | Bayer CropScience (Aventis CropScience (AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-ØØ81Ø-6). |
| B-105 | B16 (DLL25) | | Zea mays L. (Maize) | Dekalb Genetics Corporation | Glufosinate ammonium herbicide tolerant maize produced by inserting the gene encoding phosphinothricin acetyltransferase (PAT) from Streptomyces hygroscopicus. |
| B-106 | BT11 (X4334CBR, X4734CBR) | BiteGard ® | Zea mays L. (Maize) | Syngenta Seeds, Inc. | Insect-resistant and herbicide tolerant maize produced by inserting the cry1Ab gene from Bacillus thuringiensis subsp. kurstaki, and the phosphinothricin N-acetyltransferase (PAT) encoding gene from S. viridochromogenes. |
| B-107 | CBH-351 | StarLink ® | Zea mays L. (Maize) | Aventis CropScience | Insect-resistant and glufosinate ammonium herbicide tolerant maize developed by inserting genes encoding Cry9C protein from Bacillus thuringiensis subsp tolworthi and phosphinothricin acetyltransferase (PAT) from Streptomyces hygroscopicus. |
| B-108 | DAS-06275-8 | | Zea mays L. (Maize) | DOW AgroSciences LLC | Lepidopteran insect resistant and glufosinate ammonium herbicide-tolerant maize variety produced by inserting the cry1F gene from Bacillus thuringiensis var aizawai and the phosphinothricin acetyltransferase (PAT) from Streptomyces hygroscopicus. |
| B-109 | DAS-59122-7 | Herculex RW Rootworm Protection Maise | Zea mays L. (Maize) | DOW AgroSciences LLC and Pioneer Hi-Bred International Inc. | Corn rootworm-resistant maize produced by inserting the cry34Ab1 and cry35Ab1 genes from Bacillus thuringiensis strain PS149B1. The PAT encoding gene from Streptomyces viridochromogenes was introduced as a selectable marker. |

TABLE 5-continued

| No. | Line/trait | Trade name | Plant | Company | Genetically modified properties |
|---|---|---|---|---|---|
| B-110 | DAS-59122-7 × NK603 | | Zea mays L. (Maize) | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Tolerance to glyphosate herbcicide is derived from NK603. |
| B-111 | DAS-59122-7 × TC1507 × NK603 | | Zea mays L. (Maize) | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-Ø15Ø7-1) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Lepidopteran resistance and toleraance to glufosinate ammonium herbicide is derived from TC1507. Tolerance to glyphosate herbcicide is derived from NK603. |
| B-112 | DAS-Ø15Ø7-1 × MON-ØØ6Ø3-6 | | Zea mays L. (Maize) | DOW AgroSciences LLC | Stacked insect resistant and herbicide tolerant corn hybrid derived from conventional cross-breeding of the parental lines 1507 (OECD identifier: DAS-Ø15Ø7-1) and NK603 (OECD identifier: MON-ØØ6Ø3-6). |
| B-113 | DBT418 | Bt-XTRA ® | Zea mays L. (Maize) | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus* |
| B-114 | DK404SR | | Zea mays L. (Maize) | BASF Inc. | Somaclonal variants with a modified acetyl-CoA-carboxylase (ACCase) were selected by culture of embryos on sethoxydim enriched medium. |
| B-115 | EXP1910IT | | Zea mays L. (Maize) | Syngenta Seeds, Inc. (formerly Zeneca Seeds) | Tolerance to the imidazolinone herbicide, imazethapyr, induced by chemical mutagenesis of the acetolactate synthase (ALS) enzyme using ethyl methanesulfonate (EMS). |
| B-116 | GA21 | Roundup Ready ® | Zea mays L. (Maize) | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. |
| B-117 | IT | | Zea mays L. (Maize) | Pioneer Hi-Bred International Inc. | Tolerance to the imidazolinone herbicide, imazethapyr, was obtained by in vitro selection of somaclonal variants. |
| B-118 | LY038 | Mavera ™ High Value Corn with Lysine | Zea mays L. (Maize) | Monsanto Company | Altered amino acid composition, specifically elevated levels of lysine, through the introduction of the cordapA gene, derived from *Corynebacterium glutamicum*, encoding the enzyme dihydrodipicolinate synthase (cDHDPS). |
| B-119 | MIR604 | Agrisure RW Rootworm-Protected Corn | Zea mays L. (Maize) | Syngenta Seeds, Inc. | Corn rootworm resistant maize produced by transformation with a modified cry3A gene. The phosphomannose isomerase gene from *E. coli* was used as a selectable marker. |
| B-120 | MON80100 | | Zea mays L. (Maize) | Monsanto Company | Insect-resistant maize produced by inserting the cry1Ab gene from *Bacillus thuringiensis* subsp. *kurstaki*. The genetic modification affords resistance to attack by the European corn borer (ECB). |

TABLE 5-continued

| No. | Line/trait | Trade name | Plant | Company | Genetically modified properties |
|---|---|---|---|---|---|
| B-121 | MON802 | Roundup Ready ® | Zea mays L. (Maize) | Monsanto Company | Insect-resistant and glyphosate herbicide tolerant maize produced by inserting the genes encoding the Cry1Ab protein from Bacillus thuringiensis and the 5-enolpyruvylshikimate-3-phosphate synthase (EPSPS) from A. tumefaciens strain CP4. |
| B-122 | MON809 | | Zea mays L. (Maize) | Pioneer Hi-Bred International Inc. | Resistance to European corn borer (Ostrinia nubilalis) by introduction of a synthetic cry1Ab gene. Glyphosate resistance via introduction of the bacterial version of a plant enzyme, 5-enolpyruvyl shikimate-3-phosphate synthase (EPSPS). |
| B-123 | MON810 | YieldGard ® | Zea mays L. (Maize) | Monsanto Company | Insect-resistant maize produced by inserting a truncated form of the cry1Ab gene from Bacillus thuringiensis subsp. kurstaki HD-1. The genetic modification affords resistance to attack by the European corn borer (ECB). |
| B-124 | MON810 × MON88017 | | Zea mays L. (Maize) | Monsanto Company | Stacked insect resistant and glyphosate tolerant maize derived from conventional cross-breeding of the parental lines MON810 (OECD identifier: MON-ØØ81Ø-6) and MON88017 (OECD identifier: MON-88Ø17-3). European corn borer (ECB) resistance is derived from a truncated form of the cry1Ab gene from Bacillus thuringiensis subsp. kurstaki HD-1 present in MON810. Corn rootworm resistance is derived from the cry3Bb1 gene from Bacillus thuringiensis subspecies kumamotoensis strain EG4691 present in MON88017. Glyphosate tolerance is derived from a 5-enolpyruvylshikimate-3-phosphate synthase (EPSPS) encoding gene from Agrobacterium tumefaciens strain CP4 present in MON88017. |
| B-125 | MON832 | | Zea mays L. (Maize) | Monsanto Company | Introduction, by particle bombardment, of glyphosate oxidase (GOX) and a modified 5-enolpyruvyl shikimate-3-phosphate synthase (EPSPS), an enzyme involved in the shikimate biochemical pathway for the production of the aromatic amino acids. |
| B-126 | MON863 | YieldGard ® Rootworm | Zea mays L. (Maize) | Monsanto Company | Corn root worm resistant maize produced by inserting the cry3Bb1 gene from Bacillus thuringiensis subsp. kumamotoensis. |
| B-127 | MON88017 | | Zea mays L. (Maize) | Monsanto Company | Corn rootworm-resistant maize produced by inserting the cry3Bb1 gene from Bacillus thuringiensis subspecies kumamotoensis strain EG4691. Glyphosate tolerance derived by inserting a 5-enolpyruvylshikimate-3-phosphate synthase (EPSPS) encoding gene from Agrobacterium tumefaciens strain CP4. |
| B-128 | MON-ØØ6Ø3-6 × MON-ØØ81Ø-6 | | Zea mays L. (Maize) | Monsanto Company | Stacked insect resistant and herbicide tolerant corn hybrid derived from conventional cross-breeding of the parental lines NK603 (OECD identifier: MON-ØØ6Ø3-6) and MON810 (OECD identifier: MON-ØØ81Ø-6). |
| B-129 | MON-ØØ81Ø-6 × LY038 | | Zea mays L. (Maize) | Monsanto Company | Stacked insect resistant and enhanced lysine content maize derived from conventional cross-breeding of the parental lines MON810 (OECD identifier: MON-ØØ81Ø-6) and LY038 (OECD identifier: REN-ØØØ38-3). |
| B-130 | MON-ØØ863-5 × MON-ØØ6Ø3-6 | | Zea mays L. (Maize) | Monsanto Company | Stacked insect resistant and herbicide tolerant corn hybrid derived from conventional cross-breeding of the parental lines MON863 (OECD identifier: MON-ØØ863-5) and NK603 (OECD identifier: MON-ØØ6Ø3-6). |

TABLE 5-continued

| No. | Line/trait | Trade name | Plant | Company | Genetically modified properties |
|---|---|---|---|---|---|
| B-131 | MON-ØØ863-5 × MON-ØØ81Ø-6 | YieldGard ® Plus | Zea mays L. (Maize) | Monsanto Company | Stacked insect resistant corn hybrid derived from conventional cross-breeding of the parental lines MON863 (OECD identifier: MON-ØØ863-5) and MON810 (OECD identifier: MON-ØØ81Ø-6) |
| B-132 | MON-ØØ863-5 × MON-ØØ81Ø-6 × MON-ØØ6Ø3-6 | YieldGard ® Plus, Roundup Ready ® | Zea mays L. (Maize) | Monsanto Company | Stacked insect resistant and herbicide tolerant corn hybrid derived from conventional cross-breeding of the stacked hybrid MON-ØØ863-5 × MON-ØØ81Ø-6 and NK603 (OECD identifier: MON-ØØ6Ø3-6). |
| B-133 | MON-ØØØ21-9 × MON-ØØ81Ø-6 | | Zea mays L. (Maize) | Monsanto Company | Stacked insect resistant and herbicide tolerant corn hybrid derived from conventional cross-breeding of the parental lines GA21 (OECD identifider: MON-ØØØ21-9) and MON810 (OECD identifier: MON-ØØ81Ø-6). |
| B-134 | MS3 | | Zea mays L. (Maize) | Bayer CropScience (Aventis CropScience (AgrEvo)) | Male sterility caused by expression of the barnase ribonuclease gene from Bacillus amyloliquefaciens; PPT resistance was via PPT-acetyltransferase (PAT). |
| B-135 | MS6 | LibertyLink ® Male Sterile | Zea mays L. (Maize) | Bayer CropScience (Aventis CropScience (AgrEvo)) | Male sterility caused by expression of the barnase ribonuclease gene from Bacillus amyloliquefaciens; PPT resistance was via PPT-acetyltransferase (PAT). |
| B-136 | NK603 | Roundup Ready ® corn | Zea mays L. (Maize) | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. |
| B-137 | SYN-BTØ11-1 × MON-ØØØ21-9 | | Zea mays L. (Maize) | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØØ21-9). |
| B-138 | T14, T25 | LibertyLink ™ | Zea mays L. (Maize) | Bayer CropScience (Aventis CropScience (AgrEvo)) | Glufosinate herbicide tolerant maize produced by inserting the phosphinothricin N-acetyltransferase (PAT) encoding gene from the aerobic actinomycete Streptomyces viridochromogenes. |
| B-139 | TC1507 | Herculex I ® | Zea mays L. (Maize) | Mycogen (c/o Dow AgroSciences); Pioneer (c/o Dupont) | Insect-resistant and glufosinate ammonium herbicide tolerant maize produced by inserting the cry1F gene from Bacillus thuringiensis var. aizawai and the phosphinothricin N-acetyltransferase encoding gene from Streptomyces viridochromogenes. |
| B-140 | TC1507 × DAS-59122-7 | | Zea mays L. (Maize) | DOW AgroSciences LLC and Pioneer Hi-Bred International Inc. | Stacked insect resistant and herbicide tolerant maize produced by conventional cross breeding of parental lines TC1507 (OECD unique identifier: DAS-Ø15Ø7-1) with DAS-59122-7 (OECD unique identifier: DAS-59122-7). Resistance to lepidopteran insects is derived from TC1507 due the presence of the cry1F gene from Bacillus thuringiensis var. aizawai. Corn rootworm-resistance is derived from DAS-59122-7 which contains the cry34Ab1 and cry35Ab1 genes from Bacillus thuringiensis strain PS149B1. Tolerance to glufosinate ammonium herbcicide is derived from TC1507 from the phosphinothricin N-acetyltransferase encoding gene from Streptomyces viridochromogenes. |
| B-141 | SYTGA21 | | Zea mays L. (Maize) | Syngenta Agrisure GT | Glyphosate Herbicide Tolerance |
| B-142 | SYTGA21 + Bt11 | | Zea mays L. (Maize) | Syngenta Agrisure GT/CB YieldGard Liberty Link | Cry1Ab Corn borer protection Glyphosate Herbicide Tolerance |

TABLE 5-continued

| No. | Line/trait | Trade name | Plant | Company | Genetically modified properties |
|---|---|---|---|---|---|
| B-143 | MON810 + SYTGA21 | | Zea mays L. (Maize) | Monsanto YieldGard Roundup Ready | Cry1Ab corn borer resistance Glyphosate Herbicide Tolerance |
| B-144 | MON89034 | | Zea mays L. (Maize) | Monsanto Agrar Deutschland GmbH | A full description of the genetic elements in MON 89034, including the approximate size, source and function is provided in Table 1.<br>Table 1. Summary of the genetic elements inserted in MON 89034<br>B1-Left Border*: 239 bp DNA region from the B?Left Border region remaining after integration<br>Pp2-e35S: Modified promoter and leader for the cauliflower mosaic virus (CaMV) 35S RNA containing the duplicated enhancer region<br>L3-Cab: 5' untranslated leader of the wheat chlorophyll a/b?binding protein<br>I4-Ract1: Intron from the rice actin gene<br>CS5-cry1A.105: Coding sequence for the *Bacillus thuringiensis* Cry1A.105 protein<br>T6-Hsp17: 3' transcript termination sequence for wheat heat shock protein 17.3, which ends transcription and directs polyadenylation<br>P-FMV: Figwort Mosaic Virus 35S promoter<br>I-Hsp70: First intron from the maize heat shock protein 70 gene<br>TS7-SSU-CTP: DNA region containing the targeting sequence for the transit peptide region of maize ribulose 1,5-bisphosphate carboxylase small subunit and the first intron<br>CS-cry2Ab2: Coding sequence for a Cry2Ab2 protein from *Bacillus thuringiensis*. This coding sequence uses a modified codon usage.<br>T-nos: 3' transcript termination sequence of the nopaline synthase (nos) coding sequence from *Agrobacterium tumefaciens* which terminates transcription and directs polyadenylation<br>B-Left Border: 230 bp DNA region from the B-Left Border region remaining after integration<br>*Analyses of the MON 89034 insert sequence revealed that the e35S promoter that regulates expression of the cry1A.105 coding sequence was modified: the Right Border sequence present in PV-ZMIR245 was replaced by the Left Border sequence. It is likely that this modification is the result of a crossover recombination event that occurred prior to the DNA being inserted into the genome. |
| B-145 | MON 89034 × MON 88017 | | Zea mays L. (Maize) | Monsanto Agrar Deutschland GmbH | |
| B-146 | MON 89034 × NK603 | | Zea mays L. (Maize) | Monsanto Agrar Deutschland GmbH | |
| B-147 | DP-Ø98140-6 | | Zea mays L. (Maize) | Pioneer Hi-Bred Seeds Agro SRL | 98140 maize has been genetically modified by insertion of the glyphosate-N-acetyltransferase (gat4621) gene and a modified maize acetolactate synthase (zm-hra) gene, along with the necessary regulatory elements for gene expression in the maize plant.<br>The gat4621 gene encodes the GAT4621 protein, which was derived from the soil bacterium *Bacillus licheniformis*, and confers tolerance to herbicides containing glyphosate. The zm-hra gene encodes the ZM-HRA |

TABLE 5-continued

| No. | Line/trait | Trade name | Plant | Company | Genetically modified properties |
|---|---|---|---|---|---|
| | | | | | protein and confers tolerance to a range of ALS-inhibiting herbicides such as sulfonylureas. |
| B-148 | 3243M | | *Zea mays L.* (*Maize*) | Syngenta Seeds SA | Regulatory sequences: Promoter sequences derived from maize. The function of these sequences is to control expression of the insect resistance gene. Insect resistance gene: cry1Ab gene derived form *Bacillus thuringiensis*. The function of the product of this gene is to confer resistance to certain lepidopteran pests. NOS terminator: Terminator sequence of the nopaline synthase gene, isolated from *Agrobacterium tumefaciens*. The function of this sequence is to signal the termination of the insect resistance gene expression. ZmUbiIntron: Promoter from a maize ubiquitin gene together with the first intron of the gene. The function of these sequences is to control and enhance expression of the Phosphomannose Isomerase (pmi) gene. pmi: Coding sequence of the Phosphomannose Isomerase (pmi) gene isolated from *Escherichia coli*. The function of this gene product is as a selectable marker for the transformation, as it allows positive selection of transformed cells growing on mannose. NOS terminator: Termination sequence of the nopaline synthase gene, isolated from *Agrobacterium tumefaciens*. The function of this sequence is to signal the termination of the marker gene (pmi) expression. |
| B-149 | DP 444 BG/RR | Bollgard/Roundup Ready, from US 2003213029-A1 | *Gossypium hirsutum L.* (Cotton) | Delta and Pine Land company | Bollgard ®, RoundupReady ® |
| B-150 | VSN-BTCRW | Bt-toxin corn root worm | *Zea mays L.* (Maize) | | |
| B-151 | HCL201CR W2RR × LH324 | Bt-toxin corn root worm | *Zea mays L.* (Maize) | Monsanto Company | |
| B-152 | LH324 | from U.S. Pat. No. 7,223,908 B1 | *Zea mays L.* (Maize) | Monsanto Company | |
| B-153 | VSN-RR Bt | RoundupReady Bt-toxin | *Zea mays L.* (Maize) | | |
| B-154 | FR1064LL × FR2108 | Ref: Gerdes, J. T., Behr, C. F., Coors, J. G., and Tracy, W. F. 1993. Compilation of North American Maize Breeding Germplasm. W. F. Tracy, J. G. Coors, and J. L. Geadelmann, eds. Crop Science Society of America, Madison, WI and U.S. Pat. No. 6,407,320 B1 | *Zea mays L.* (Maize) | Illinois Foundation Seeds | |
| B-155 | VSN-Bt | Bt-toxin | *Zea mays L.* (Maize) | | |

TABLE 6

| No. | Trade name | Plant | Company | Genetically modified properties | Additional information |
|---|---|---|---|---|---|
| 4-1 | Roundup Ready ® | *Beta vulgaris* (Sugar Beet) | Monsanto Company | tolerance to glyphosate | |
| 4-2 | InVigor ® | *Brassica napus* (Argentine Canola) | BayerCropScience | Canola has been genetically modified to: Ø express a gene conferring tolerance to the herbicide glufosinate ammonium; Ø introduce a novel hybrid breeding system for canola, based on genetically modified male sterile (MS) and fertility restorer (RF) lines; Ø express an antibiotic resistance gene. | |
| 4-3 | Liberty Link ® | *Brassica napus* (Argentine Canola) | BayerCropScience | tolerance to phosphinotricin | |
| 4-4 | Roundup Ready ® | *Brassica napus* (Canola) | Monsanto Company | tolerance to glyphosate | |
| 4-5 | Clearfield ® | Canola | BASF Corporation | non-GMO, tolerance to imazamox | |
| 4-6 | Optimum ™ GAT ™ | *Glycine max* L. (Soybean) | Pioneer Hi-Bred International, Inc | tolerance to glyphosate and ALS herbicides | |
| 4-7 | Roundup Ready ® | *Glycine max* L. (Soybean) | Monsanto Company | tolerance to glyphosate | |
| 4-8 | Roundup RReady2Yield ™ | *Glycine max* L. (Soybean) | Monsanto Company | tolerance to glyphosate | |
| 4-9 | STS ® | *Glycine max* L. (Soybean) | DuPont | tolerance to sulphonylureas | |
| 4-10 | YIELD GARD ® | *Glycine max* L. (Soybean) | Monsanto Company | | |
| 4-11 | AFD ® | *Gossypium hirsutum* L. (Cotton) | BayerCropScience | lines include eg AFD5062LL, AFD5064F, AFD5065B2F, AFD seed is available in several varieties with technology incorporated, such as Bollgard ®, Bollgard II, Roundup Ready, Roundup Ready Flex and LibertyLink ® technologies. | |
| 4-12 | Bollgard II ® | *Gossypium hirsutum* L. (Cotton) | Monsanto Company | MON 15985 event: Cry2(A)b1; Cry1A(c) | |
| 4-13 | Bollgard ® | *Gossypium hirsutum* L. (Cotton) | Monsanto Company | Cry 1Ac | |
| 4-14 | FiberMax ® | *Gossypium hirsutum* L. (Cotton) | BayerCropScience | | |
| 4-15 | Liberty Link ® | *Gossypium hirsutum* L. (Cotton) | BayerCropScience | tolerance to phosphinotricin | |
| 4-16 | Nucotn 33B | *Gossypium hirsutum* L. (Cotton) | Delta Pine and Land | Bt-toxin in Delta Pine lines: Cry1Ac | |
| 4-17 | Nucotn 35B | *Gossypium hirsutum* L. (Cotton) | Delta Pine and Land | Bt-toxin in Delta Pine lines: Cry1Ac | |
| 4-18 | Nucotn ® | *Gossypium hirsutum* L. (Cotton) | Delta Pine and Land | Bt-toxin in Delta Pine lines | |
| 4-19 | PhytoGen ™ | *Gossypium hirsutum* L. (Cotton) | PhytoGen Seed Company, Dow AgroSciences LLC | covers varieties containing for example Roundup Ready flex, Widestrike, | |
| 4-20 | Roundup Ready Flex ® | *Gossypium hirsutum* L. (Cotton) | Monsanto Company | tolerance to glyphosate | |
| 4-21 | Roundup Ready ® | *Gossypium hirsutum* L. (Cotton) | Monsanto Company | tolerance to glyphosate | |

TABLE 6-continued

| No. | Trade name | Plant | Company | Genetically modified properties | Additional information |
|---|---|---|---|---|---|
| 4-22 | Widestrike ™ | *Gossypium hirsutum* L. (Cotton) | Dow AgroSciences LLC | Cry1F and Cry1Ac | Monsanto/Dow |
| 4-23 | YIELD GARD ® | *Gossypium hirsutum* L. (Cotton) | Monsanto Company | | www.garstseed.com/GarstClient/Technology/agrisure.aspx |
| 4-24 | Roundup Ready ® | *Medicago sativa* (Alfalfa) | Monsanto Company | tolerance to glyphosate | |
| 4-25 | Clearfield ® | *Oryza sativa* (Rice) | BASF Corporation | non-GMO, tolerance to imazamox | |
| 4-26 | NewLeaf ® | *Solanum tuberosum* L. (Potato) | Monsanto Company | resistant to infection by Potato Leafroll Virus (PLRV) and to feeding by the Colorado potato beetle, *Leptinotarsa decemlineata* (CPB) | |
| 4-27 | NewLeaf ® plus | *Solanum tuberosum* L. (Potato) | Monsanto Company | resistant to infection by Potato Leafroll Virus (PLRV) and to feeding by the Colorado potato beetle, *Leptinotarsa decemlineata* (CPB) | |
| 4-28 | Protecta ® | *Solanum tuberosum* L. (Potato) | ? | | |
| 4-29 | Clearfield ® | Sunflower | BASF Corporation | non-GMO, tolerance to imazamox | |
| 4-30 | Roundup Ready ® | *Triticum aestivum* (Wheat) | Monsanto Company | tolerance to glyphosate, NK603 | |
| 4-31 | Clearfield ® | Wheat | BASF Corporation | non-GMO, tolerance to imazamox | |
| 4-32 | Agrisure ® (Family) | *Zea mays* L. (Maize) | Syngenta Seeds, Inc. | includes Agrisure CB/LL (BT 11 event plus tolerance towards phosphinotricin by GA21 event); Agrisure CB/LL/RW (Bt 11 event, modified synthetic Cry3A gene, tolerance towards phosphinotricin by GA21 event); Agrisure GT (tolerance to glyphosate); Agrisure GT/CB/LL (tolerance to glyphosate and towards phosphinotricinby GA21 event, Bt 11 event); Agrisure 3000GT (CB/LL/RW/GT: tolerance to glyphosate and towards phosphinotricinby GA21 event, Bt 11 event, modified synthetic Cry3A gene); Agrisure GT/RW (tolerance to glyphosate, modified synthetic Cry3A gene); Agrisure RW (modified synthetic Cry3A gene); Future Traits | |
| 4-33 | BiteGard ® | *Zea mays* L. (Maize) | Novartis Seeds | cry1A(b) gene. | |
| 4-34 | Bt-Xtra ® | *Zea mays* L. (Maize) | DEKALB Genetics Corporation | cry1Ac gene. | |
| 4-35 | Clearfield ® | *Zea mays* L. (Maize) | BASF Corporation | non-GMO, tolerance to imazamox | |
| 4-36 | Herculex ® (Family) | *Zea mays* L. (Maize) | Dow AgroSciences LLC | | |
| 4-37 | IMI ® | *Zea mays* L. (Maize) | DuPont | tolerance to imidazolinones | |
| 4-38 | KnockOut ® | *Zea mays* L. (Maize) | Syngenta Seeds, Inc. | SYN-EV176-9: cry1A(b) gene. | |

TABLE 6-continued

| No. | Trade name | Plant | Company | Genetically modified properties | Additional information |
|---|---|---|---|---|---|
| 4-39 | Mavera ® | Zea mays L. (Maize) | Renessen LLC | high Lysine | www.dowagro.com/widestrike/ |
| 4-40 | NatureGard ® | Zea mays L. (Maize) | Mycogen | cry1A(b) gene. | |
| 4-41 | Roundup Ready ® | Zea mays L. (Maize) | Monsanto Company | tolerance to glyphosate | www.starlinkcorn.com/starlinkcorn.htm |
| 4-42 | Roundup Ready ® 2 | Zea mays L. (Maize) | Monsanto Company | tolerance to glyphosate | |
| 4-43 | SmartStax | Zea mays L. (Maize) | Monsanto Company | eight gene stack | |
| 4-44 | StarLink ® | Zea mays L. (Maize) | Aventis CropScience ->Bayer CropScience | Cry9c gene. | |
| 4-45 | STS ® | Zea mays L. (Maize) | DuPont | tolerance to sulphonylureas | |
| 4-46 | YIELD GARD ® | Zea mays L. (Maize) | Monsanto Company | Mon810, Cry1Ab1; resistant to corn borer | www.dowagro.com/herculex/about/herculexfamily/ |
| 4-47 | YieldGard ® Plus | Zea mays L. (Maize) | Monsanto Company | Mon810xMon863, double-stack, resistant to corn borer and rootworm | |
| 4-48 | YieldGard ® Rootworm | Zea mays L. (Maize) | Monsanto Company | Mon863, Cry3Bb1, resistant to rootworm | |
| 4-49 | YieldGard ® VT | Zea mays L. (Maize) | Monsanto Company | stacked trait | |
| 4-50 | YieldMaker ™ | Zea mays L. (Maize) | DEKALB Genetics Corporation | include Roundup Ready 2 technology, YieldGard VT, YieldGard Corn Borer, YieldGard Rootworm and YieldGard Plus | |

EXAMPLES

The invention is illustrated in more detail by the examples below, without being limited thereby.

A synergistic effect in insecticides and acaricides is always present when the action of the active compound combinations exceeds the total of the actions of the active compounds when applied individually.

The expected action for a given combination of two active compounds can be calculated as follows, using the formula of S. R. Colby, Weeds 15 (1967), 20-22:

If

X is the kill rate, expressed as % of the untreated control, when employing active compound A at an application rate of m g/ha or in a concentration of m ppm, Y is the kill rate, expressed as % of the untreated control, when employing the transgenic seed and E is the kill rate, expressed as % of the untreated control, when employing the active compound A at application rates of m g/ha or in a concentration of m ppm and the transgenic seed, then $$E = X + Y - \frac{X \cdot Y}{100}$$

If the actual insecticidal kill rate exceeds the calculated value, the action of the combination is superadditive, i.e. a synergistic effect is present. In this case, the actually observed kill rate must exceed the value calculated using the above formula for the expected kill rate (E).

Example 1: Foliar and Drench Application *Aphis gossypii*/Cotton

Individual potted genetically modified cotton plants with Lepidoptera resistance and Glyphosate resistance are treated with the desired product against the cotton aphid (*Aphis gossypii*).

After the desired period of time, the kill in % is determined. 100% means that all the aphids have been killed; 0% means that none of the aphids have been killed.

A considerable improvement in the control of pests compared to the control plants not treated according to the invention is noticeable.

TABLE B1-1

*Aphis gossypii* test (foliar application)

| Active compound | Concentration in ppm | Kill in % after $1^d$ | |
|---|---|---|---|
| compound I-8 | 20 | 65 | |
| cotton plant containing a gene from the cry family for Lepidoptera resistence and a gene for Glyphosate resistence | | 0 | |
| | | found* | calc.** |
| compound I-8 combined with a cotton plant containing a gene from the cry family for Lepidoptera resistence and a gene for Glyphosate resistence according to the invention | 20 | 85 | 65 |

TABLE B1-2

Aphis gossypii test (drench application)

| Active compound | Concentration in ppm | Kill in % after $2^d$ | | |
|---|---|---|---|---|
| compound I-8 | 0.8 | 70 | | |
| cotton plant containing a gene from the cry family for Lepidoptera resistance and a gene for Glyphosate resistance | | 0 | | |
| | | | found* | calc.** |
| compound I-8 combined with a cotton plant containing a gene from the cry family for Lepidoptera resistance and a gene for Glyphosate resistance according to the invention | 0.8 | | 90 | 70 |

*found = activity found
**calc. = activity calculated using the Colby formula

Example 2: Foliar Application *Spodoptera frugiperda*/Maize

Pots with in each case 5 genetically modified maize plants with Lepidoptera, Coleoptera and/or herbicide resistances are treated in 2 replications against the armyworm (*Spodoptera frugiperda*).

After the desired period of time, the kill in % is determined. 100% means that all caterpillars have been killed; 0% means that none of the caterpillars have been killed.

A considerable improvement in the control of pests compared to the control plants not treated according to the invention is noticeable.

TABLE B2

Spodoptera frugiperda test (foliar application)

| Active compound | Concentration in ppm | Kill in % after $4^d$ | | |
|---|---|---|---|---|
| compound I-8 | 100 | 0 | | |
| maize plant containing a gene from the cry family for Lepidoptera resistance | | 40 | | |
| maize plant containing a gene from the cry family for Coleoptera resistence and a gene for Glyphosate resistance | | 20 | | |
| | | | found* | calc.** |
| compound I-8 combined with a maize plant containing a gene from the cry family for Lepidoptera resistence according to the invention | 100 | | 90 | 40 |
| compound I-8 combined with a maize plant containing a gene from the cry family for Coleoptera resistence and a gene for Glyphosate resistance according to the invention | 100 | | 50 | 20 |

*found = activity found
**calc. = activity calculated using the Colby formula

The invention claimed is:

1. A method for improving production of a genetically modified plant, wherein the plant comprises at least one gene or gene fragment coding for a Bt toxin, comprising treating parts of the plant with from 50 to 200 g/ha of [1-(6-trifluoromethylpyridin-3-yl)ethyl](methyl)-oxido-λ⁴-sulphanylidenecyanamide:

(I-8)

to improve the production of the plant, wherein the improvement is caused by a synergistic action between (I-8) and a genetic modification of the genetically modified plant, wherein the parts of the plant are selected from the group consisting of shoots, leaves, flowers, roots, needles, stems, trunks, fruit-bodies, fruit, tubers, rhizomes, and combinations thereof, and wherein (I-8) is the only active compound with which the genetically modified plant is treated.

2. The method according to claim 1, wherein the genetically modified plant further is tolerant to one or more herbicides, wherein the herbicide tolerance is obtained by genetic transformation or selection of a plant containing a mutation.

3. The method according to claim 1, wherein the genetically modified plant is selected from the group consisting of *Dianthus caryophyllus* (carnation), *Brassica napus* (Argentine oilseed rape), *Zea mays* L. (maize), *Cucumis melo* (melon), *Carica papaya* (papaya), *Solanum tuberosum* L (potato), *Glycine max* L. (soya bean), *Cucurbita pepo* (pumpkin), *Nicotiana tabacum* L. (tobacco), *Lycopersicon esculentum* (tomato), *Agrostis stonolifera* (creeping bentgrass), *Beta vulgaris* (sugar beet), *Brassica napus* (Argentine canola), *Brassica rapa* (Polish canola), *Cichorium intybus* (chicory), *Cucurbita pepo* (squash), *Gossypium hirsutum* L. (cotton), *Helianthus annuus* (sunflower), *Lens culinaris* (lentil), *Lens usitatissimum* L. (flax, linseed), *Medicago sativa* (alfalfa), *Oryza sativa* (rice), *Triticum aestivum* (wheat), and *Brassicus napus* (canola), and wherein the gene or gene fragment coding for a Bt toxin codes for a crystal toxin (Cry).

4. The method according to claim 1, wherein the genetically modified plant is a vegetable plant, maize plant, soya bean plant, cotton plant, tobacco plant, rice plant, sugar beet plant, oilseed rape plant, or potato plant.

5. The method according to claim 1, wherein [1-(6-trifluoromethylpyridin-3-yl)ethyl](methyl)-oxido-λ⁴-sulphanylidenecyanamide is in a mixture with at least one mixing partner.

6. The method according to claim 1, wherein the genetically modified plant is a maize plant, soya bean plant, tobacco plant, sugar beet plant, oilseed rape plant, or potato plant.

7. The method according to claim 1, wherein the genetically modified plant is a cotton plant.

8. The method according to claim 1, wherein the genetically modified plant is a maize plant.

9. The method according to claim 1, wherein the genetically modified plant is a soya bean plant.

10. The method according to claim 1, wherein the genetically modified plant is a tobacco plant.

11. The method according to claim 1, wherein the genetically modified plant is a rice plant.

12. The method according to claim 1, wherein the genetically modified plant is a sugar beet plant.

13. The method according to claim 1, wherein the genetically modified plant is an oilseed rape plant.

14. The method according to claim 1, wherein the genetically modified plant is a potato plant.

15. The method according to claim 1, wherein the Bt toxin is a crystal toxin.

16. The method according to claim 2, wherein the herbicide tolerance is glyphosate tolerance, glutamine synthase tolerance, hydroxyphenylpyruvatedioxygenase tolerance, acetolactate synthase tolerance, sulphonylurea tolerance, and/or imidazolinone tolerance.

17. The method of claim 1, wherein the genetically modified plant is a cotton plant including a gene from the Cry family for Lepidoptera resistance and a gene for glyphosate resistance.

18. The method of claim 1, wherein the genetically modified plant is a maize plant including a gene from the Cry family for Lepidoptera resistance and a gene for glyphosate resistance.

19. The method of claim 1, wherein the genetically modified plant is a maize plant including a gene from the Cry family for Coleoptera resistance and a gene for glyphosate resistance.

20. A method for improving production of a genetically modified plant, wherein the plant comprises at least one gene or gene fragment coding for a Bt toxin, comprising treating parts of the plant in the presence of an insect pest with from 50 to 200 g/ha of [1-(6-trifluoromethylpyridin-3-yl)ethyl](methyl)-oxido-$\lambda^4$-sulphanylidenecyanamide:

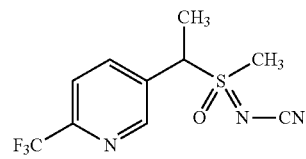

(I-8)

to improve the production of the plant, wherein the improvement is caused by a synergistic action between (I-8) and a genetic modification of the genetically modified plant, wherein the parts of the plant are selected from the group consisting of shoots, leaves, flowers, roots, needles, stems, trunks, fruit-bodies, fruit, tubers, rhizomes, and combinations thereof, and wherein (I-8) is the only active compound with which the genetically modified plant is treated.

* * * * *